United States Patent
Ando et al.

(10) Patent No.: US 7,530,511 B2
(45) Date of Patent: May 12, 2009

(54) HIGH PRESSURE HOMOGENIZING APPARATUS AND METHOD THEREOF

(76) Inventors: Shigeo Ando, 973-14, Matsumotocho 3-chome, Chohshi, Chiba (JP) 288-0802; Masao Ando, 973-21, Matsumotocho 3-chome, Chohshi, Chiba (JP) 288-0802; Toyoroku Ando, 169-4, Myohjincho 1-chome, Chohshi, Chiba (JP) 288-0002

( * ) Notice: Subject to any disclaimer, the term of this patent is extended or adjusted under 35 U.S.C. 154(b) by 267 days.

(21) Appl. No.: 11/175,179

(22) Filed: Jul. 7, 2005

(65) Prior Publication Data

US 2006/0011755 A1 Jan. 19, 2006

(30) Foreign Application Priority Data

Jul. 13, 2004 (JP) ............................. 2004-205502
Sep. 30, 2004 (JP) ............................. 2004-286115
Mar. 31, 2005 (JP) ............................. 2005-103245

(51) Int. Cl.
*B02C 15/00* (2006.01)
(52) U.S. Cl. .................................... 241/270; 241/283
(58) Field of Classification Search .................. 241/2, 241/283, 270
See application file for complete search history.

(56) References Cited

U.S. PATENT DOCUMENTS

| | | | |
|---|---|---|---|
| 5,411,380 A | 5/1995 | Bristol et al. | |
| 7,175,117 B2 * | 2/2007 | Naito | ........................... 241/39 |
| 2006/0131451 A1 | 6/2006 | Naito | |

FOREIGN PATENT DOCUMENTS

| | | |
|---|---|---|
| DE | 19933440 | 1/2001 |
| EP | 0256241 | 2/1988 |
| EP | 1550508 | 7/2005 |
| GB | 1448117 | 9/1976 |
| JP | S60-19921 | 5/1985 |
| WO | WO 2004/026481 | 4/2004 |

OTHER PUBLICATIONS

Ext. European Search Rep., Oct. 12, 2006, Exr. Axel Brunold.
Office action from SINO, May 9, 2008, Liu.
Office action from KIPO, May 30, 2008, Korean Patent Examiner.

* cited by examiner

*Primary Examiner*—Bena Miller
(74) *Attorney, Agent, or Firm*—Lau and Associates, LLC

(57) ABSTRACT

The present invention is a high pressure homogenizing apparatus and a method for dividing a fine solid material or fibrous cellulose of chemical, medical, and resin products in suspension as a dispersion or emulsification, or dividing by crushing cell membranes of fungi with high efficiency. The apparatus is free from valve damages to simplify maintenance and control. The high pressure homogenizing apparatus to finely divide a raw material in suspension includes a high pressure homogenizing device having an orifice, a raw material receiving passage connected to the high pressure homogenizing device, a processing piston, and a processing recess disposed in a receiver. A front end of the processing piston is inserted into the processing recess with a pressure intensifier and a volume compression inside the processing recess pressurizes the suspension in the processing recess to lead the suspension into the raw material receiving passage for dividing the raw material.

27 Claims, 47 Drawing Sheets

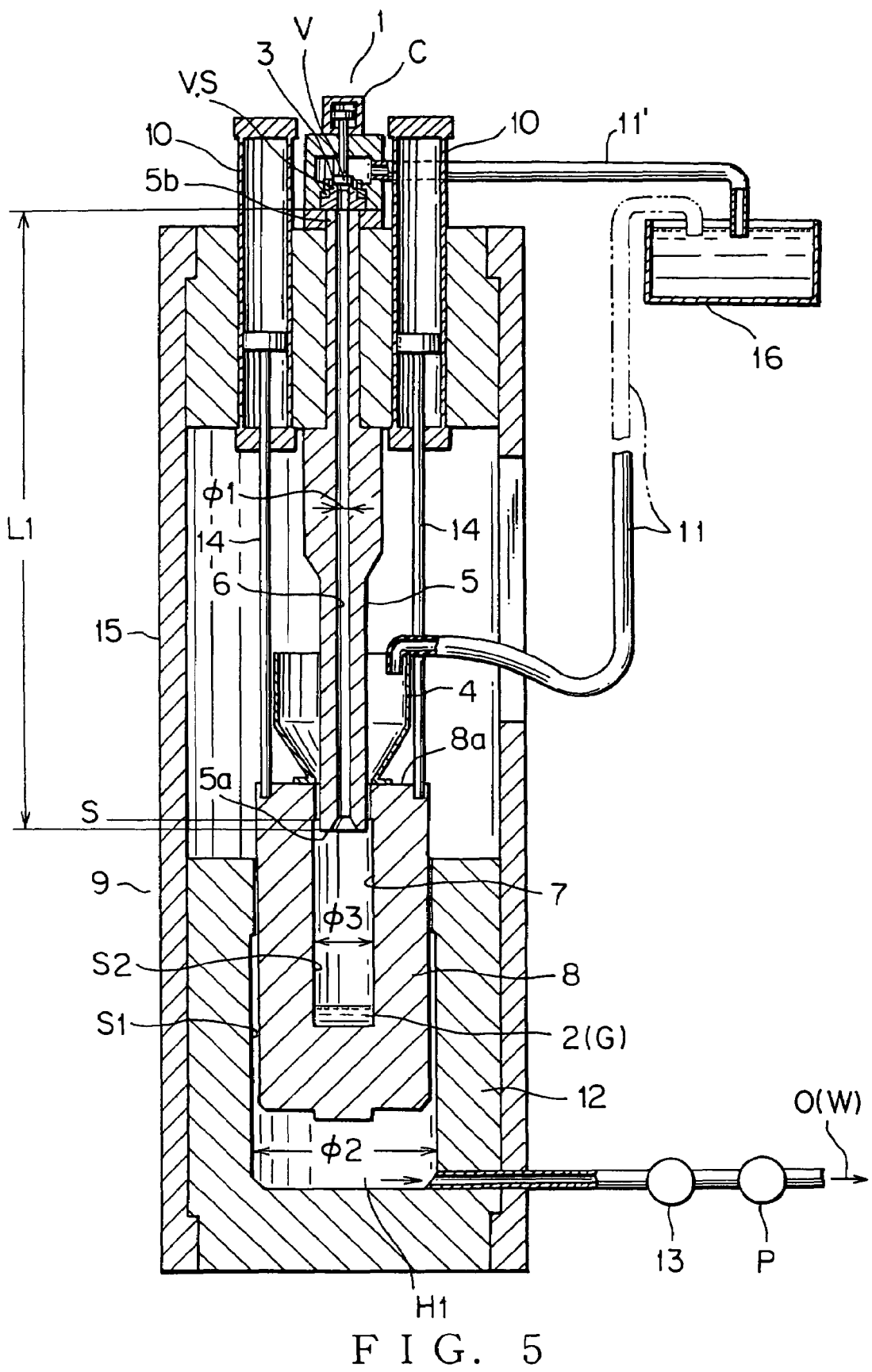
F I G. 5

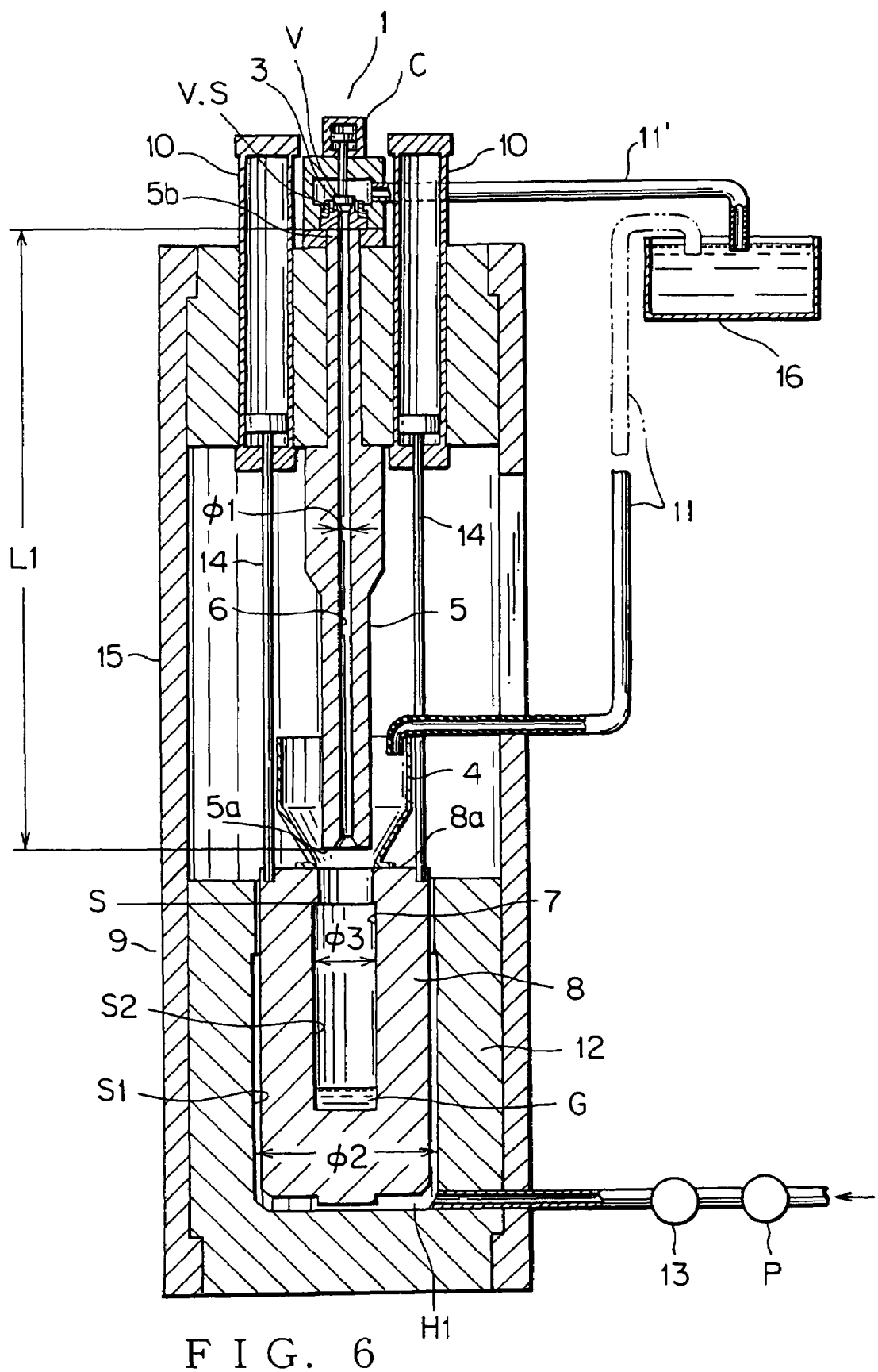
F I G. 6

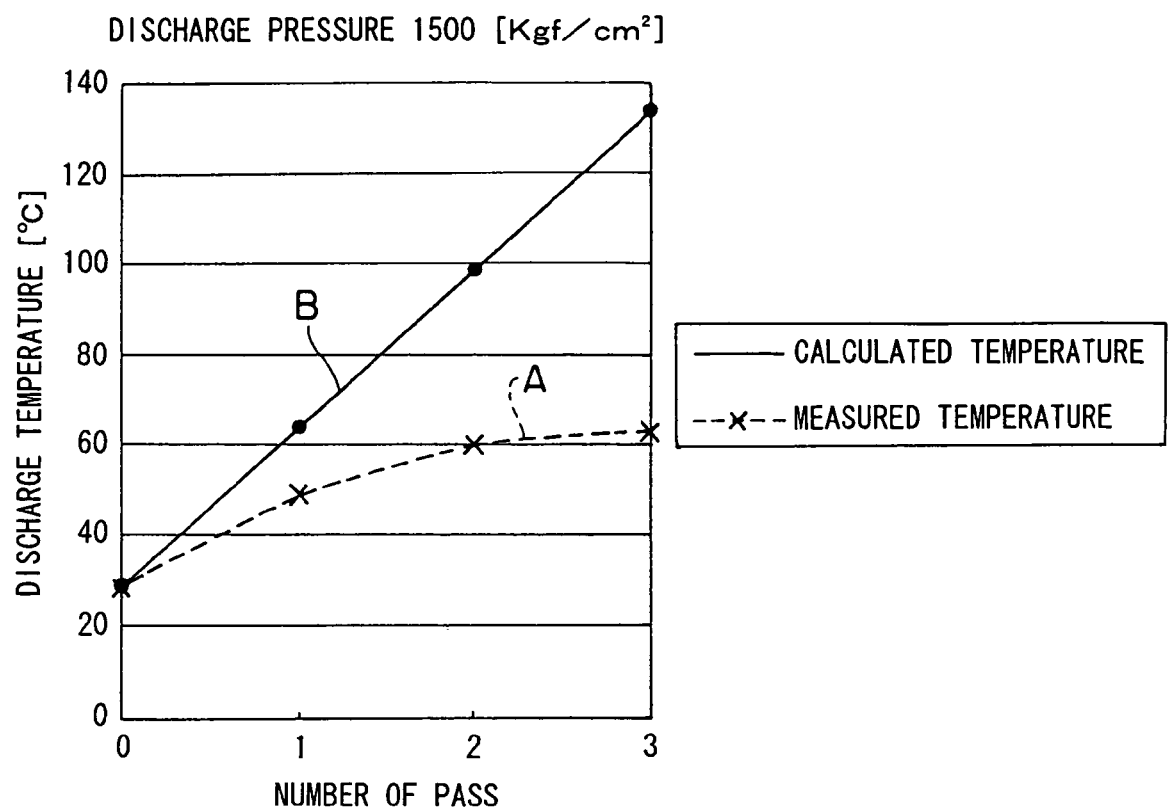
F I G. 1 4

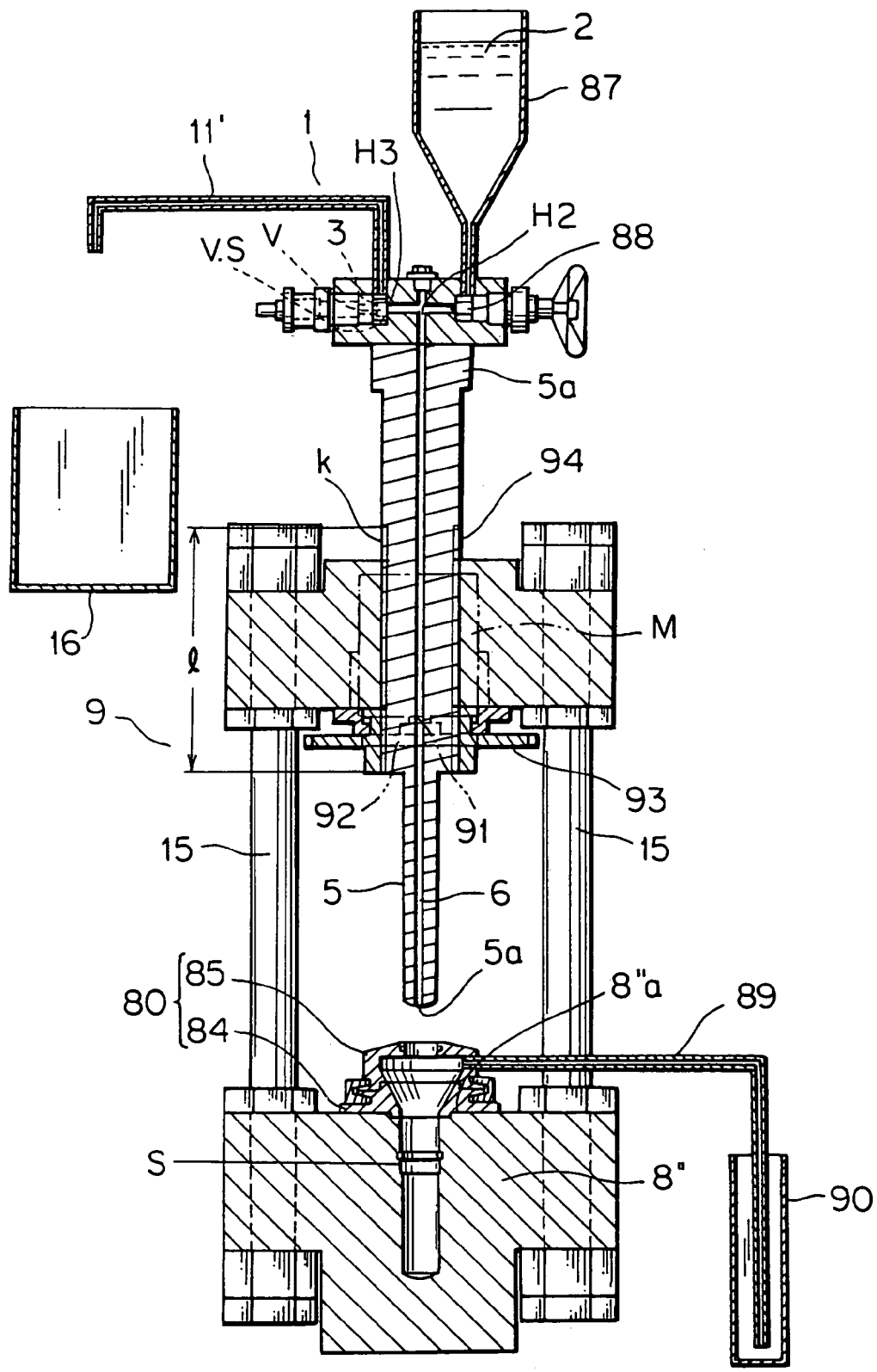
F I G. 4 5

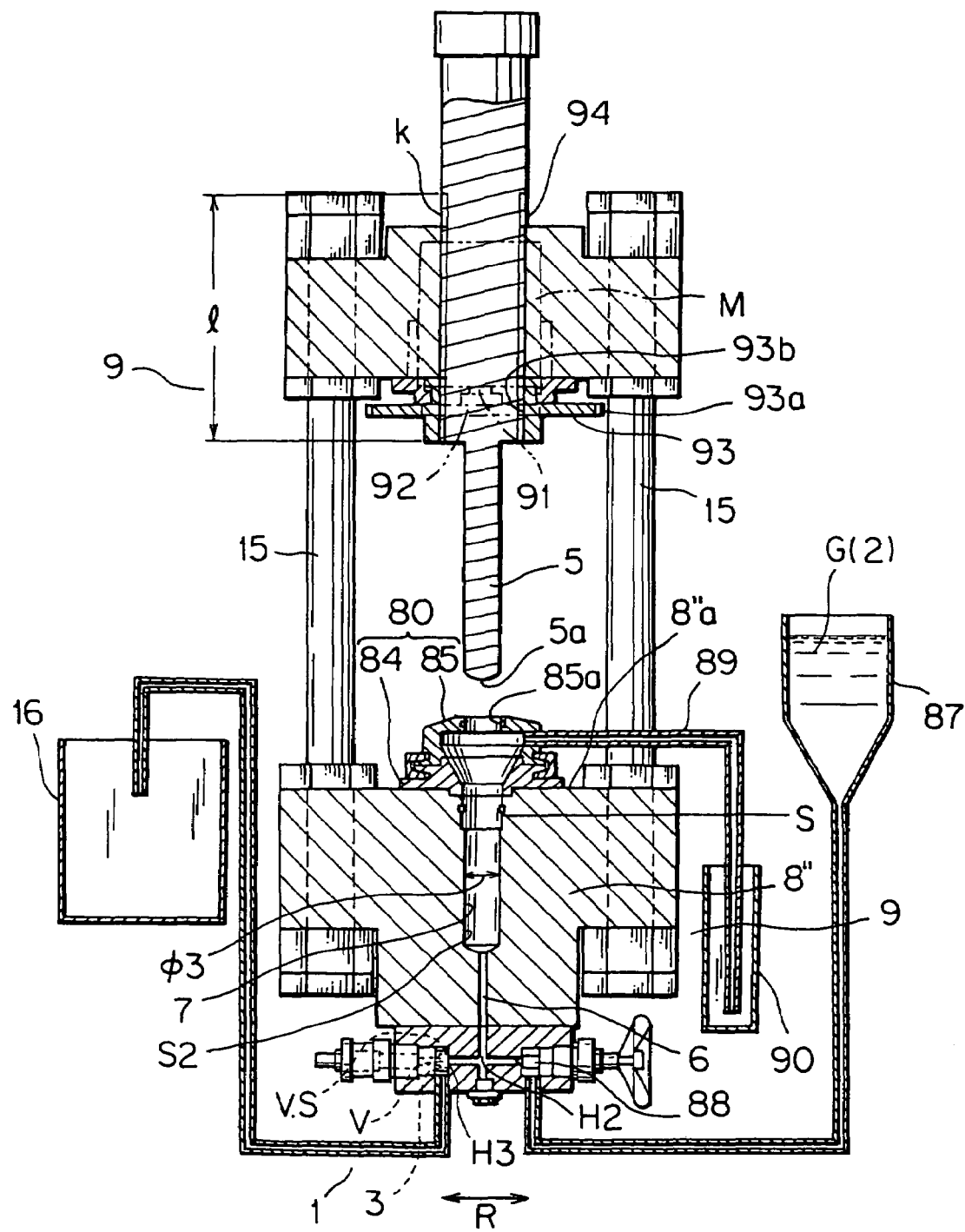
F I G. 47

HIGH PRESSURE HOMOGENIZING APPARATUS AND METHOD THEREOF

BACKGROUND OF THE INVENTION

1. Field of the Invention

The present invention relates to a dispersion and an emulsification of suspensions containing fine solid raw materials in food, chemical products, medical products, various resins and also of suspension containing fibrous cellulose in paper manufacturing field. The present invention relates to a fine division of raw materials, such as crushing cell membranes of fungi of coliform bacillus and yeast cells contained in liquid. The present invention provides a high efficiency of dispersion and emulsification of solids in the suspensions, and a high efficiency crushing of the cell membranes. The present invention has a high process capacity and a possibility for automation. In the present invention, valves are not damaged so that a maintenance and control become easy.

2. Description of the Related Art

In a conventional high pressure homogenizing apparatus in the paper manufacturing field (JP,S60-19921,A), a suspension containing fibrous cellulose is passed through a small orifice with a high pressure and the fibrous cellulose is finely divided.

The conventional apparatus employs a reciprocating movement of a piston in a cylinder with a motor to flow the suspension of the fibrous cellulose through the small orifice with high pressure. Since the fibrous cellulose is viscous, the conventional apparatus can not flow the fibrous cellulose quickly through the orifice, causing a low productivity of fine division.

Furthermore, the fibrous cellulose sticks to an inlet and outlet valve seats of the piston, causing a trouble in an open and close of the valve, a leakage of the raw material under the high pressure, and accordingly the low productivity.

Since the conventional apparatus is operated under high pressure, the piston and the inlet and outlet valves wear rapidly and are damaged easily. For this reason, the maintenance and control of the apparatus is required and cause an increasing cost.

SUMMARY OF THE INVENTION

An object of the present invention is to provide a high pressure homogenizing apparatus and method of dispersing and emulsifying a solid material contained in a suspension or of crushing cell membranes. The apparatus has a simple structure and high processing capacity under high pressure. The apparatus can be automated and has no valves damaged so that the parts of the apparatus become long-life and has easy maintenance and control.

According to a first aspect of the present invention, a high pressure homogenizing apparatus includes a high pressure homogenizing device having a small diameter orifice for passing a suspension containing fine solid materials, fibrous celluloses, or cells at high pressure and high speed, a raw material receiving passage connected to the high pressure homogenizing device, a processing piston, a receiver opposed to the processing piston, a processing recess disposed in the receiver and for inserting a front end of the processing piston with a pressure intensifier, whereby the receiver and/or the processing piston is moved relatively with the pressure intensifier and a volume inside the processing recess is compressed so that a desired amount of the suspension containing a raw material is pressurized and led into the raw material receiving passage to be finely divided.

According to a second aspect of the present invention, the processing recess is disposed inside a booster piston or the receiver, which moves relatively to the processing piston fixed to a frame, of the pressure intensifier.

According to a third aspect of the present invention, the processing recess is disposed inside the receiver or a movable cylinder, which moves relatively to the processing piston fixed to the frame, of the pressure intensifier.

According to a fourth aspect of the present invention, the processing recess is disposed inside the cylinder as the receiver moving relatively to the processing piston connected with a booster piston of the pressure intensifier disposed movably to the frame.

According to a fifth aspect of the present invention, the processing recess is disposed inside the movable cylinder as the receiver moving relatively to the processing piston connected to the booster piston of the pressure intensifier disposed movably to the frame.

According to a sixth aspect of the present invention, the raw material receiving passage is disposed inside the processing piston in a longitudinal direction thereof.

According to a seventh aspect of the present invention, the raw material receiving passage is communicated between the processing recess and the high pressure homogenizing device and disposed at in a radial direction of the processing recess.

According to an eighth aspect of the present invention, the raw material receiving passage is connected at one end to a bushing having a T or L-shaped section disposed at a lower position of the processing recess.

According to a ninth aspect of the present invention, the processing recess has a sliding valve therein at a lower position of the processing recess and the sliding valve opens and closes the raw material receiving passage with a spring responding to an internal pressure change.

According to a tenth aspect of the present invention, the suspension containing the raw material is led into the raw material receiving passage when the processing piston passes through a watertight position and the processing recess becomes watertight.

According to an eleventh aspect of the present invention, when the processing piston passes through the watertight position and the suspension is filled in the processing recess and raw material receiving passage to be watertight, the suspension in the raw material receiving passage is pressurized.

According to a twelfth aspect of the present invention, a hopper supplying the suspension is disposed at an opening of the processing recess and the processing piston is inserted into the processing recess through the hopper to be watertight.

According to a thirteenth aspect of the present invention, the booster piston, the processing piston, or the movable cylinder is returned to an initial position by a cylinder driven with the pressure intensifier after the suspension is led into the raw material receiving passage at high pressure.

According to a fourteenth aspect of the present invention, the pressure intensifier has a booster cylinder for oil or water to flow into and the booster piston disposed slidably inside the booster cylinder and having the processing recess at one end in a secondary path for inserting the front end of the processing piston.

According to a fifteenth aspect of the present invention, the pressure intensifier includes the booster cylinder for oil or water to flow into, the booster piston as the processing piston disposed slidably in the booster cylinder, and the cylinder having the processing recess at the one end for inserting the front end of the processing piston.

According to a sixteenth aspect of the present invention, when the pressure intensifier is returned to the initial position after finely dividing the raw material, a relative movement of the receiver and/or the processing piston increases the volume inside the processing recess so that the suspension is led into the processing recess and filled over the watertight position in the processing recess.

According to a seventeenth aspect of the present invention, the processing piston is moved manually to the initial position, at which the suspension is filled over the watertight position, by a handle disposed around the processing piston.

According to an eighteenth aspect of the present invention, the processing piston is moved with a motor, a gear group having a drive gear attached to a shaft of the motor and a driven gear engaging with the drive gear and a screw disposed at an outer wall of the processing piston, a key groove disposed at the outer wall of the processing piston intersecting with the screw in the axial direction, and a key being locked into the key groove.

According to a nineteenth aspect of the present invention, a relative moving stroke of the receiver and/or the processing piston at an automatic operation is adjusted with a stroke controller.

According to a twentieth aspect of the present invention, a detachable cover is disposed at an upper face of the receiver to cover the processing recess and slidably passed through by the processing piston.

According to a twenty-first aspect of the present invention, the cover includes a fixing plate attached to an upper portion of the receiver having the processing recess, an annular cover main body attached to an upper face of the fixing plate and having a first locking edge at an outer circumference thereof, an upper cover having a through-hole for inserting the processing piston and a second locking edge to be faced with the first locking edge, and collars separated in two parts to hold the first and second locking edges. The upper cover is detachable to the cover main body with the collars.

According to a twenty-second aspect of the present invention, the high pressure homogenizing device has a valve moving along an axial direction thereof driven with oil pressure or air cylinder for pressing variably a valve seat at the orifice to adjust an internal pressure to finely divide the raw material.

According to a twenty-third aspect of the present invention, the high pressure to finely divide the solid material, fibrous cellulose, or cells contained in the suspension in the high pressure homogenizing device is determined by converting a low pressure of oil or water detected at a primary path inside the booster cylinder of the pressure intensifier.

According to a twenty-fourth aspect of the present invention, a plurality of high pressure homogenizing devices are connected to the other end of the secondary path of the raw material receiving passage.

According to a twenty-fifth aspect of the present invention, the internal pressure of the high pressure homogenizing device to finely divide the raw material of the solid material, fibrous cellulose, or cells is detected from the low pressure of oil or water led into the booster cylinder of the pressure intensifier, and the booster piston and the cylinder are automatically controlled and operated based on the detected signals.

According to a twenty-sixth aspect of the present invention, a method of high pressure homogenizing includes the steps of supplying a suspension containing a raw material of a fine solid material, fibrous cellulose, or cells to a processing recess for inserting a front end of a processing piston with a pressure intensifier, driving the pressure intensifier for moving a receiver and/or the processing piston relatively each other, decreasing a volume inside the processing recess, and leading the desired amount of the suspension into a raw material receiving passage disposed inside the processing piston along a longitudinal direction or disposed in a radial direction of the processing recess and connected with the processing recess and a high pressure homogenizing device for finely dividing the suspension, increasing the pressure of the suspension inside the raw material receiving passage, passing the suspension through an orifice of the high pressure homogenizing device at high speed, and finely dividing the raw material into a dispersion, an emulsification, or a crush of the cell membranes.

According to a twenty-seventh aspect of the present invention, the method of high pressure homogenizing includes the steps of supplying the suspension containing the raw material of the fine solid, fibrous cellulose, or cells to a hopper, inserting the front end of the processing piston through the hopper into the processing recess disposed inside the receiver and opposed to the processing piston, passing the processing piston through a watertight position in the processing recess to increase the pressure inside the processing recess at the watertight state, driving the pressure intensifier for moving the receiver and/or the processing piston relatively each other, decreasing a volume inside the processing recess, and leading the desired amount of the suspension into the raw material receiving passage disposed inside the processing piston along the longitudinal direction or disposed in the radial direction of the processing recess and connected with the processing recess and the high pressure homogenizing device for finely dividing the suspension, increasing the pressure of the suspension inside the raw material receiving passage, passing the suspension through the orifice of the high pressure homogenizing device at high speed, and finely dividing the raw material into the dispersion, emulsification, or the crush of the cell membranes.

According to a twenty-eighth aspect of the present invention, the method of high pressure homogenizing includes the steps of supplying the suspension containing the raw material of the fine solid material, fibrous cellulose, or cells over the watertight position in the processing recess disposed inside the receiver with the processing piston as a preliminary step, inserting the front end of the processing piston into the processing recess, passing the processing piston through the watertight position in the processing recess to increase the pressure inside the processing recess at the watertight state, driving the pressure intensifier for moving the receiver and/or the processing piston relatively each other, decreasing the volume inside the processing recess, and leading the desired amount of the suspension into the raw material receiving passage disposed inside the processing piston along the longitudinal direction or disposed in the radial direction of the processing recess and connected with the processing recess and the high pressure homogenizing device for finely dividing the suspension, increasing the pressure of the suspension inside the raw material receiving passage, passing the suspension through the orifice of the high pressure homogenizing device at high speed, and finely dividing the raw material into the dispersion, the emulsification, or the crush of the cell membranes.

According to a twenty-ninth aspect of the present invention, the method of high pressure homogenizing includes the steps of returning the pressure intensifier to the initial position, increasing the volume inside the processing recess with the relative movement of the receiver and/or the processing piston, and leading the suspension into the processing recess to fill over the watertight position.

BRIEF DESCRIPTION OF THE DRAWINGS

FIG. 5 is a sectional view showing that the booster piston is moved to the initial position by opening a homogenizing valve of the high pressure homogenizing device and leading an air;

FIG. 6 is a sectional view showing that one cycle of the fine division is finished;

FIG. 14 is a graph of the measured and calculated discharge temperatures when subdivided three times continuously at the orifice discharge pressure of 1,500 Kg/cm² (147,000 KPa) of the high pressure homogenizing device;

FIG. 45 is a sectional view of a sixteenth embodiment of a homogenizing apparatus of the present invention;

FIG. 47 is a sectional view of a seventeenth embodiment of a homogenizing apparatus of the present invention;

DETAILED DESCRIPTION OF THE PREFERRED EMBODIMENTS

Figure 1:
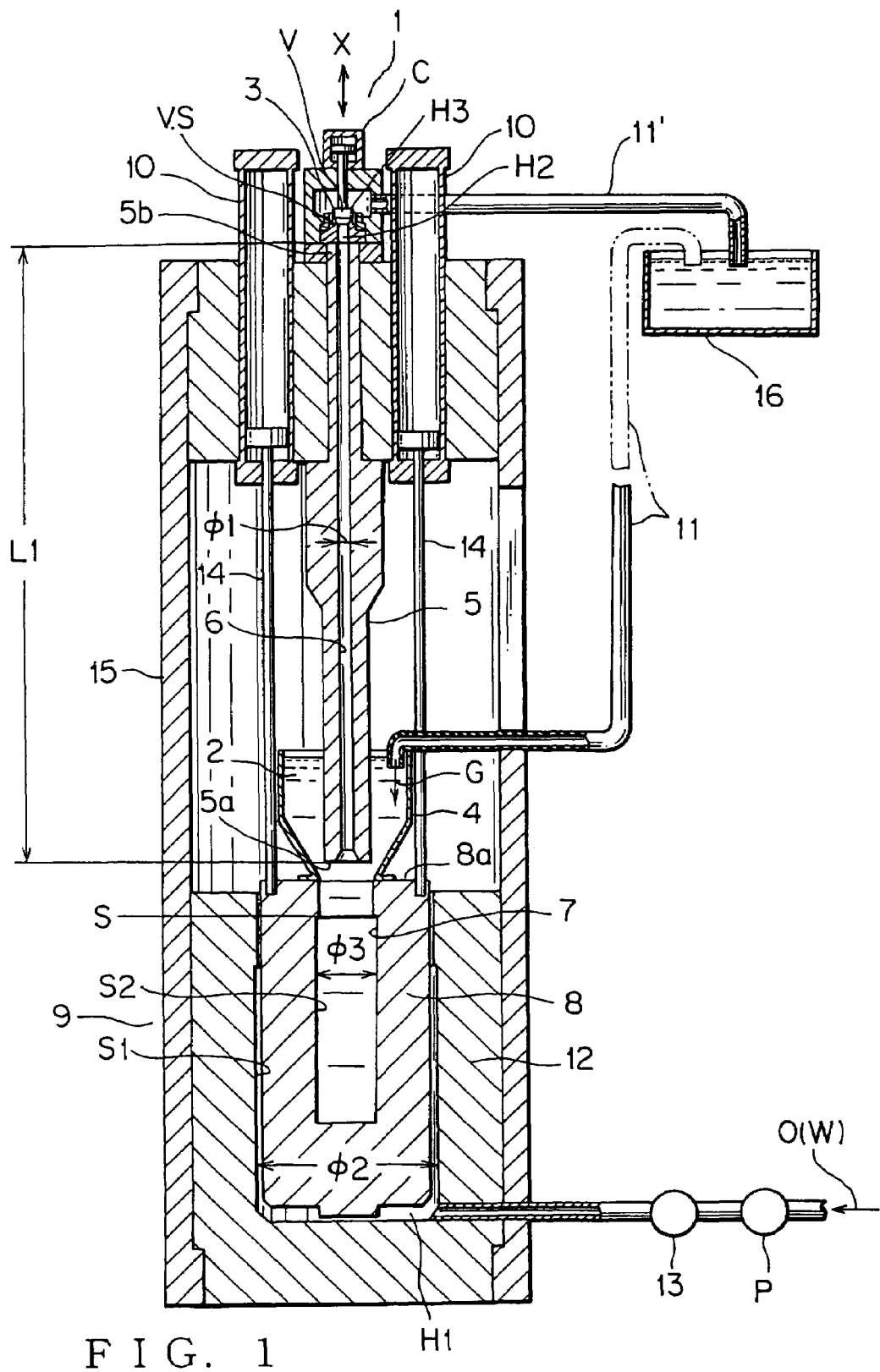
FIG. 1 is a sectional view of a first embodiment of a high pressure homogenizing apparatus of the present invention showing a suspension containing a raw material is supplied.

A high pressure homogenizing apparatus of the present invention passes a suspension 2 containing a raw material G such as fine solid materials, fibrous cellulose, and cell membranes through a small orifice 3 disposed in a high pressure homogenizing device 1 to disperse and emulsify the raw material G or crush, that is, subdivide the cell membranes under high pressure. The high pressure homogenizing apparatus has a raw material receiving passage 6, a processing piston 5, a receiver opposed to the processing piston 5, and a processing recess 7 to receive a front end (one end) 5a of the processing piston 5 by means of a pressure intensifier 9. When the pressure intensifier 9 is driven, the receiver and/or the processing piston 5 moves relatively and the suspension 2 flows into the raw material receiving passage 6 with a desired amount to be processed by a change of volume inside the processing recess 7. The solid materials, fibrous cellulose, and cells in the suspension 2 are finely divided at the orifice 3 of the high pressure homogenizing device 1.

As shown in FIG. 1, the high pressure homogenizing apparatus includes a hopper 4 disposed at an opening of the processing recess 7 to receive the suspension 2, the processing piston 5 having the raw material receiving passage 6 inside along the axial direction, the front end 5a being movable in the hopper 4 relatively and the other end 5b being connected to the high pressure homogenizing device 1, a booster piston 8 as the receiver having the processing recess 7 disposed at one end 8a, the pressure intensifier 9 to move the booster piston 8 up and down with respect to the processing piston 5 with increased pressure, and cylinders 10 to reciprocate the booster piston 8. The relative movement of the processing piston 5 and the processing recess 7 can change the volume inside the processing recess 7. The fine solid materials, fibrous cellulose, or cells in the suspension 2 corresponding to the volume change in the processing recess 7 flow into the raw material receiving passage 6 and are finely divided at the high pressure homogenizing device 1.

As shown in FIG. 1, the high pressure homogenizing device 1 has a homogenizing valve V which drives straight in the axial direction X with a hydraulic cylinder C or air cylinder, and a valve seat V.S to form the orifice 3. The homogenizing valve V contacts with the valve seat V.S in order to adjust an internal pressure for fine dividing process of the raw material G.

The raw materials G are considered as the followings. In foods, the raw materials G are solid materials such as preparations and fibrous cellulose. They are contained in the suspensions 2 of finished or semi-finished products of foods such as tomato ketchup, oil, dairy products of butter and yogurts, soft drinks, fruit juices, soups, and baby foods in order for separation prevention, long-term stability, flavor, and swallowing. In chemical products or cosmetics, the raw materials are solid materials such as pigments, magnetic powders, or minerals contained in the suspensions 2 or emulsions of finished or semi-finished products thereof. In medical products, they are solid materials such as minerals and crude drugs contained in the suspensions 2 or emulsions of finished or semi-finished products thereof. In glassware, they are fine solid materials such as pigments and minerals contained in liquid glasses. In synthetic resin industries, they are pigments, minerals, elasticizer, and reinforced fibers contained in the suspensions 2 or emulsions of finished or semi-finished products thereof. In paper manufacturing field, they are solid materials such as fibrous cellulose contained in the suspensions 2 during manufacturing. In pathology laboratories, they are cells of fungi such as coliform bacillus and yeast cells contained in the suspensions 2.

The hopper 4 is a container and the raw material G is supplied to the hopper 4 through a flexible pipe 11, one end of which is connected to the hopper 4.

A section area $\phi 1$ and a length L1 of the raw material receiving passage 6 are set so as that the high pressure homogenizing device 1 can achieve the best process of fine division of the raw material G.

The booster piston 8 of the pressure intensifier 9 is moved upwardly by pressure. When the processing piston 5 passes through a watertight position S of the processing recess 7 disposed at the end 8a of the booster piston 8, the suspension 2 supplied to the hopper 4 is forced to flow in the raw material receiving passage 6 and a desired amount thereof is received.

The pressure intensifier 9 has a booster cylinder 12 and the booster piston 8. Oil O or water W flows into the booster cylinder 12. The booster piston 8 is slidable to the booster cylinder 12 and has the processing recess 7 at the end 8a into which the front end 5a of the processing piston 5 is inserted for the reciprocating movement.

When a low pressure oil O or water W is supplied to the booster cylinder 12 of the pressure intensifier 9 with a pump P, the booster piston 8 is moved toward the processing piston 5. The front end (the one end 5a) of the processing piston 5 is inserted into the processing recess 7 disposed at one end 8a through the hopper 4 and the processing recess 7 is pressurized. The suspension 2 containing the raw material G in the hopper 4 is led into the raw material receiving passage 6 in the processing piston 5.

In the embodiment shown in FIG. 1, the booster cylinder 12 has an inner diameter $\phi 2$ of about 340 mm at a cross section S1 and the processing recess 7 has an inner diameter $\phi 3$ of about 110 mm at a cross section S2.

The booster cylinder 12 has initially a low internal pressure H1 of 100 Kg/cm$^2$ (9,800 KPa) when the oil O or water W flows into the booster cylinder 12. When the processing piston 5 enters into the processing recess 7, the internal pressure of the raw material receiving passage 6 reaches to a high pressure H2 of 955 Kg/cm$^2$ (93,590 KPa). The internal pressure of the raw material receiving passage 6 can be reached to the maximum pressure H2 of 2,300 Kg/cm$^2$ (225,400 KPa) by adjusting the inner diameter φ2 of the booster cylinder 12 and the inner diameter φ3 of the processing recess 7, and selecting the pump P of a desired power.

A high pressure H3 at the high pressure homogenizing device 1, which disperses and emulsifies the solid materials or fibrous cellulose and crushes the cells for finely dividing the raw material G in the suspension 2, is estimated from the primary low pressure H1, which is induced by the oil O or water W flowing into the booster cylinder 12, measured at an oil pressure indicator 13 and detected by a sensor (not shown).

The cylinders 10 have piston rods 14 connected to the booster piston 8 in order to increase the internal pressure of the raw material receiving passage 8 to the high pressure H2 by moving the rods 14 up and down.

The high pressure homogenizing device 1 is attached to an upper portion of a frame 15 as shown in FIG. 1. The cylinders 10 are attached to both sides of the upper portion of the frame 15. The processing piston 5 is arranged in the center of the upper portion inside the frame 15 and the booster cylinder 12 is arranged in a lower portion of the frame 15.

A discharge pipe 11' is connected to the high pressure homogenizing device 1 and is utilized to discharge the subdivided raw material G to a container 16 as needed.

The structure of the high pressure homogenizing device 1 is explained in the above. A process thereof for dispersing or emulsifying the raw materials of the solid materials or fibrous cellulose contained in the suspension and for crushing to finely divide the cell membranes is explained.

The raw materials G are considered as the followings. In foods, the raw materials G are solid materials such as preparations and fibrous cellulose. They are contained in the suspensions 2 of finished or semi-finished products of foods such as tomato ketchup, oil, dairy products of butter and yogurts, soft drinks, fruit juices, soups, and baby foods in order for separation prevention, long-term stability, flavor, and swallowing. In chemical products or cosmetics, the raw materials are solid materials such as pigments, magnetic powders, or minerals contained in the suspensions 2 or emulsions of finished or semi-finished products thereof. In medical products, they are solid materials such as minerals and crude drugs contained in the suspensions 2 or emulsions of finished or semi-finished products thereof. In glassware, they are fine solid materials such as pigments and minerals contained in liquid glasses. In synthetic resin industries, they are pigments, minerals, elasticizer, and reinforced fibers contained in the suspensions 2 or emulsions of finished or semi-finished products thereof. In paper manufacturing field, they are solid materials such as fibrous cellulose contained in the suspensions 2 during manufacturing. In pathology laboratories, they are cells of fungi such as coliform bacillus and yeast cells contained in the suspensions 2.

In order to finely divide the raw material G of the solid materials, fibrous cellulose, or cells of fungi contained in the suspension 2, the suspension 2 is supplied to the hopper 4 through the flexible pipe 11. The suspension 2 is also supplied to the processing recess 7 (refer to FIG. 1).

Figure 2:
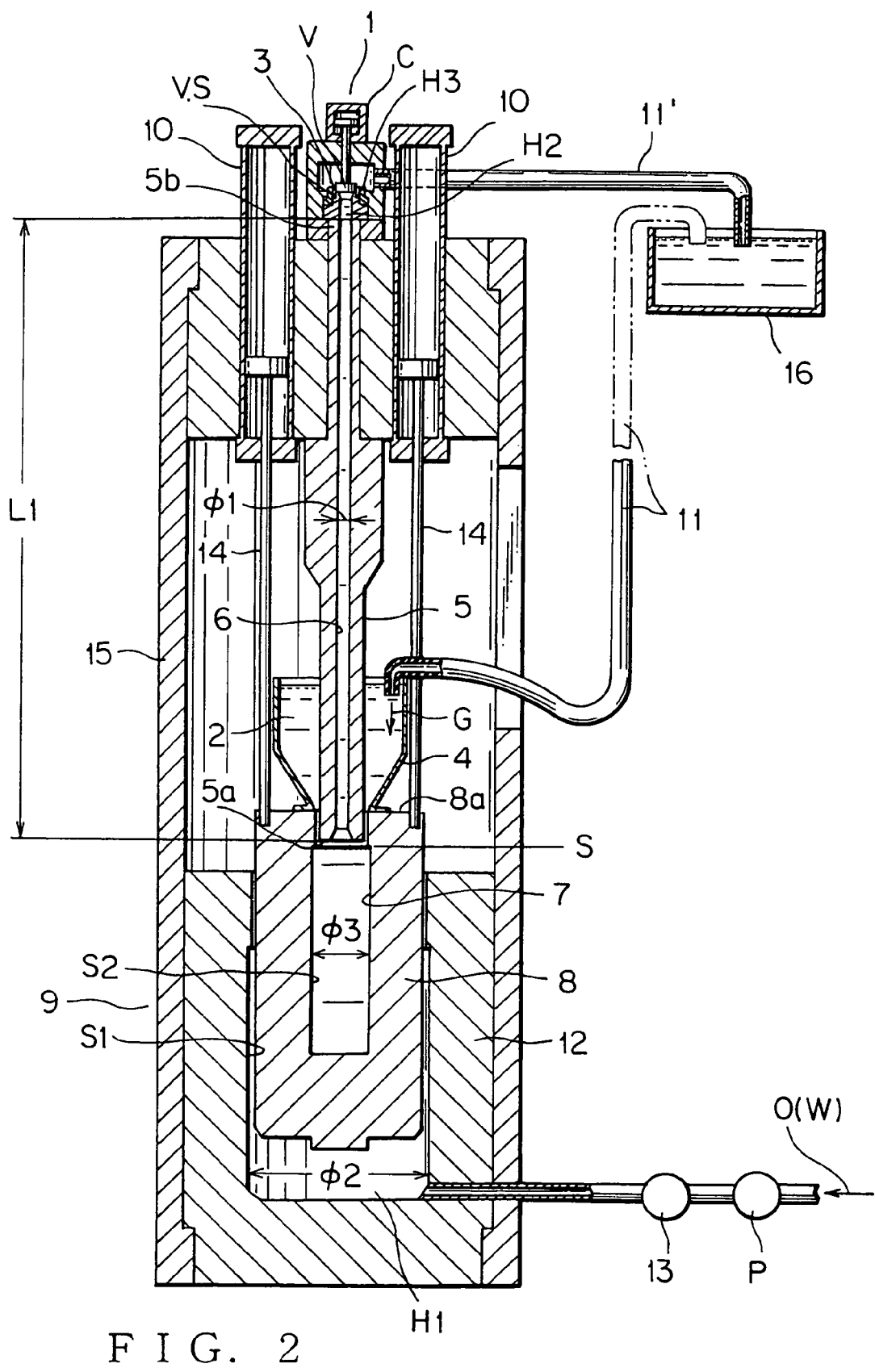
FIG. 2 is a sectional view showing that a processing piston passes through a watertight position and pressurizes a processing recess.
Figure 3:
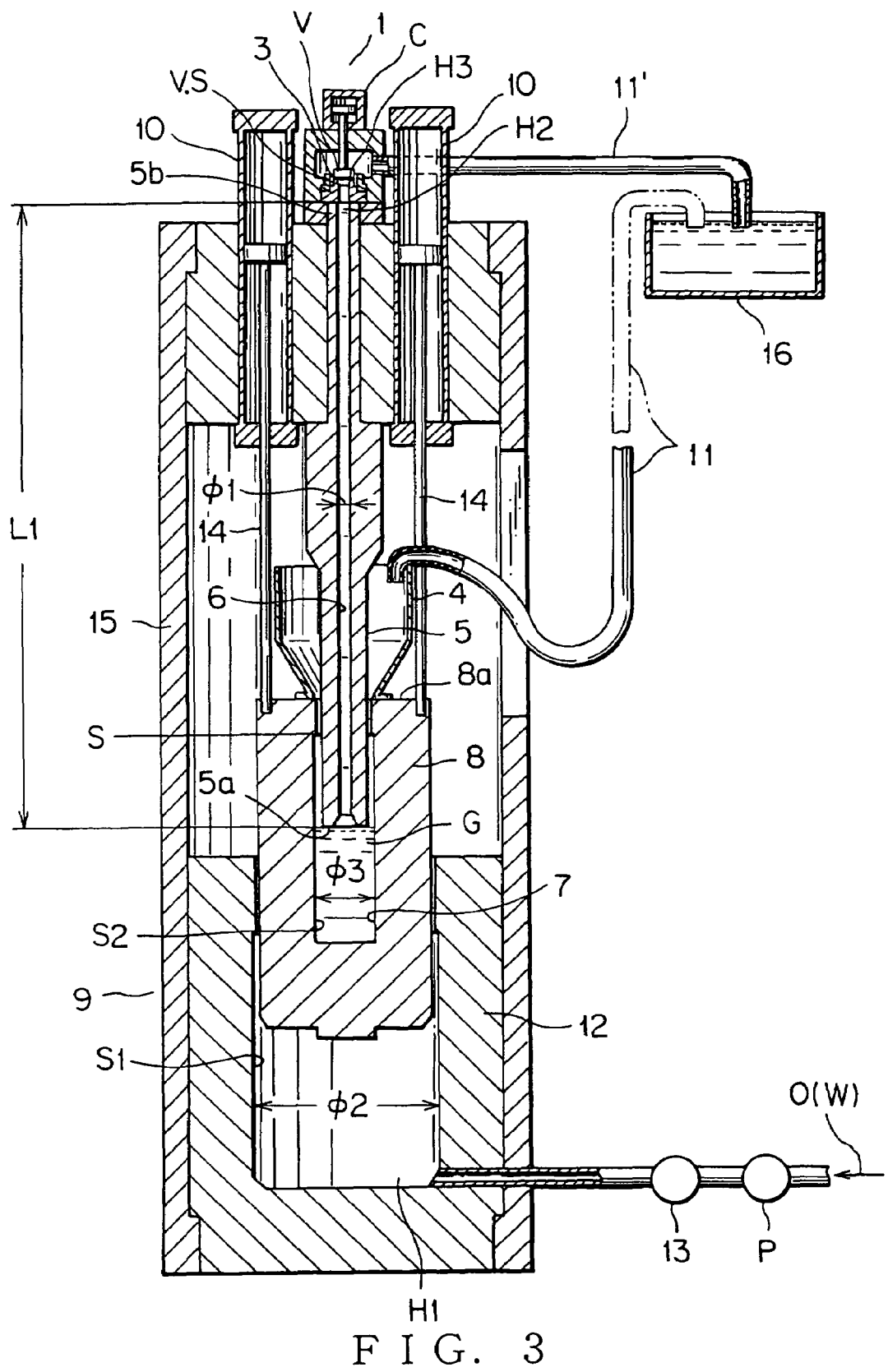
FIG. 3 is a sectional view showing that the suspension is led into a raw material receiving passage in the processing piston, pressurized to a high pressure, and subdivided at a high pressure homogenizing device.
Figure 4:
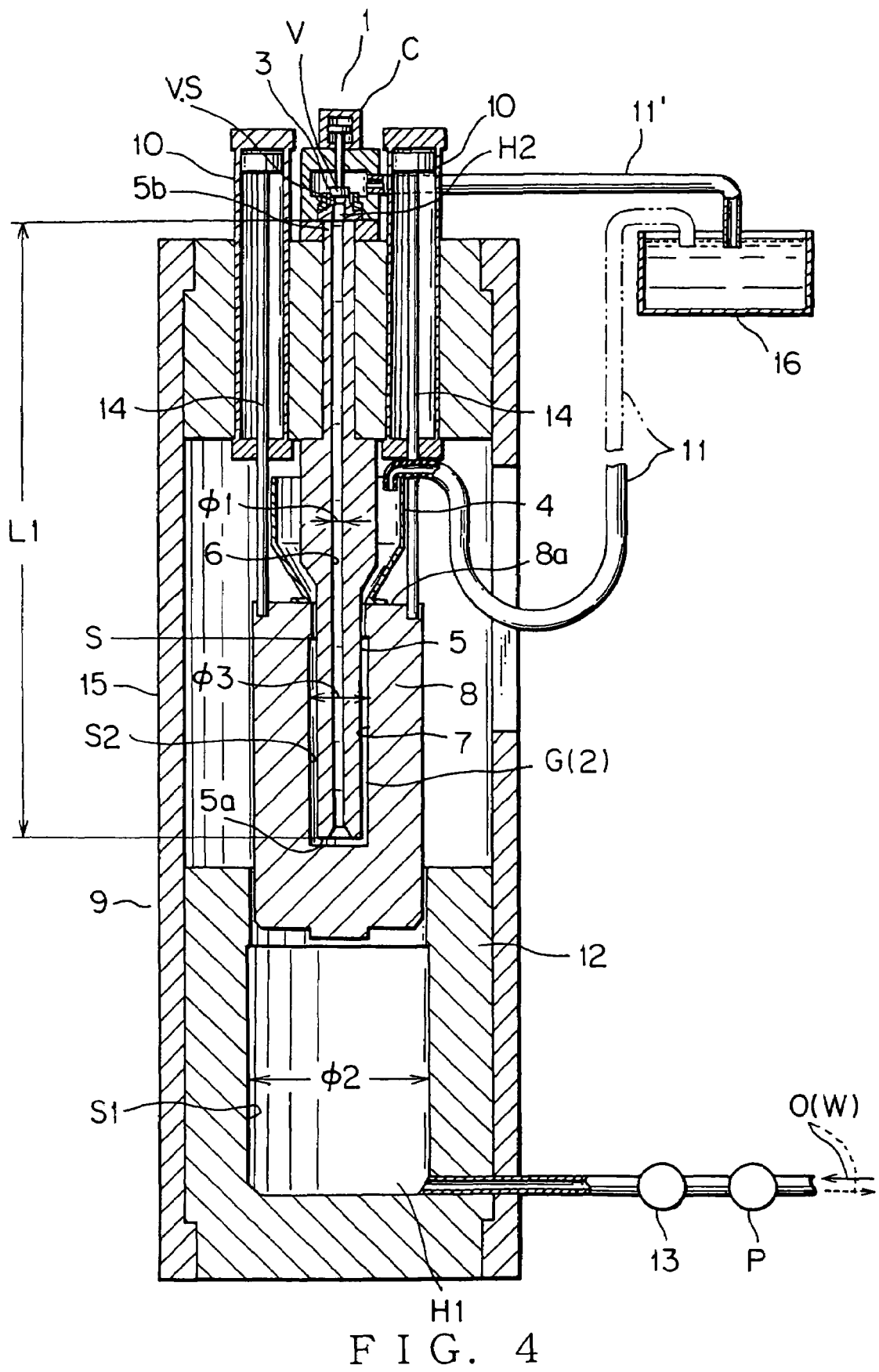
FIG. 4 is a sectional view showing that a booster piston is returned to an initial position by decreasing an internal pressure after finely dividing the raw material.

When the pressure intensifier 9 is driven and the booster piston 8 is moved upwardly, the front end 5a of the processing piston 5 enters into the processing recess 7 through the hopper 4 as seen in FIG. 2.

The movement of the booster piston 8 is driven by the low pressure H1 of the oil O or water W flowed into the booster cylinder 12.

After the processing piston 5 passes through the watertight position S of the processing recess 7, the inside of the processing recess 7 is pressurized.

The booster piston 8 moves toward the processing piston 5 until a sensor detects a stop. The compression of the volume inside the processing recess 7 presses and leads the suspension 2 into the raw material receiving passage 6 to the desired amount. The suspension 2 is further pressurized in the raw material receiving passage 6.

As described above, in the embodiment shown in FIG. 1, the booster cylinder 12 has the inner diameter φ2 of about 340 mm and the processing recess 7 has the inner diameter φ3 of about 110 mm. The booster cylinder 12 has initially the low internal pressure H1 of 100 Kg/cm$^2$ (9,800 KPa). When the processing piston 5 enters into the processing recess 7, the internal pressure of the raw material raw material receiving passage 6 reaches to the high pressure H2 of 955 Kg/cm$^2$ (93,590 KPa). The internal pressure of the raw material receiving passage 6 can be reached to the maximum pressure H2 of 2,300 Kg/cm$^2$ (225,400 KPa).

When the raw material G pressurized to H2 passes through the orifice 3 having a small gap between the valve seat V.S and the homogenizing valve V, wherein the valve seat V.S is connected to the end 5b of the processing piston 5 and is pressed by the homogenizing valve V, the raw material G flows in the orifice 3 very fast and causes cavitation therein. A shearing action is induced due to the high pressure difference when the cavity breaks. The raw material G is then discharged from the orifice 3 with high speed and clashed to a wall. As the result, the solid material or fibrous cellulose in the suspension 2 is dispersed or emulsified under the high pressure H3. The cells are torn apart and the cell membranes are crushed under the high pressure H3. The raw materials G are finely divided in this manner. As the raw material receiving passage 6 has higher pressure H2, the raw material G passes through the orifice 3 with higher speed and is clashed more strongly.

The value of the high pressure H2 for finely dividing the raw material G is converted from that of the oil pressure indicator 13 in the primary path where the oil O or water W forms the low pressure H1 in the booster cylinder 12 and the pressure is detected by the sensor (not shown). Measurement instruments such as the oil pressure indicator 13 endures the internal pressure and the measurement can be easily made without wear and failure.

Figure 7:
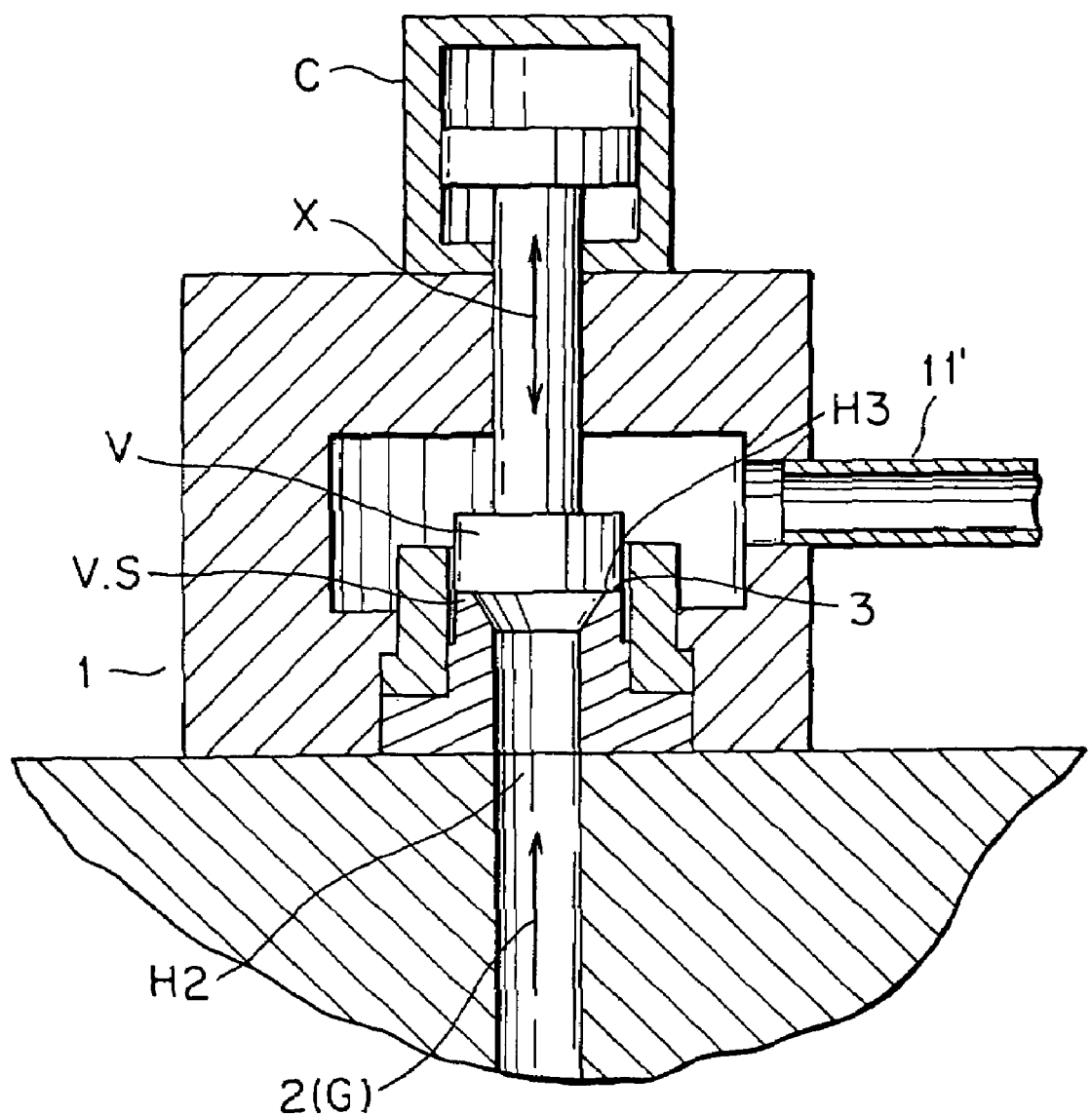
FIG. 7 is an expanded sectional view showing the high pressure homogenizing device of the first embodiment.

In the high pressure homogenizing device 1, the valve seat V.S forming the orifice 3 is pressed by the homogenizing valve V with the hydraulic or air cylinder C as shown in FIGS. 1 and 7 along the axial direction X in straight. The pressure to push the homogenizing valve V can be varied from the depressing pressure to high and very high pressures. The internal pressure in the vicinity of the orifice 3 is adjusted by the hydraulic cylinder C to finely divide the solid materials, fibrous cellulose, or cell membranes in the raw material G. The raw material G subdivided by the high pressure homogenizing device 1 is discharged into the container 16 through the discharge pipe 11'.

After finely dividing the raw material G, the oil O or water W in the booster cylinder 12 is discharged and the booster piston 8 is moved downwardly without resistance to the initial position with the cylinders 10 through the piston rods 14 as seen in FIG. 5. The booster piston 8 departs from the processing piston 5 attached to the frame 15 and the processing piston 5 is pulled out of the processing recess 7 so that the booster piston 8 returns to the initial position.

When the booster piston 8 is moved downwardly, the pressing of the homogenizing valve V to the valve seat V.S is released by driving the hydraulic cylinder C to introduce an air into the raw material receiving passage 6 fast and easily. The vacuum inside the raw material receiving passage 6 prevents the booster piston 8 from moving down easily (FIG. 5).

The booster piston 8 moves inside the booster cylinder 12 smoothly to the initial position (FIG. 6) and the position of the booster piston 8 is detected by the sensor (not shown).

The low pressure H1 of the primary path is measured by the oil pressure indicator 13 and detected by the sensor. A driving timing and stroke of the booster piston 8 is decided based on the detected signal. The detected signal controls the amount of the suspension 2 to be received in the raw material receiving passage 6 inside the processing piston 5 and also controls the high pressure H2 to the desired value to receive the raw material G in the raw material receiving passage 6.

From the detected signal of the low pressure H1 of the primary path, the hydraulic cylinder C to drive the homogenizing valve V for pressing the valve seat V.S, which forms the orifice 3 with the valve V, is controlled so as to decide the internal pressure for the raw material G, the pressing timing, and the pressing order, by adjusting the pressing pressure of the homogenizing valve V to the valve seat V.S. The detected signal can also control the timing for the booster piston 8 to return the initial position by means of the cylinders 10.

These controls are easily achieved with a computer program. The computer program can achieve the fine division process of the dispersion, emulsification, or crushing of the raw material G automatically. The automation process is carried out by the following processes. The suspension 2 is supplied to the hopper 4, the booster piston 8 is pressurized, the processing piston 5 is passed through the watertight position S of the processing recess 7, the suspension 2 is led into the raw material receiving passage 6 and pressurized to the high pressure H2 and subdivided once at the high pressure homogenizing device 1, and the suspension 2 containing the subdivided raw material are discharged to the container 16 and is supplied to the hopper 4 again through the pipe 11. The pressing force of the homogenizing valve V to the valve seat V.S is further increased by the hydraulic cylinder C for making finer fine division of the raw material G than before at the high pressure homogenizing device 1.

When this process is repeated, the raw material G is finely divided to a desired size easily and fast.

In the process of the first embodiment, the raw material G is pressurized to the high pressure H2 in the raw material receiving passage 6 right after the processing piston 5 passes through the watertight position S. Consequently, the desired amount of the raw material G can be led smoothly under the pressure or high pressure into the high pressure homogenizing device 1 even that the orifice 3 is small and the suspension 2 is viscous.

Since an entire operation is carried out continuously, the dispersion and emulsification of the solid materials and cellulose, or the crushing of the cell membranes is effectively made.

The high pressure homogenizing apparatus of the embodiment 1 was tested to verify the capacity and found it has a high performance.

As a first measurement, the suspension 2 of the fibrous cellulose contained in a piece of paper was subdivided with the high pressure homogenizing device 1 of the apparatus of the first embodiment and it was measured the relation between the discharge pressure of the orifice 3 and the fine division of the fibrous cellulose.

As shown in the micrograms of FIGS. 8 to 11, the fibrous cellulose in the suspension 2 becomes smaller as the discharge pressure at the fine division of the high pressure homogenizing device 1 increases.

A paper containing about 8 wt % water was cut into a size of about 4 mm*15 mm by a paper cutter (Type: NS-32C of Matsue Nakabayashi Co.).

The cut paper of about 43.5 g was admixed to a water of about 956.5 g. The admixture was stirred with a mixer (Type: MX-152S of Matsushita Denki Sangyo Co.) for one minute to break the fibrous cellulose into a small size. The suspension 2 of 4 Kg containing 4 wt % of the solid material (fibrous cellulose) dispersed uniformly in the water was prepared.

Figure 8:
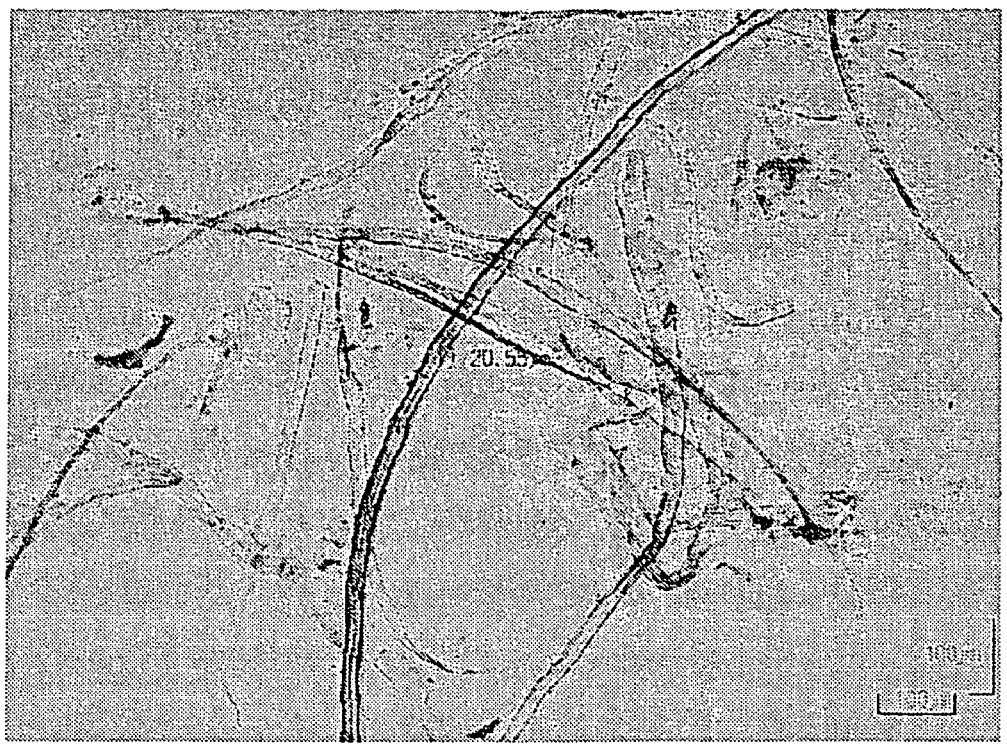
FIG. 8 is a microgram of the suspension after stirring with a mixer and before finely dividing.

FIG. 8 shows a microgram of the suspension 2 before finely dividing. The microgram was obtained by using a reflection/transmission microscope (Type: Eclipse ME 600L of Nikon Co.) with magnification of 10 to 50 and a digital camera unit (Type: DS-5M-L1 of Nikon Co.) attached to the microscope.

Figure 9:
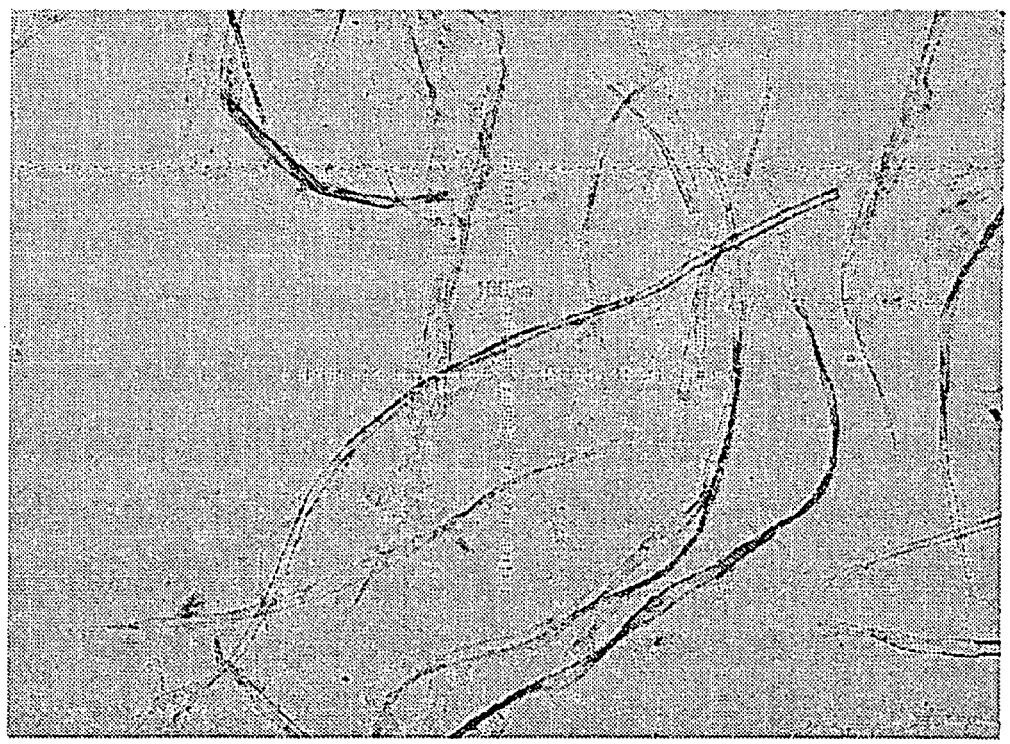
FIG. 9 is a microgram of the suspension subdivided three times continuously at an orifice discharge pressure of 500 Kg/cm² (49,000 KPa) of the high pressure homogenizing device.
Figure 10:
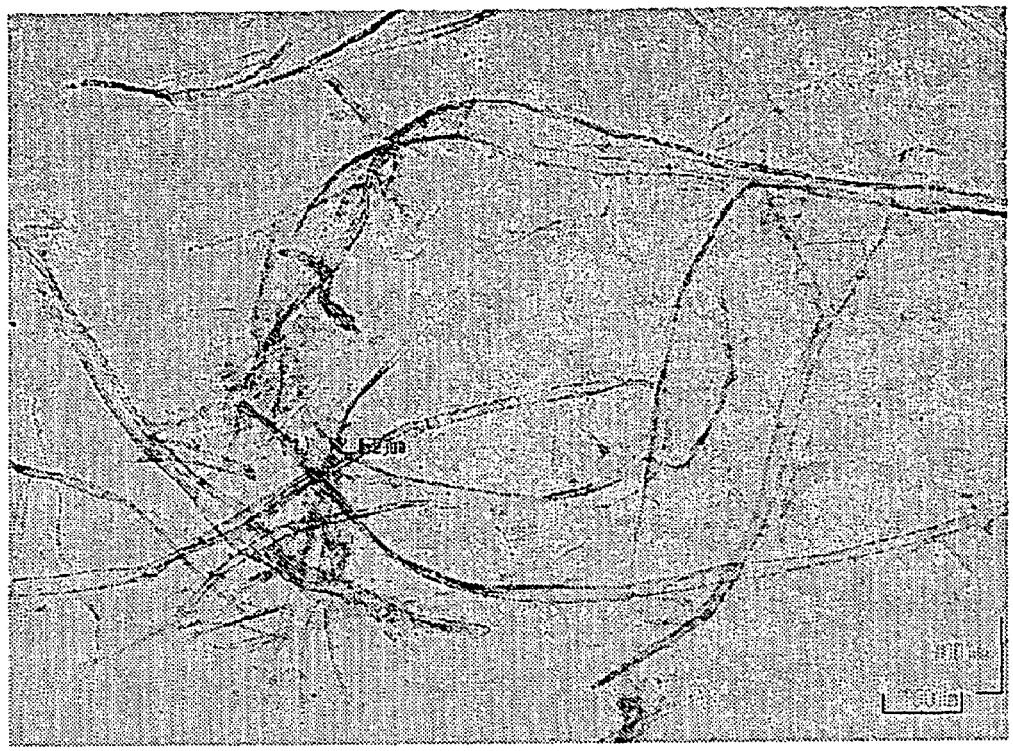
FIG. 10 is a microgram of the suspension subdivided three times continuously at the orifice discharge pressure of 1,000 Kg/cm² (98,000 KPa) of the high pressure homogenizing device.
Figure 11:
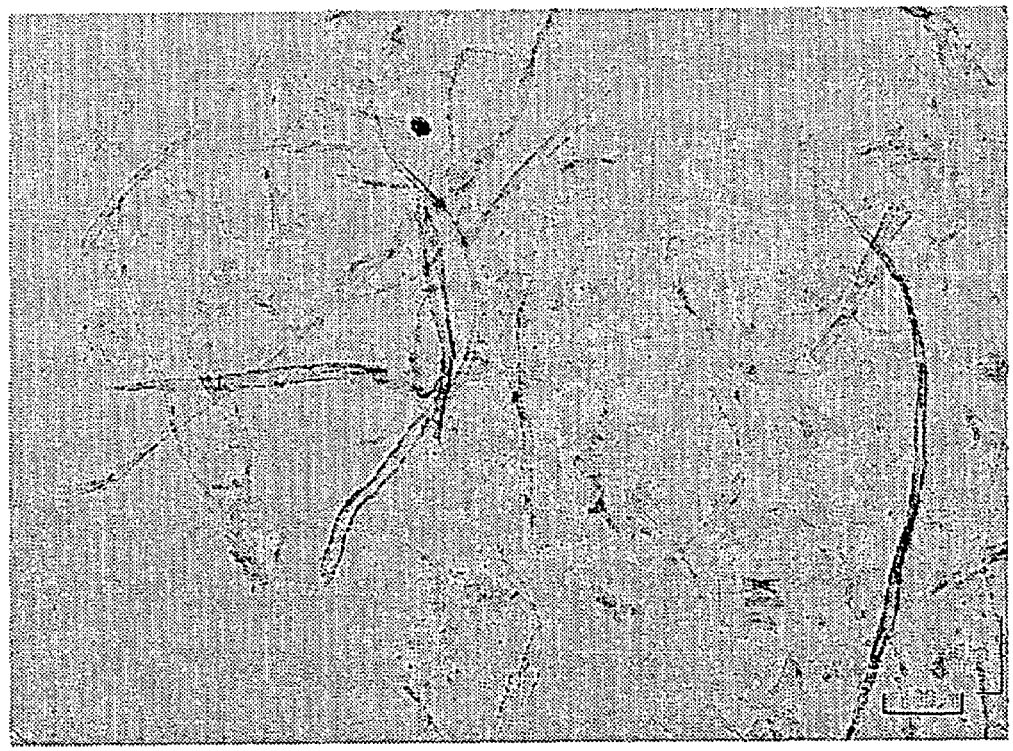
FIG. 11 is a microgram of the suspension subdivided three times continuously at the orifice discharge pressure of 1,500 Kg/cm² (147,000 KPa) of the high pressure homogenizing device.

FIG. 9 shows a microgram of the suspension 2 subdivided three times continuously at the orifice 3 with the discharge pressure of 500 Kg/cm$^2$ (49,000 KPa). FIGS. 10 and 11 show micrograms of the suspensions 2 subdivided three times continuously at the orifice 3 with the discharge pressures of 1,000 Kg/cm$^2$ (98,000 KPa) and 1,500 Kg/cm$^2$ (147,000 KPa) respectively.

As seen in FIG. 8, the fibrous cellulose having a section diameter of about 20 to 25 μm are uniformly dispersed in the suspension 2 before finely dividing.

In FIG. 9, micro fibrils are found around the fibrous cellulose of the diameter of about 15 μm and it shows the fine division of the raw material G at the discharge pressure of 500 Kg/cm$^2$.

FIG. 10 shows that the fibrous celluloses are broken into a shorter length and the micro fibrils are found much more around the fibrous celluloses of the diameter of about 7 to 14 μm and it shows further fine division of the raw material G at the discharge pressure of 1,000 Kg/cm$^2$.

FIG. 11 shows that the shorter fibrous celluloses present much more and the micro fibrils are found much more around the fibrous cellulose of the diameter of about 10 μm and it shows furthermore division of the raw material G at the discharge pressure of 1,500 Kg/cm$^2$.

From FIGS. 8 to 11, it was found that the fibrous celluloses in the suspension 2 were subdivided by the high pressure homogenizing device 1, that a plurality of divisions subdivided further the fibrous celluloses more than once, and that the higher discharge pressure of the orifice 3 subdivided the fibrous celluloses furthermore than the lower discharge pressure.

As a second measurement, a relation between the discharge pressure of the orifice 3 and the discharge temperature of the fibrous celluloses was measured while the fibrous celluloses in the suspension 2 were being subdivided.

The discharge temperature was measured at the first, second, and third fine division at the discharge pressure of 500 Kg/cm$^2$, 1,000 Kg/cm$^2$, and 1,500 Kg/cm$^2$ respectively.

The discharge temperature of the raw material G discharged from the orifice 3 was measured with a mercury thermometer of a scale 0 to 300 degrees C.

As the measurement condition, the water temperature was 26 degrees C., the ambient temperature was 27 degrees C., and the temperature of the raw material G after stirring by the mixer was 28.5 degrees C.

The discharge temperature of the raw material G at the discharge pressure of 500 Kg/cm$^2$ at the orifice 3 was 38.0, 41.5, and 42.5 degrees C. at the first, second, and third fine division, respectively.

The discharge temperature of the raw material G at the discharge pressure of 1,000 Kg/cm$^2$ at the orifice 3 was 45.5, 54.0, and 54.5 degrees C. at the first, second, and third fine division, respectively.

The discharge temperature of the raw material G at the discharge pressure of 1,500 Kg/cm² at the orifice 3 was 49.0, 60.0, and 63.0 degrees C. at the first, second, and third fine division, respectively.

TABLE 1 shows the result.

| discharge pressure [Kgf/cm²] | number of pass | discharge temperature [° C.] | temperature increase [° C.] |
|---|---|---|---|
| 500 | 1 | 38.0 | 9.5 |
| (49,000 KPa) | 2 | 41.5 | 3.5 |
|  | 3 | 42.5 | 1.0 |
| 1,000 | 1 | 45.5 | 17.0 |
| (98,000 KPa) | 2 | 54.0 | 8.5 |
|  | 3 | 54.5 | 0.5 |
| 1,500 | 1 | 49.0 | 20.5 |
| (147,000 KPa) | 2 | 60.0 | 11.0 |
|  | 3 | 63.0 | 3.0 |

(water temperature: 26° C., ambient temperature: 27° C., temperature after stirring with a mixer: 28.5° C.)

TABLE 1 shows that the discharge temperature increases with the increase of the discharge pressure 500 to 1,500 Kg/cm².

TABLE 1 shows that the temperature increase from the second pass to the third pass is smaller than that of from the first to second at the each discharge pressure.

It was found that the discharge temperature of the raw material G at the orifice 3 was not proportional to the discharge pressure at the orifice 3.

When the pressure is applied to the primary path of a tube having a given volume inside, the discharge pressure and discharge temperature of the secondary path are given by $$\rho \cdot Q \cdot c \cdot \Delta T = P \cdot Q \quad [\text{EQ. 1}]$$

that is $$\Delta T = P \cdot Q / \rho \cdot Q \cdot c \quad [\text{EQ. 2}]$$

where $\rho$: specific gravity of liquid (Kg/cm³), $c$: specific heat of liquid (Kcal/(Kg° C.), $Q$: discharged amount of liquid (Kgf/cm³), $P$: discharge pressure (Kgf/cm²), and $\Delta T$: discharge temperature (° C.).

The values related to the liquid are put into EQ. 2 to derive the discharge temperature of the subdivided raw material G discharged from the orifice 3 of the high pressure homogenizing device 1.

Figure 12:
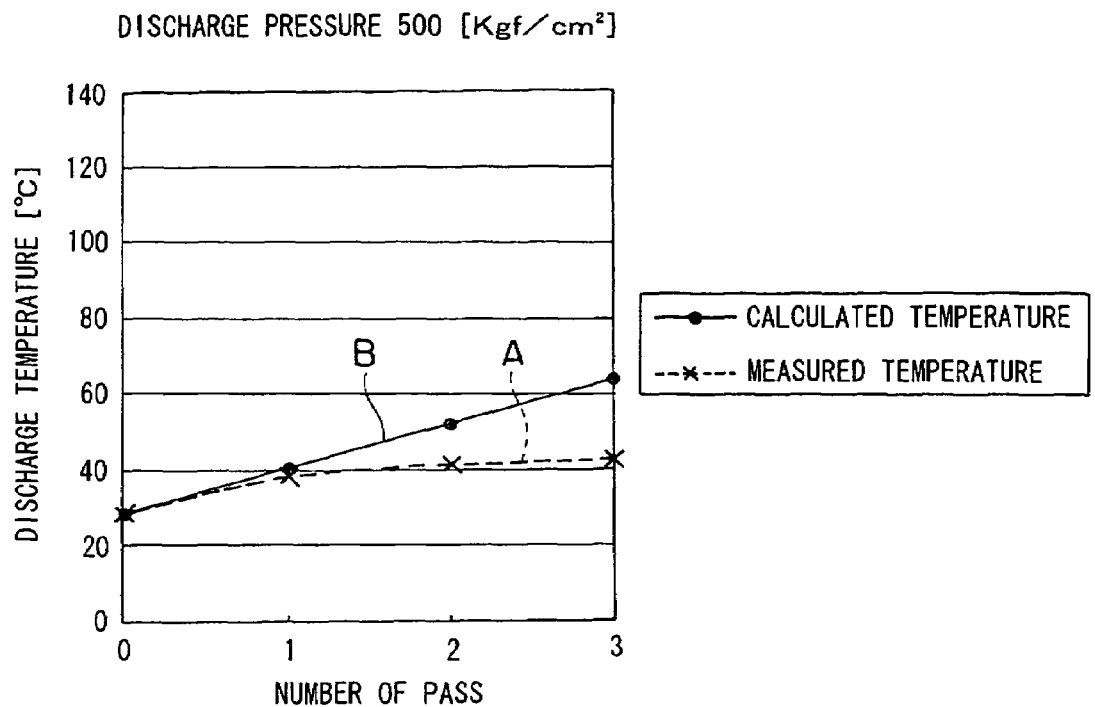
FIG. 12 is a graph of measured and calculated discharge temperatures when subdivided three times continuously at the orifice discharge pressure of 500 Kg/cm² (49,000 KPa) of the high pressure homogenizing device.
Figure 13:
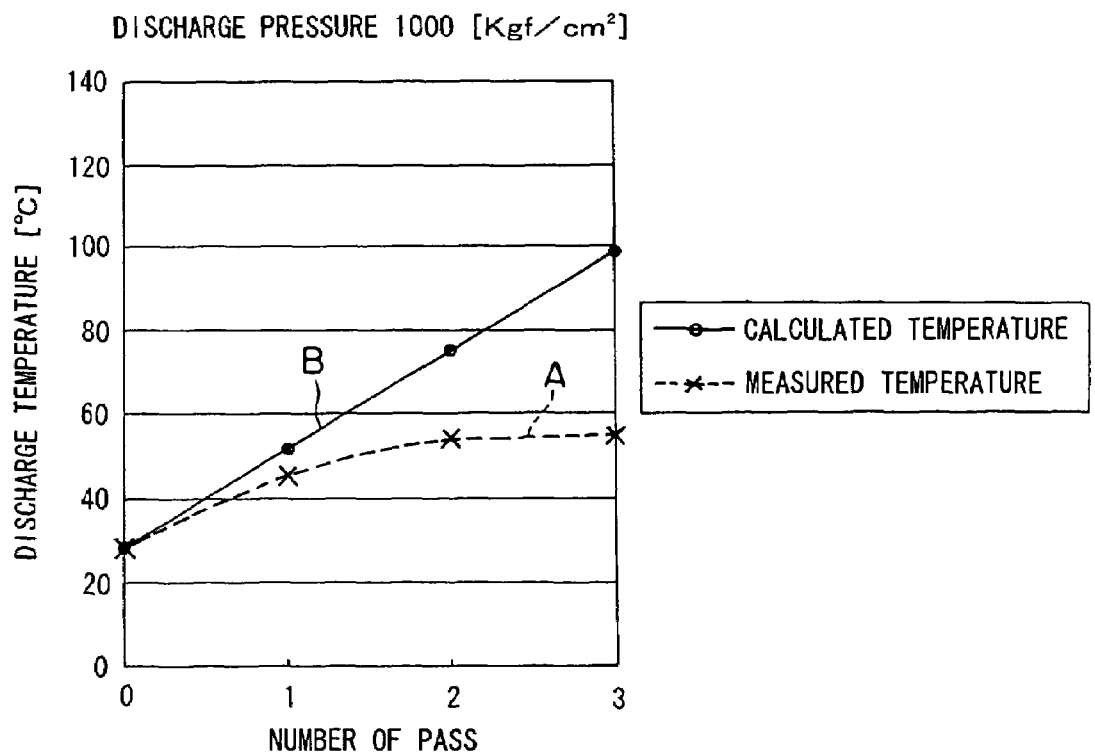
FIG. 13 is a graph of the measured and calculated discharge temperatures when subdivided three times continuously at the orifice discharge pressure of 1,000 Kg/cm² (98,000 KPa) of the high pressure homogenizing device.

FIGS. 12 to 14 show the discharge temperatures of the experiment A and the calculation B of EQ. 1 or EQ. 2 at the each discharge pressure.

FIG. 12 shows that for the discharge pressure 500 Kgf/cm² the calculated discharge temperatures B are 28.5° C., 40.0° C., 52.0° C., and 64.0° C. at after stirring, after the first fine division, after the second fine division, and after the third fine division, respectively. While, the experiment A gives 28.5° C., 38.0° C., 41.5° C., and 42.5° C. at the each corresponding step, respectively.

FIG. 13 shows that for the discharge pressure 1,000 Kgf/cm² the calculated discharge temperatures B are 28.5° C., 55.0° C., 75.0° C., and about 98.0° C. at after stirring, after the first fine division, after the second fine division, and after the third fine division, respectively. While, the experiment A gives 28.5° C., 45.5° C., 54.0° C., and 54.5° C. at the each corresponding step, respectively.

FIG. 14 shows that for the discharge pressure 1,500 Kgf/cm² the calculated discharge temperatures B are 28.5° C., 64.0° C., about 98.0° C., and 135.0° C. at after stirring, after the first fine division, after the second fine division, and after the third fine division, respectively. While, the experiment A gives 28.5° C., 49.0° C., 60.0° C., and 63.0° C. at the each corresponding step, respectively.

It is apparent that at the each condition of the discharge pressure and the number of pass the calculated value B is always higher than the measured value A.

TABLE 1 shows that the temperature increase at the next fine division decreases with the increase of number of the pass at the each discharge pressure.

The measured values of the discharge temperature are 28.5 to 63.0° C. at 500 to 1,500 Kgf/cm² and the temperature increase thereof is smaller than that of the calculated values. The calculated values have proportional temperature increases.

The temperature difference of the measured values A and the calculated values B is assumed to result from the energy to be consumed for cutting hydrogen bonding of the fibrous cellulose when the fibrous cellulose is passed and subdivided through the orifice 3.

Accordingly, the discharge temperature does not change the property of the fibrous cellulose.

Since the fine division of the present invention does not change and degrade the property of the raw material, it can be adapted to the raw materials G described above, such as in foods, in chemical products or cosmetics, in medical products, in glassware, in synthetic resin industries, in paper manufacturing field, and in pathology laboratories.

The fine division of the present invention can be adapted to not only the solid materials having a strong resistance to thermal alteration, but the materials having a weak resistance to thermal alteration.

In the conventional apparatus, the raw material is led into and discharged from the processing piston, driven with the motor, in the cylinder. After the several intakes and discharges of the raw material are carried out and the apparatus reaches to a prescribed high pressure, the raw material is finely divided. As the result, the conventional apparatus takes time to start the fine division. In the first embodiment of the present invention, the high pressure homogenizing device 1 can pressurize the raw material receiving passage 6 to 2,300 Kg/cm² quickly so as to achieve a high efficient fine division of the raw material G.

The conventional apparatus drives the piston in the cylinder with the motor and whereby the raw material is flowed through the intake valve and discharged from the outlet valve. On the other hand, the first embodiment of the high pressure homogenizing apparatus of the present invention does not utilize the piston driven with a motor, the intake and outlet valves to pressurize the raw material G to the high pressure H2 at the preceding step of the high pressure homogenizing device 1. Then the high pressure homogenizing apparatus of the present invention can subdivide easily the suspension even containing an entangling solid material, such as fibrous cellulose. Since the high pressure homogenizing apparatus does not have the piston driven with the motor, the intake valve, and the outlet valve, the valve operation is not required so that the solid material does not stick to the valves and the valve seats. The apparatus can supply the desired amount of the suspension 2 at a constant speed.

The homogenizing apparatus of the first embodiment can subdivide the raw material G with high efficiency under high pressure or very high pressure without leakage of the raw material G.

The homogenizing apparatus of the present invention does not utilize the piston driven with the motor, the intake valve, and the outlet valve to pressurize the raw material. Consequently, the maintenance and control to repair and replace these parts are not required to the apparatus of the first embodiment. Since the apparatus does not have these parts to be worn or damaged, the lifetime of the apparatus becomes longer so that the labor hour and cost are saved.

Figure 15:
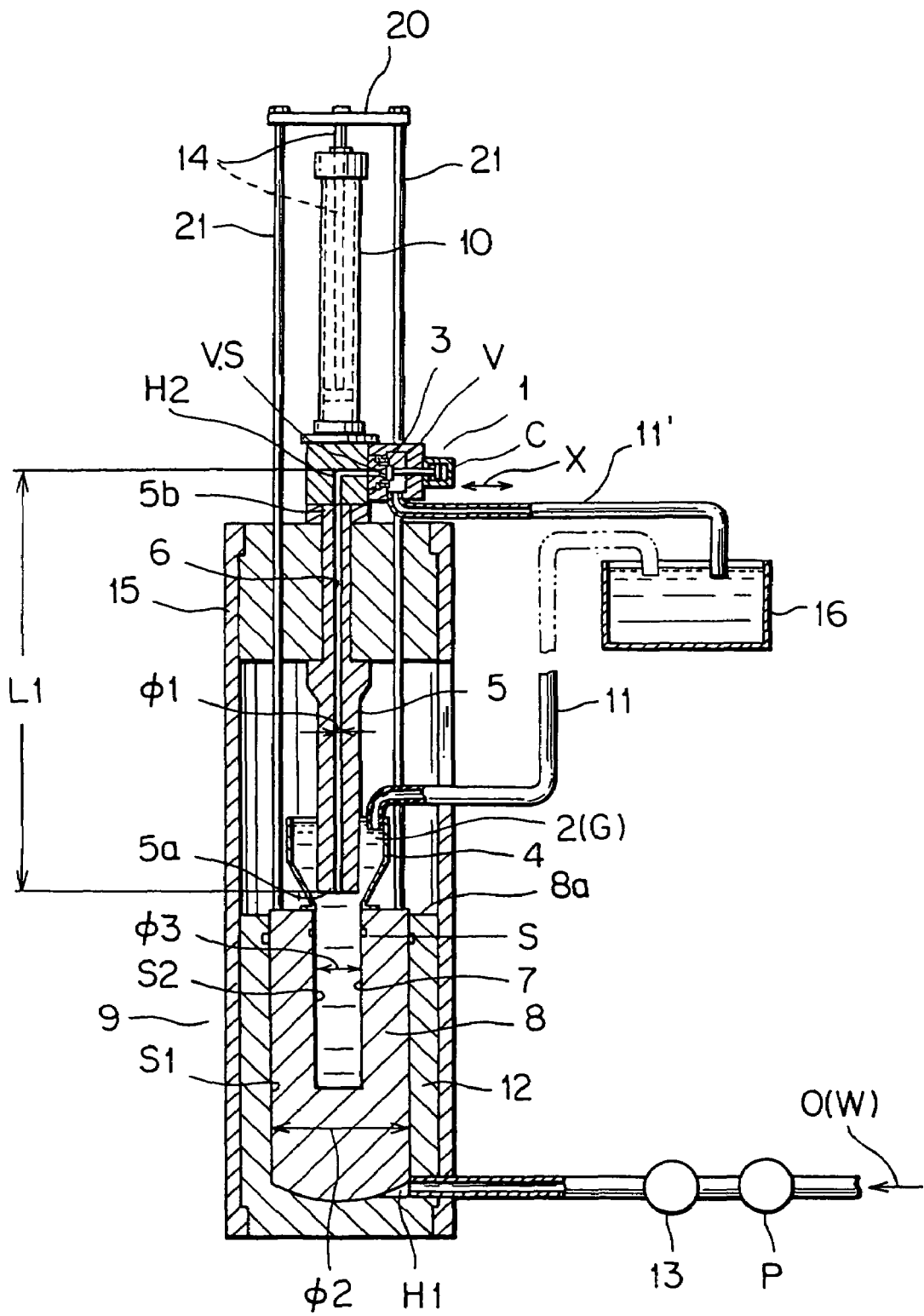
FIG. 15 is a sectional view showing a second embodiment of a high pressure homogenizing apparatus of the present invention.
Figure 16:
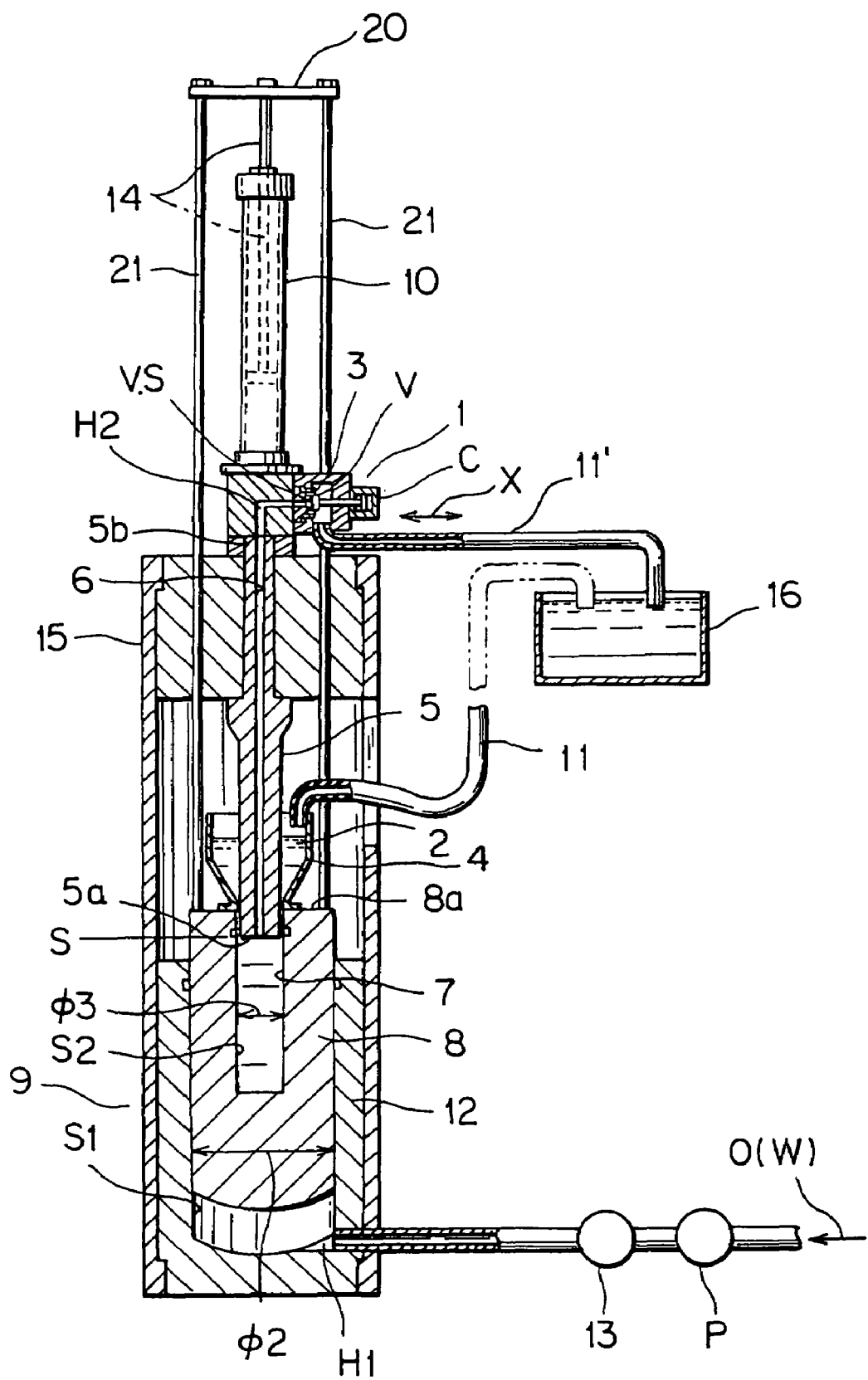
FIG. 16 is a sectional view showing that a processing piston passes through a watertight position in a processing recess and pressurizes a suspension.
Figure 17:
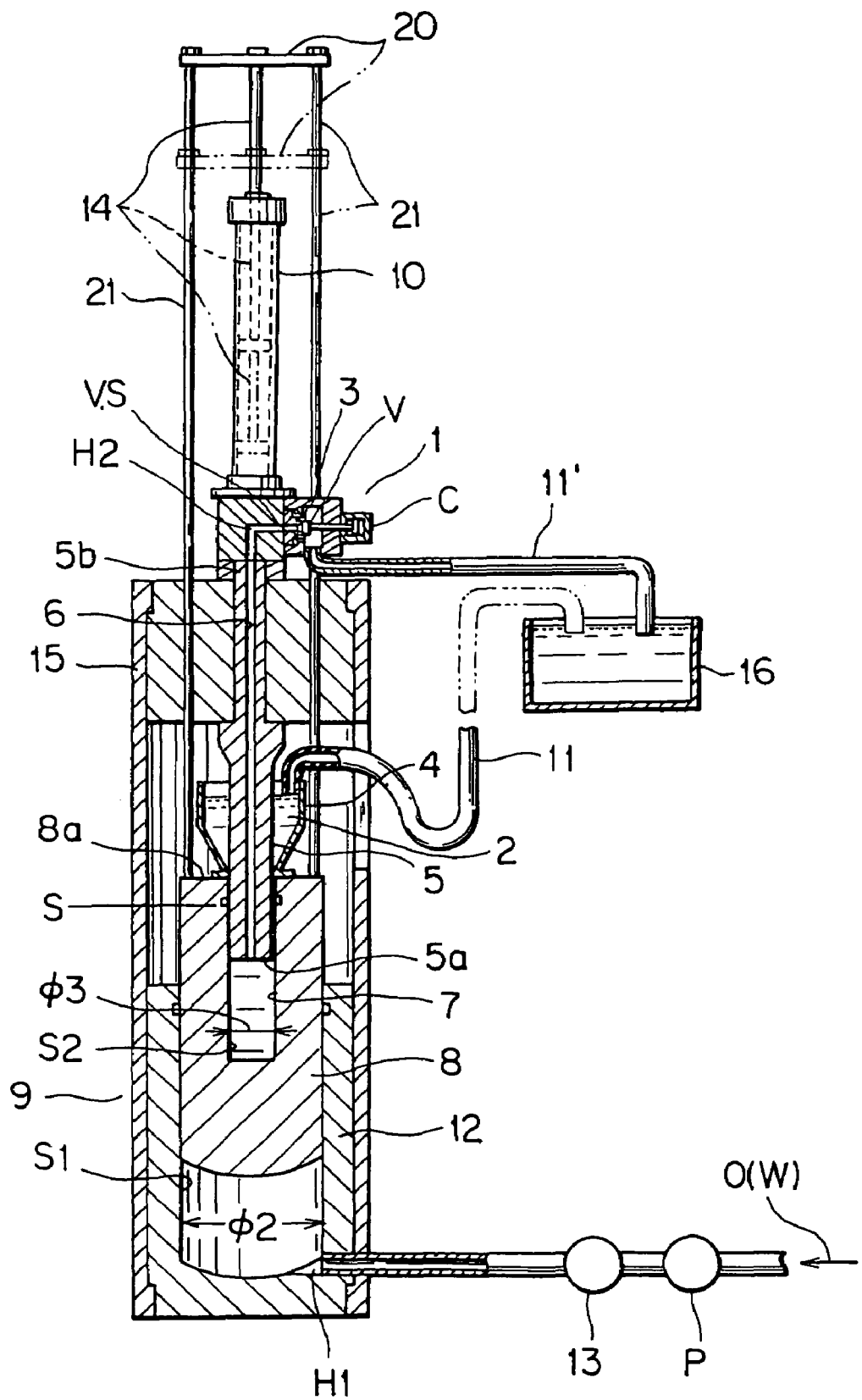
FIG. 17 is a sectional view showing that the suspension is led into a raw material receiving passage and pressurized to high pressure.

FIGS. 15 to 17 show a high pressure homogenizing apparatus of a second embodiment of the present invention. The apparatus has a cylinder 10 connected to a booster piston 8, through a joining bar 20 attached to one end of the cylinder 10 and joining rods 21 suspended downwardly from the joining bar 20 at both sides thereof. The second embodiment utilizes one cylinder 10 to move the booster piston 8 compared with the first embodiment so that as the number of parts becomes small, the manufacturing and assembly become easy and the manufacturing cost is reduced. The formation and operation of the apparatus is same as those of the first embodiment.

Figure 18:
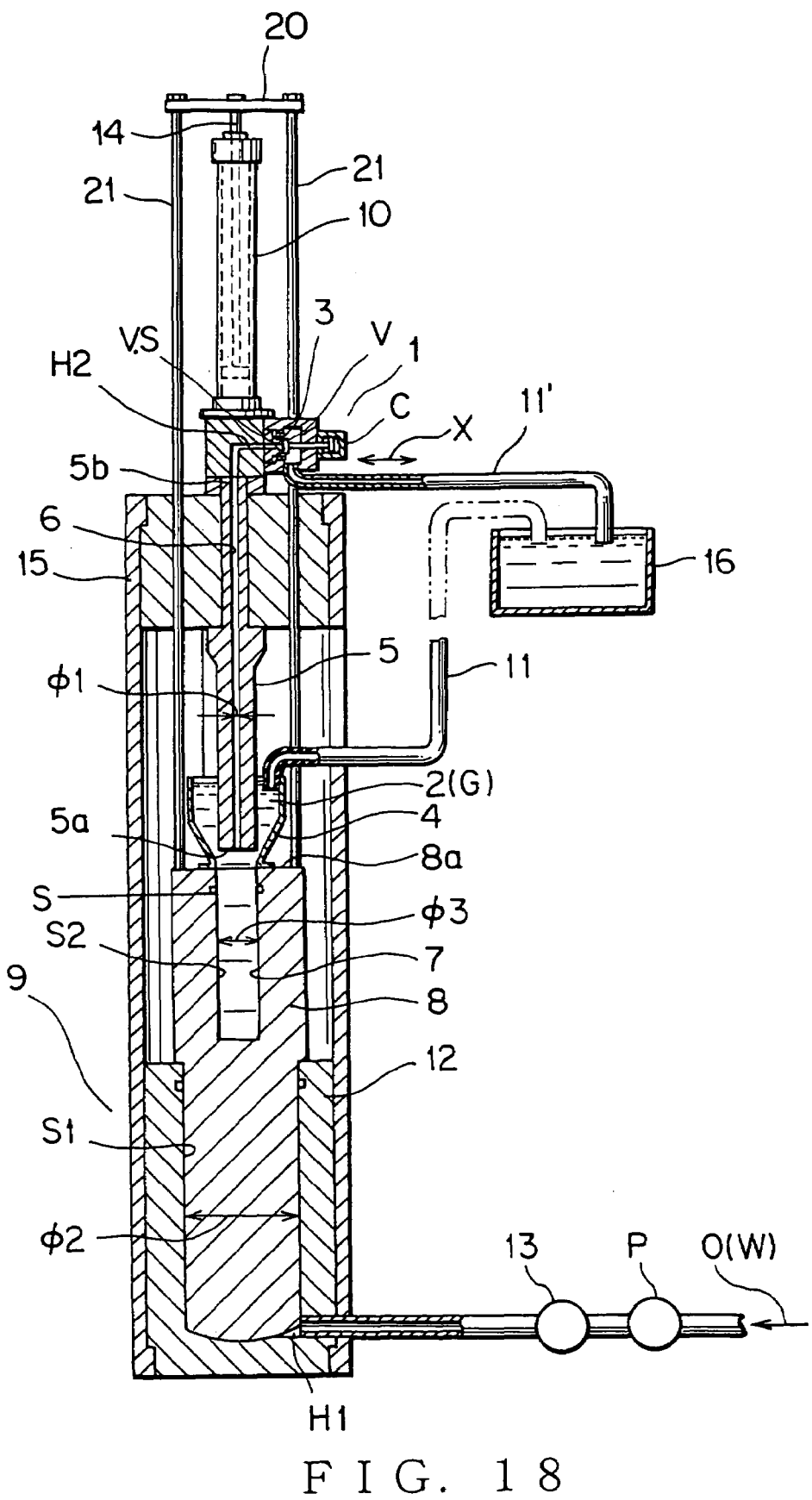
FIG. 18 is a sectional view of a third embodiment of a homogenizing apparatus of the present invention.

FIG. 18 shows a high pressure homogenizing apparatus of a third embodiment of the present invention. The homogenizing apparatus has a longer booster piston 8 than those of the first and second embodiments. The longer booster piston 8 can be easily formed and has higher resistance to pressure. The longer booster piston 8 does not require high accuracy manufacturing to assemble and manufacture with a booster cylinder 12 and a processing piston 5. The formation and operation of the apparatus is same as those of the first and second embodiments.

Figure 19:
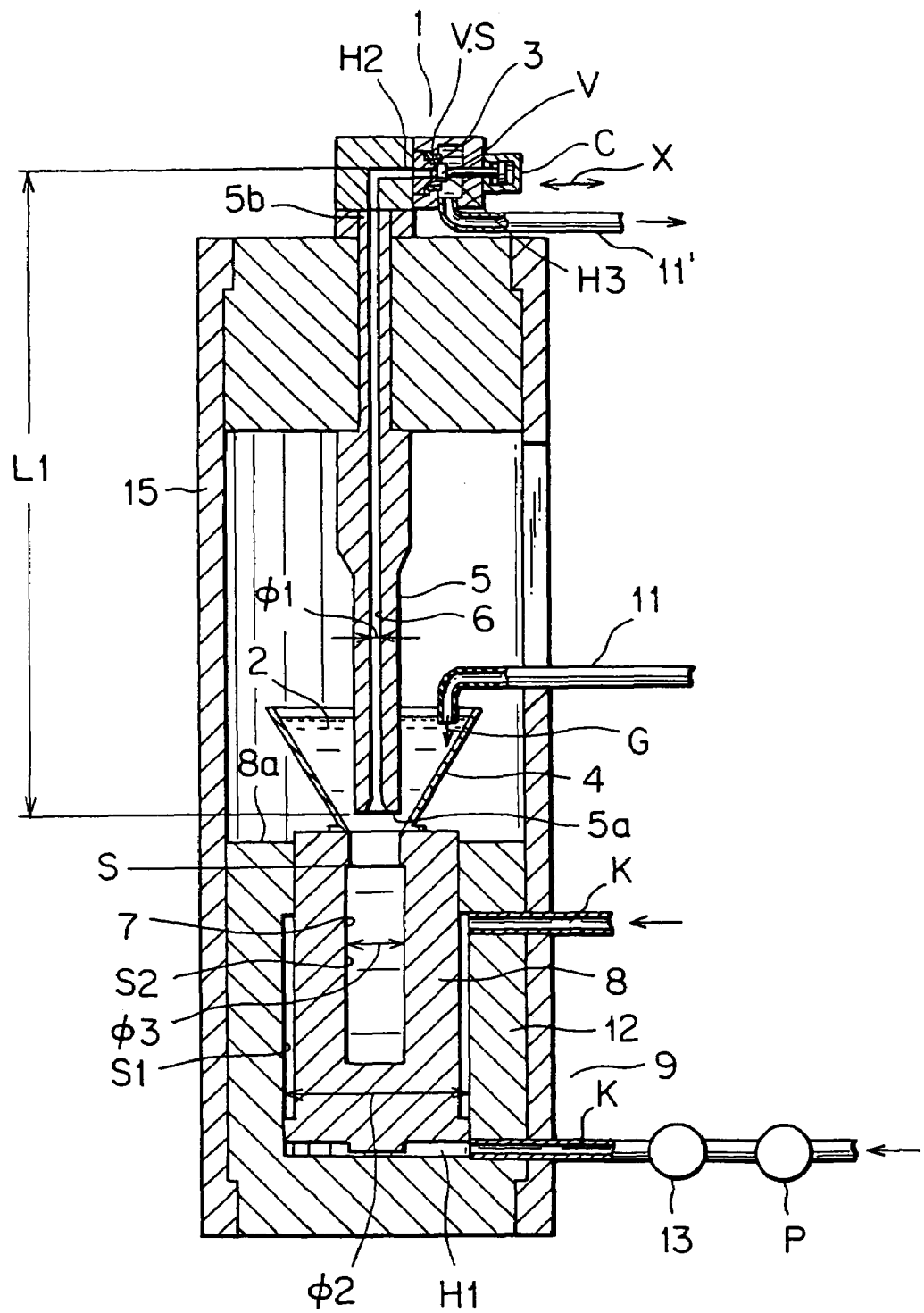
FIG. 19 is a sectional view of a fourth embodiment of a homogenizing apparatus of the present invention.

FIG. 19 shows a fourth embodiment of a homogenizing apparatus of the present invention.

In the first to third embodiments, the each cylinder 10 to move the booster piston 8 is disposed at the upper portion of the frame 15. In the fourth embodiment, in place of that, a hydraulic or water pressure circuit K is disposed inside a booster cylinder 12 of a pressure intensifier 9. A booster piston 8 is moved toward a processing piston 5 with the pressure and a front end (one end 5a) of the processing piston 5 is inserted into a processing recess 7 through a hopper 4. When the processing piston 5 passes through a watertight position S in the processing recess 7 and pressurizes the processing recess 7, a suspension 2 containing a raw material G is led into a raw material receiving passage 6 and pressurized to a high pressure H2. The booster piston 8 is returned to an initial position by changing the hydraulic or water pressure of the circuit K.

The fourth embodiment does not have a cylinder 10 to move the booster piston 8 so that the number of parts is reduced and the manufacturing and assembly become simple. The formation and function are the same as those of the first to third embodiments.

Figure 20:
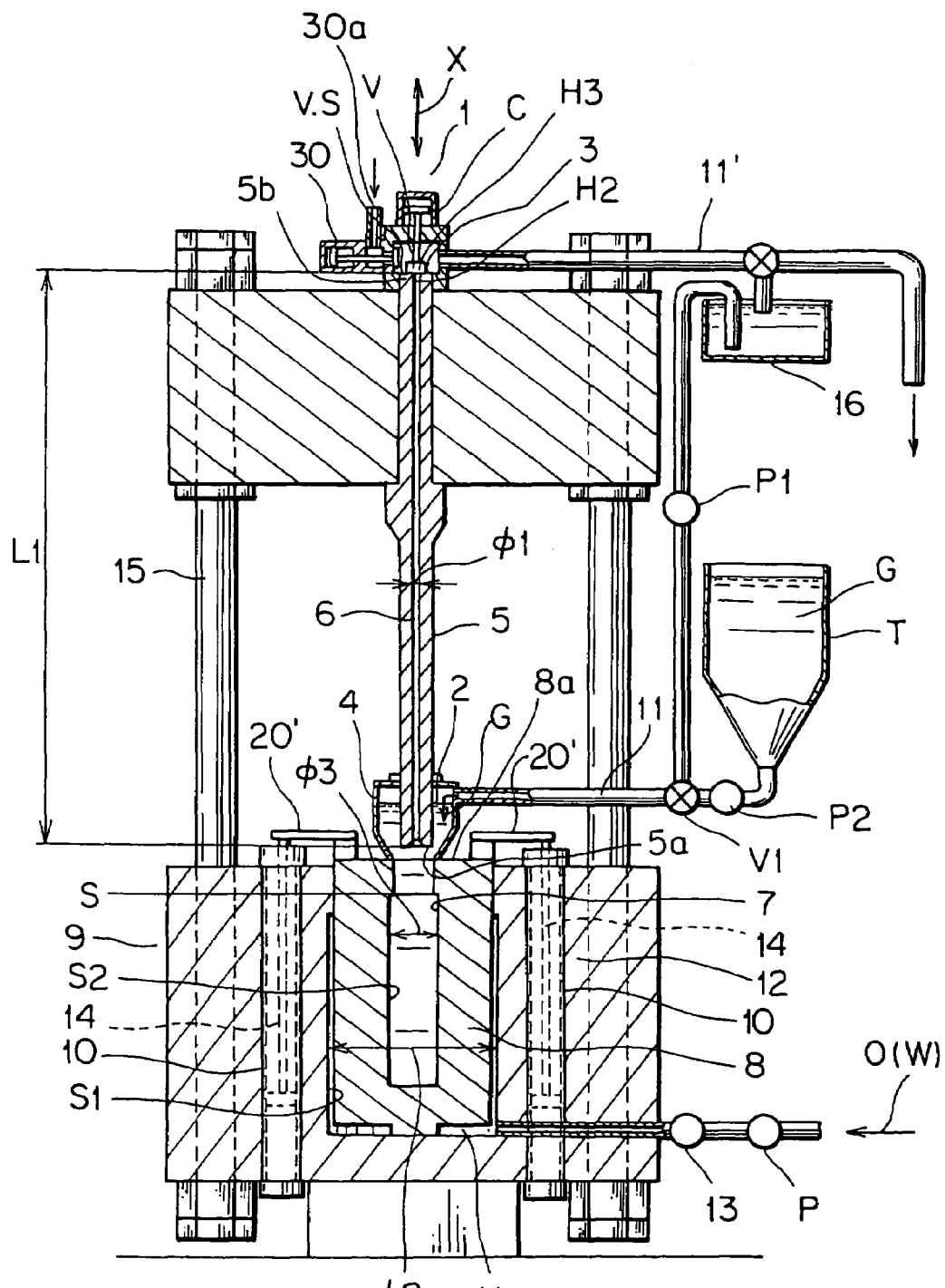
FIG. 20 is a sectional view of a fifth embodiment of homogenizing apparatus of the present invention.

FIG. 20 shows a fifth embodiment of a homogenizing apparatus of the present invention.

In the first to third embodiments, the cylinder 10 to move the booster piston 8 is disposed at the upper portion of the frame 15. In the fifth embodiment, in place of that, a plurality of cylinders 10 are disposed around a booster cylinder 12 receiving the booster piston 8 through piston rods 14 and joining bars 20'. The booster piston 8 of a pressure intensifier 9 is movable toward a processing piston 5. The booster piston 8 is moved toward the processing piston 5 with the pressure and a front end (one end 5a) of the processing piston 5 is inserted into a processing recess 7 through a hopper 4. When the processing piston 5 passes through a watertight position S in the processing recess 7 and pressurizes the processing recess 7, a suspension 2 containing a raw material G is led into a raw material receiving passage 6 and pressurized to a high pressure H2. The booster piston 8 is returned to an initial position by driving the cylinders 10.

In the first to third embodiments, the cylinder 10 is disposed above the frame 15. The cylinders 10 are disposed around the booster cylinder 12 of the pressure intensifier 9 disposed at a lower position of the frame 15. The hopper 4 to receive the raw material G is placed above the cylinders 10 so that an oil or water to drive the cylinders 10 does not contaminate the raw material due to leakage. Since a large space is available around the hopper 4, it is possible to observe fast and assuredly the condition or the supply of the raw material G and to easily manufacture and assembly, and maintain and control the apparatus.

In the fifth embodiment, an air inlet valve 30 having a hole 30a to supply air is disposed at one side of a high pressure homogenizing device 1 placed at the other end (an upper end in FIG. 20) of the processing piston 5. The booster piston 8 is returned to the initial position after the raw material G is finely divided with the same process as the other embodiments. When the booster piton 8 returned, the outside air is led from the hole 30a into the raw material receiving passage 6 in the processing piston 5 to break vacuum so as to make the downward movement of the booster piston 8 easily.

In the fifth embodiment, the subdivided raw material G received in a container 16 is supplied to the hopper 4 with a prescribed time and amount through a pipe 11 having a pump P1 for further fine dividing. In the fifth embodiment, there is a raw material tank T, which supplies the initial raw material G to the hopper 4 through a pump P2 and a selector valve V1. In FIG. 20, the hopper 4 is an encapsulated type but not limited to this type and can be an opened type.

The air inlet valve 30 can be any type of structure as far as the outside air is led from the valve 30 every after the raw material G is finely divided at the high pressure homogenizing device 1.

Figure 21:
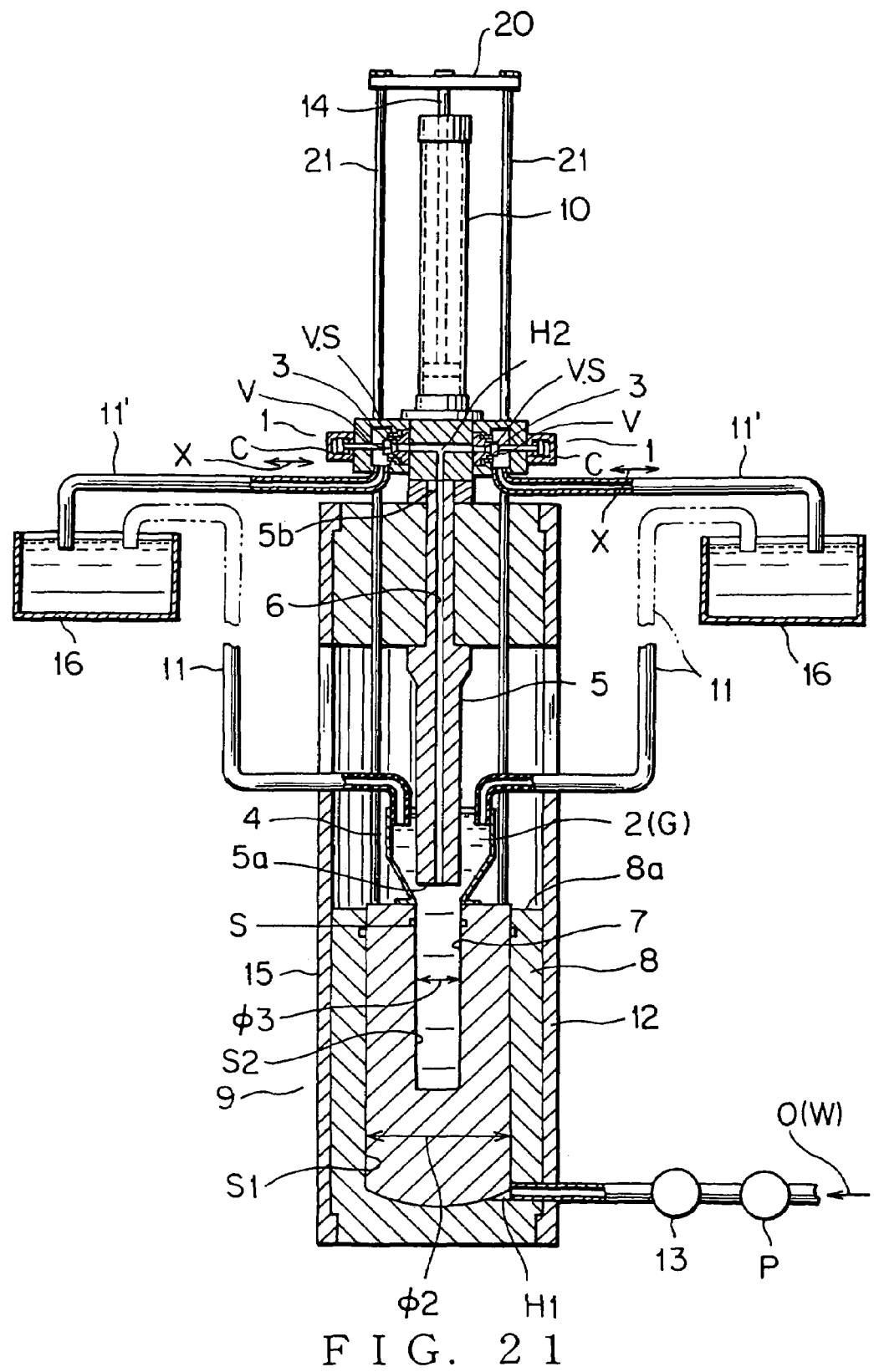
FIG. 21 is a sectional view of a sixth embodiment of a homogenizing apparatus of the present invention.

FIG. 21 shows a sixth embodiment of the present invention.

The sixth embodiment has a plurality of high pressure homogenizing devices 1, two mechanisms 1 in FIG. 21, attached to one end 5b in a secondary path. A suspension 2 containing a raw material G is pressurized by a booster piston 8 similarly to the other embodiments. The sixth embodiment can achieve larger processing amount and higher efficiency of fine division of the raw material compared with the first to third embodiments. The fine divisions of the plurality of the high pressure homogenizing devices 1 can be performed at the same time or at the different time each. The number of the high pressure homogenizing devices 1 is not limited to two as shown in FIG. 21 and can be optional.

Figure 22:
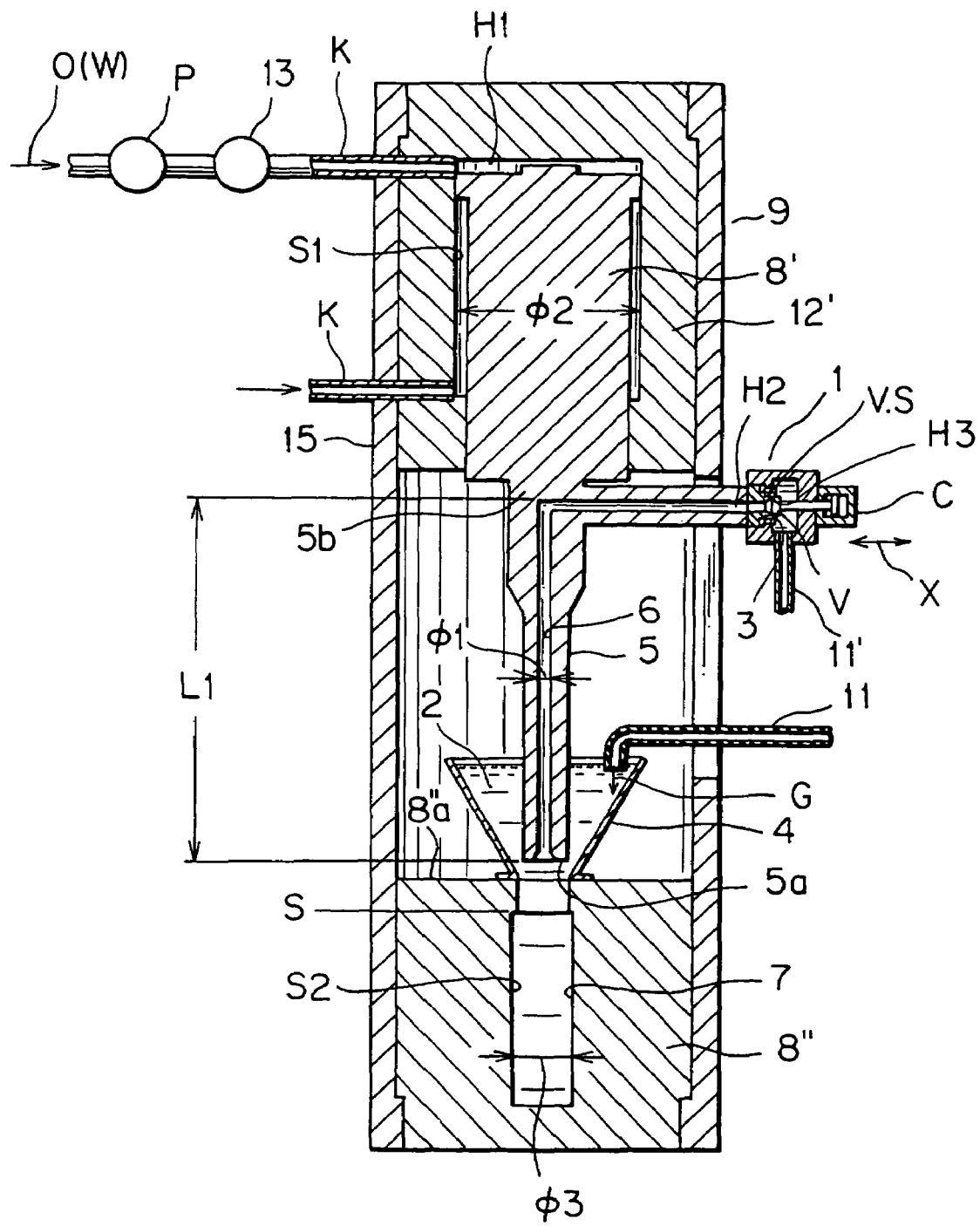
FIG. 22 is a sectional view of a seventh embodiment of a homogenizing apparatus of the present invention.

FIG. 22 shows a seventh embodiment of the present invention.

In the first to sixth embodiments, the booster piston 8 is moved toward the processing piston 5 fixed to the frame 15 and the front end 5a of the processing piston 5 is inserted into the processing recess 7 and the suspension 2 containing the raw material G is led into the raw material receiving passage 6 so as to pressurize the suspension 2 to the high pressure H2.

In the seventh embodiment, as shown in FIG. 22, a pressure intensifier 9 includes a booster cylinder 12', into which an oil or water flows, above a frame 15 and a booster piston 8', slidable to the booster cylinder 12', has a processing piston 5 at the center of a lower portion thereof. A hopper 4 and a cylinder 8" are disposed at a lower portion of the frame 15. The cylinder 8" as a fixed receiver has a processing recess 7 arranged at one end thereof and a front end 5a of the processing piston 5 is inserted into the processing recess 7.

The processing piston 5 attached to the booster piton 8' is moved, downwardly in FIG. 22, to the cylinder 8" fixed to the lower portion of the frame 15. The front end 5a of the processing piston 5 is inserted into the processing recess 7 in the cylinder 8" to make watertight between them. The suspension 2 is led into a raw material receiving passage 6 and pressurized to a high pressure H1 and subdivided at a high pressure homogenizing device 1. Except above, the formation and operation are the same as those of the first to sixth embodiments.

Figure 23:
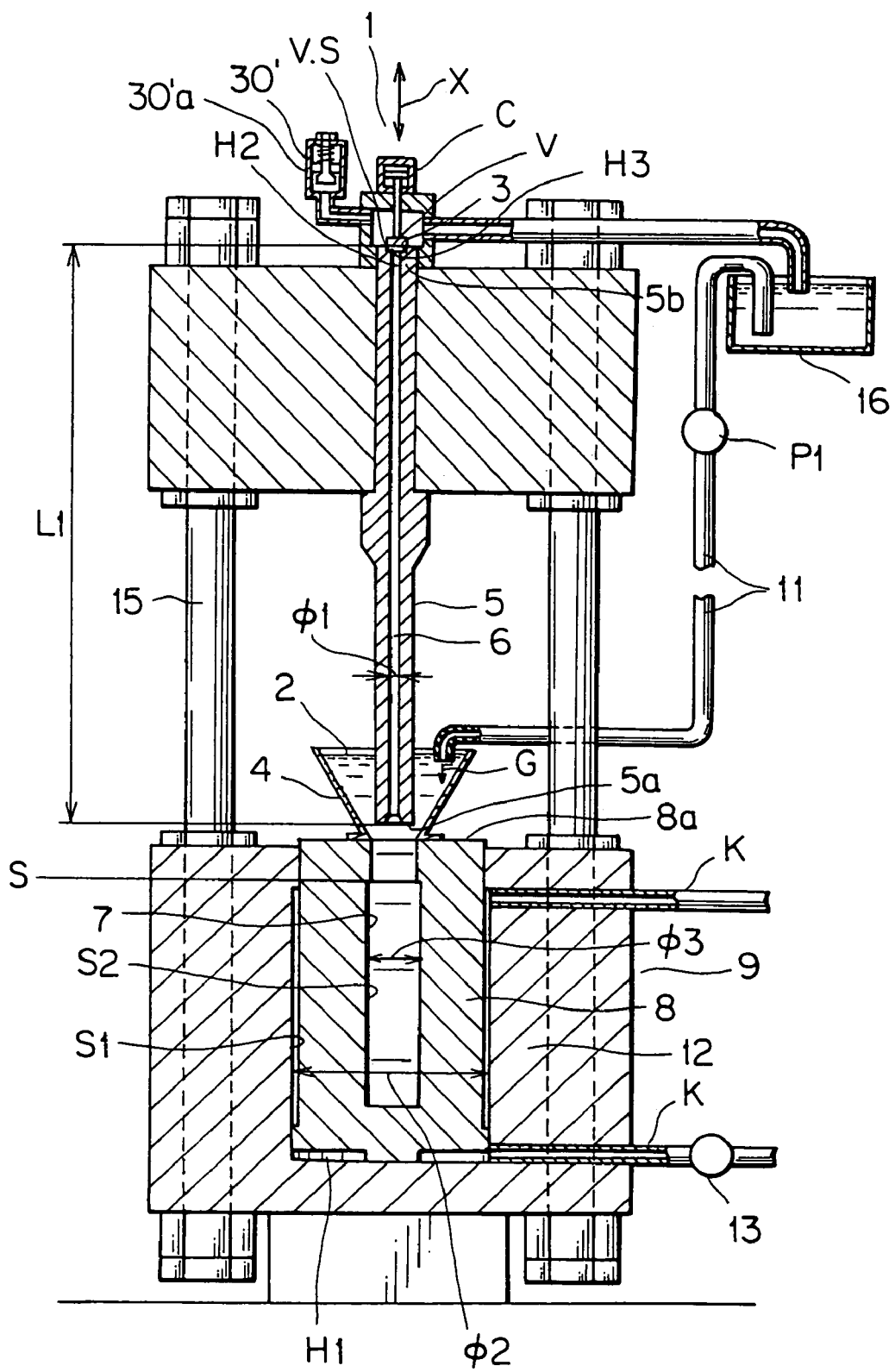
FIG. 23 is a sectional view of an eighth embodiment of a homogenizing apparatus of the present invention.

FIG. 23 shows a eighth embodiment of the present invention.

The eighth embodiment includes a high pressure homogenizing device 1 attached to one end 5b (upper end in FIF. 23) of a processing piston 5 and an air inlet valve 30', arranged one side of the high pressure homogenizing device 1, having a valve 30'a which is always closed by a spring force. A booster piston 8 of a pressure intensifier 9 disposed at a lower portion of a frame 15 is moved toward the processing piston 5 and a suspension 2 containing a raw material G is finely divided by the same process as described in the first to sixth embodiments.

In the eighth embodiment, when the booster piston 8 is returned to an initial position, the air inlet valve 30' leads an outside air into a raw material receiving passage 6 through the high pressure homogenizing device 1 so that the movement of the booster piston 8 becomes easier than that in vacuum. The eighth embodiment has a pump P1 arranged on a way of a pipe 11 to supply the suspension 2 containing the subdivided raw material G to a hopper 4. The pump P1 has the same formation and function as that of the fifth embodiment shown in FIG. 20. Except the pump P1, the eighth embodiment is the same as the fourth embodiment of FIG. 19.

Figure 24:
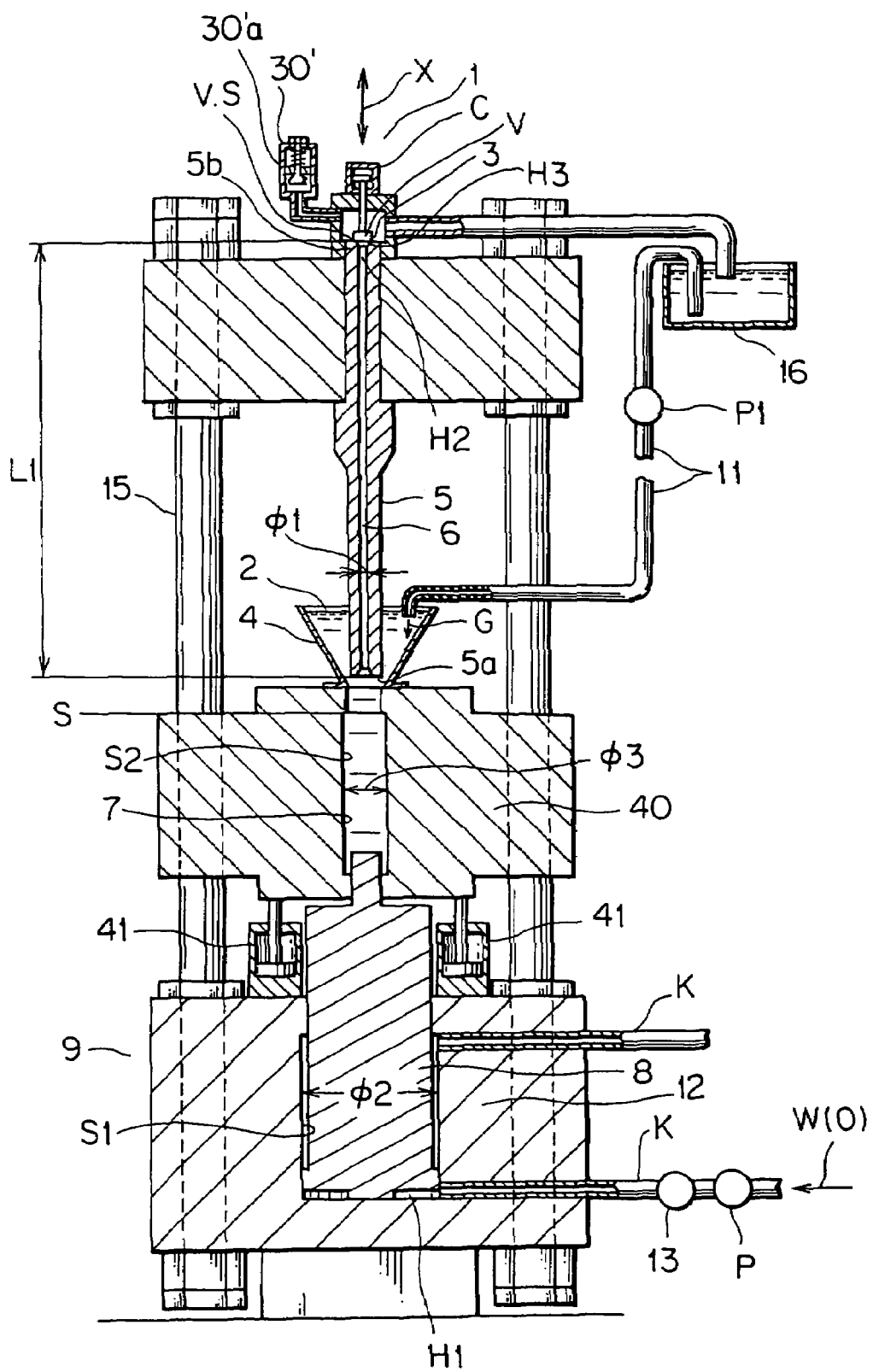
FIG. 24 is a sectional view of a ninth embodiment of a homogenizing apparatus of the present invention.

FIG. 24 shows a ninth embodiment of the present invention.

The ninth embodiment includes a processing piston 5 fixed to a frame 15, a booster piston 8 movable toward the processing piston 5, and a cylinder 40 movable toward the processing piston 5. The movable cylinder 40 has a processing recess 7 and is driven by the booster piston 8 so that a front end (one end 5a) of the processing piston 5 enters into the processing recess 7.

In order to lead a suspension 2 in a hopper 4, containing a raw material G, into a raw material receiving passage 6 disposed inside the processing piston 5, a water W or oil O is flowed into a booster cylinder 12 with a pump P and the booster piston 8 is moved upwardly. The movable cylinder 40 is moved toward the processing piston 5, causing a compression inside the processing recess 7, and the suspension 2 is led into the raw material receiving passage 6 and pressurized to a high pressure H2. The pressurized suspension 2 is then passed through an orifice 3 of a high pressure homogenizing device 1 with high speed at a high pressure H3 to finely divide the raw material G. The formation and function are different from those of the fourth and eighth embodiments.

After the fine division of the raw material G at the orifice 3, the movable cylinder 40 is moved downwardly to an initial position by a plurality of cylinders 41 disposed at an upper surface of the booster cylinder 12. It is suitable to finely divide the raw material G at very high pressure. Except that, the formation and function is the same as the fourth and eighth embodiments.

Figure 25:
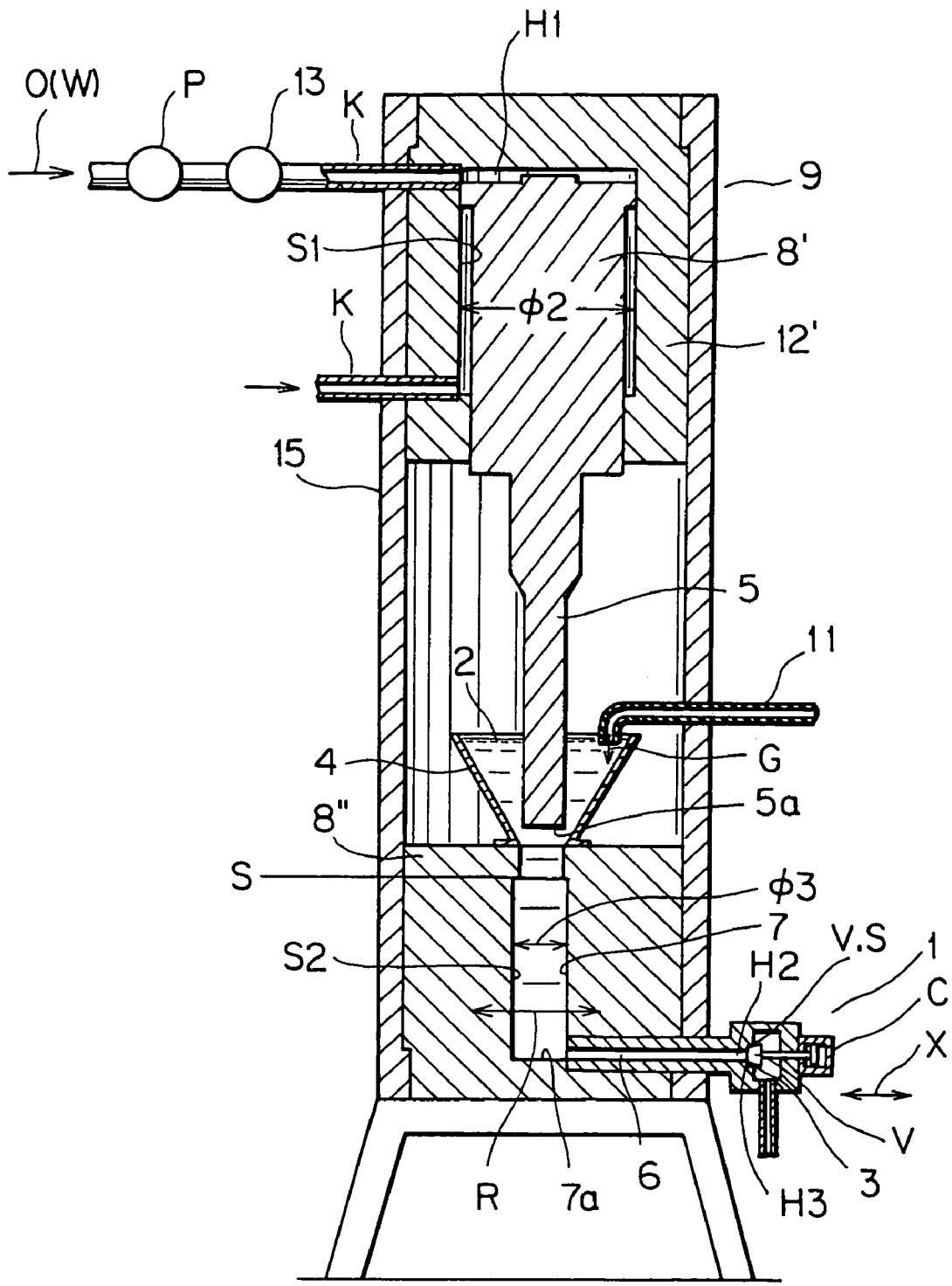
FIG. 25 is a sectional view of a tenth embodiment of a homogenizing apparatus of the present invention.

FIG. 25 shows a tenth embodiment of the present invention.

In the tenth embodiment, a processing piston 5 is connected to a booster piston 8' and movable with respect to a frame 15 and a cylinder 8" is fixed to the frame 15. The formation is the same as the seventh embodiment. The different formation and function from the seventh embodiment is that a raw material receiving passage 6 is disposed in a radial direction of a processing recess 7 and communicates with the processing recess 7 and a high pressure homogenizing device 1 instead of being disposed inside the processing piston 5. Then, the suspension 2 in the raw material receiving passage 6 is led into the high pressure homogenizing device 1 horizontally and the raw material G is finely divided at the high pressure homogenizing device 1.

In the tenth embodiment, the raw material receiving passage 6 is arranged horizontally instead of the first to fifth, seventh, and eighth embodiments where the raw material receiving passage 6 is arranged in the axial direction of the processing piston 5. Thus, a high pressure homogenizing apparatus can be smaller and compact size. Since the processing piston 5 does not have the raw material receiving passage 6 along the axial direction, it can be easily manufactured and formed. The tenth embodiment is adapted to a raw material G having high viscosity, large size solid materials, or long fibrous celluloses. These raw materials can be passed through the raw material receiving passage 6 fast and assuredly and subdivided through an orifice 3 of a high pressure homogenizing device 1.

Figure 26:
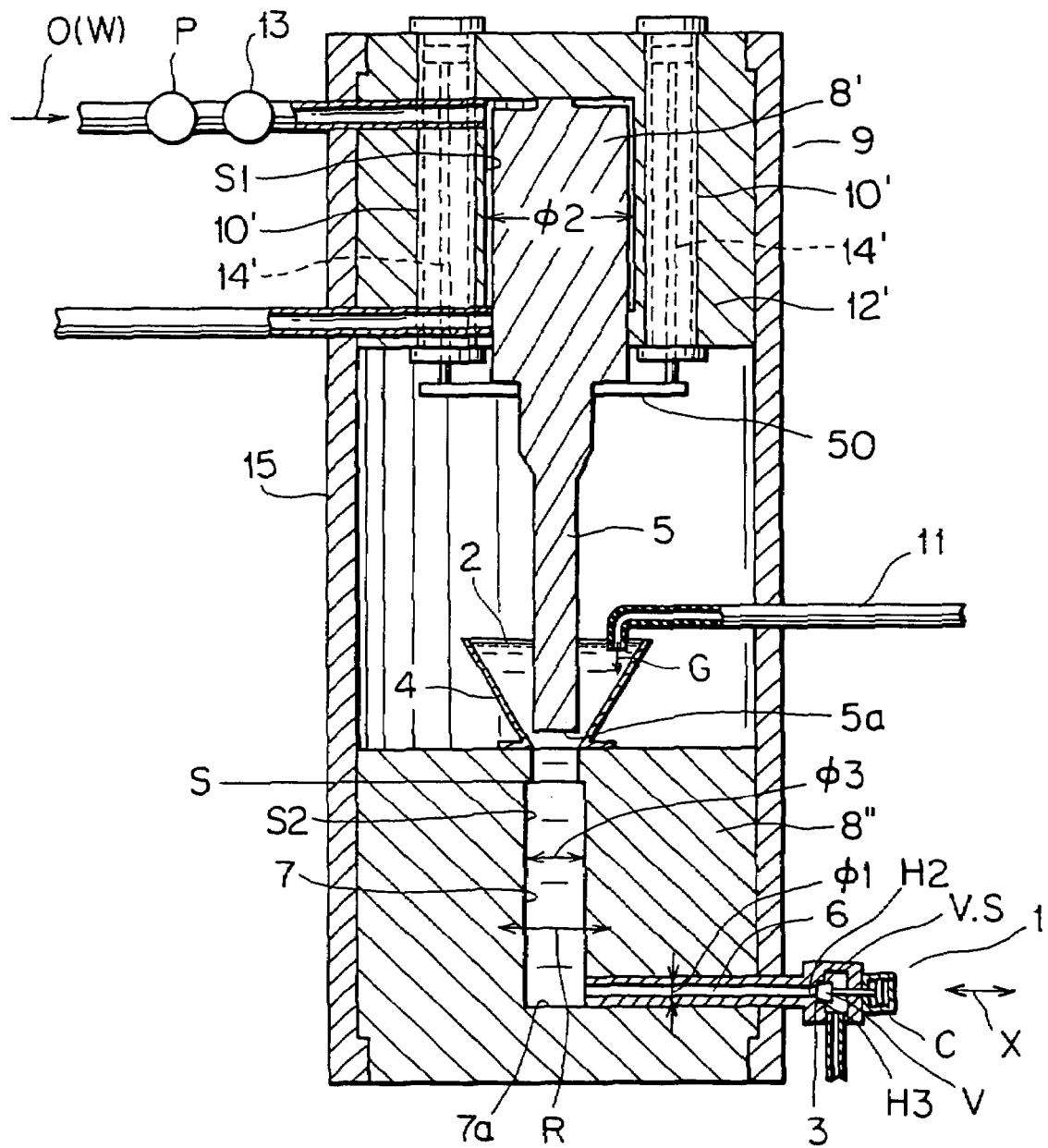
FIG. 26 is a sectional view of an eleventh embodiment of a homogenizing apparatus of the present invention.

FIG. 26 shows an eleventh embodiment of the present invention.

In the eleventh embodiment, similarly to the tenth embodiment, a processing piston 5 is connected to a booster piston 8' and movable with respect to a frame 15 and a cylinder 8" is fixed to the frame 15. A raw material receiving passage 6 is disposed in a radial direction of a processing recess 7 and communicates with the processing recess 7 and a high pressure homogenizing device 1. The horizontal raw material receiving passage 6 is disposed at a bottom 7a of the processing recess 7 without a step so as to flow smoothly inside the raw material receiving passage 6 with a desired amount of a suspension 2 containing a raw material G.

Contrast to the seventh and tenth embodiments, in the eleventh embodiment, cylinders 10' to move up and down piston rods 14' are disposed around a booster cylinder 12. Ends of the piston rods 14' are connected to both sides of a joining bar 50, through which the processing piston 5 passes at about the center. After the fine division of the raw material G through an orifice 3, the booster piston 8' is moved upwardly to an initial position with the cylinders 10'.

Figure 27:
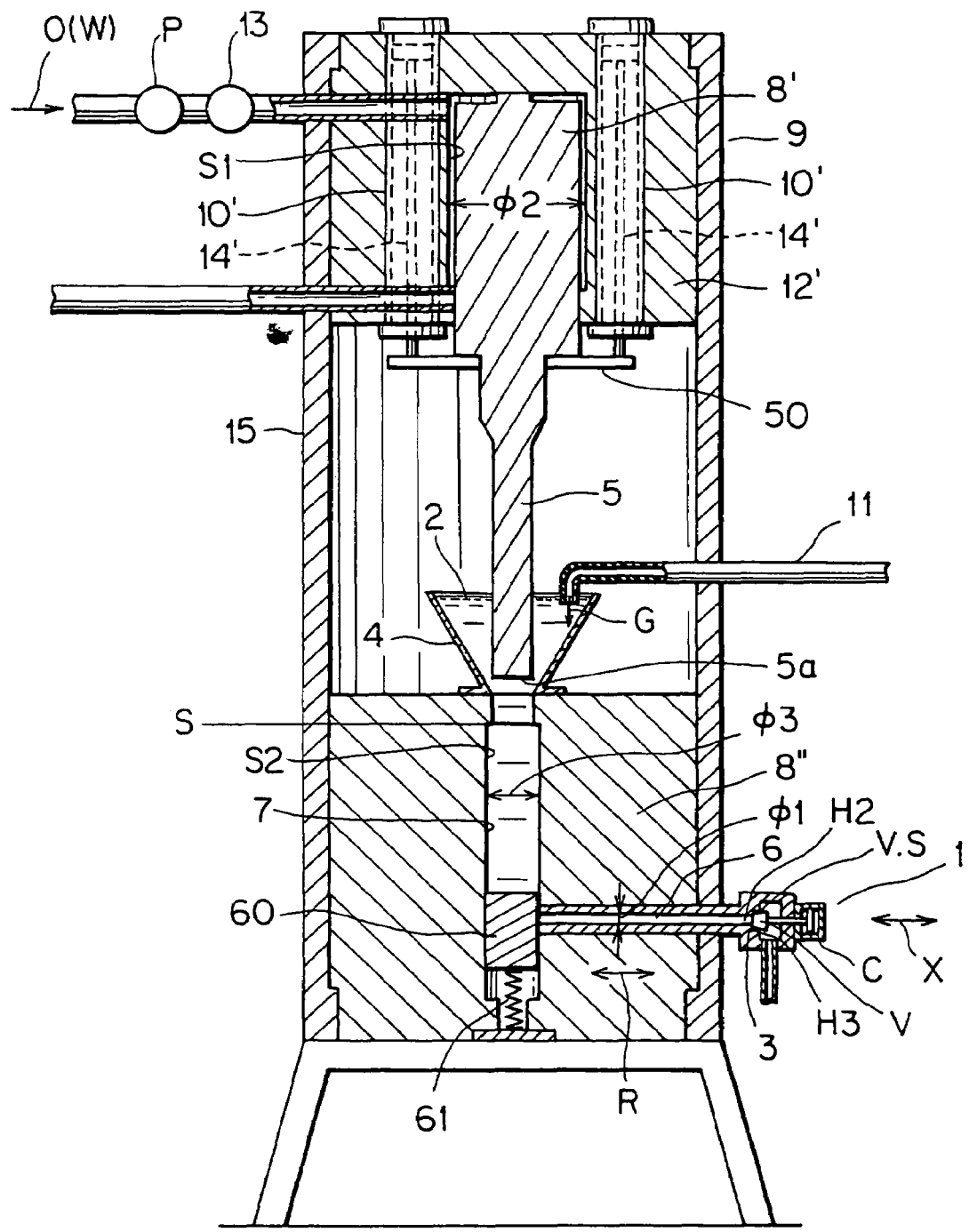
FIG. 27 is a sectional view showing that a sliding valve closes a raw material receiving passage of a twelfth embodiment of a homogenizing apparatus of the present invention.
Figure 28:
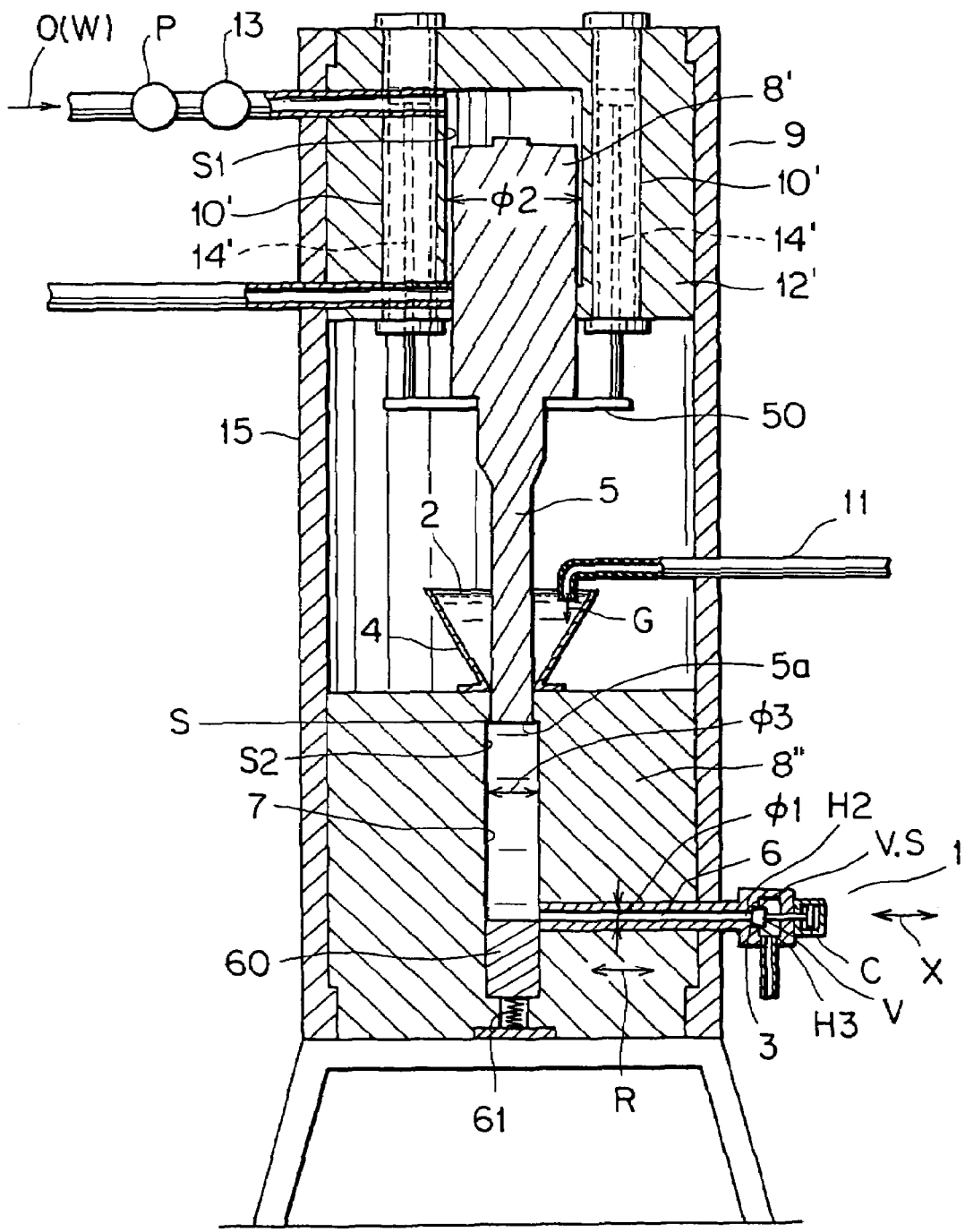
FIG. 28 is a sectional view showing that the sliding valve opens the raw material receiving passage of the twelfth embodiment of the homogenizing apparatus.

FIGS. 27 and 28 show a twelfth embodiment of the present invention.

The twelfth embodiment includes a sliding valve 60 disposed inside and at a lower portion of a processing recess 7. The sliding valve 60 is opened and closed by a pressure change caused by a processing piston 5 and communicates the processing recess 7 with a high pressure homogenizing device 1 so that the horizontally extending raw material receiving passage 6 is opened and closed. For finely dividing a raw material G with the high pressure homogenizing device 1, a front end 5a of the processing piston 5 is inserted into the processing recess 7 by driving a pressure intensifier 9 disposed at an upper position of a frame 15 and the processing piston 5 passes through a watertight position S to pressurize the processing recess 7.

As the processing piston 5 of a booster piston 8' is moved downwardly and the internal pressure of the processing recess 7 increases, the sliding valve 60 is moved downwardly against a spring 61 to open the raw material receiving passage 6. When the processing recess 7 is pressurized by the processing piston 5, which passes through the watertight position S and a volume inside the processing recess 7 is compressed, the raw material G flows into the raw material receiving passage and is finely divided when the raw material G passes through an orifice 3 of the high pressure homogenizing device 1.

Figure 29:
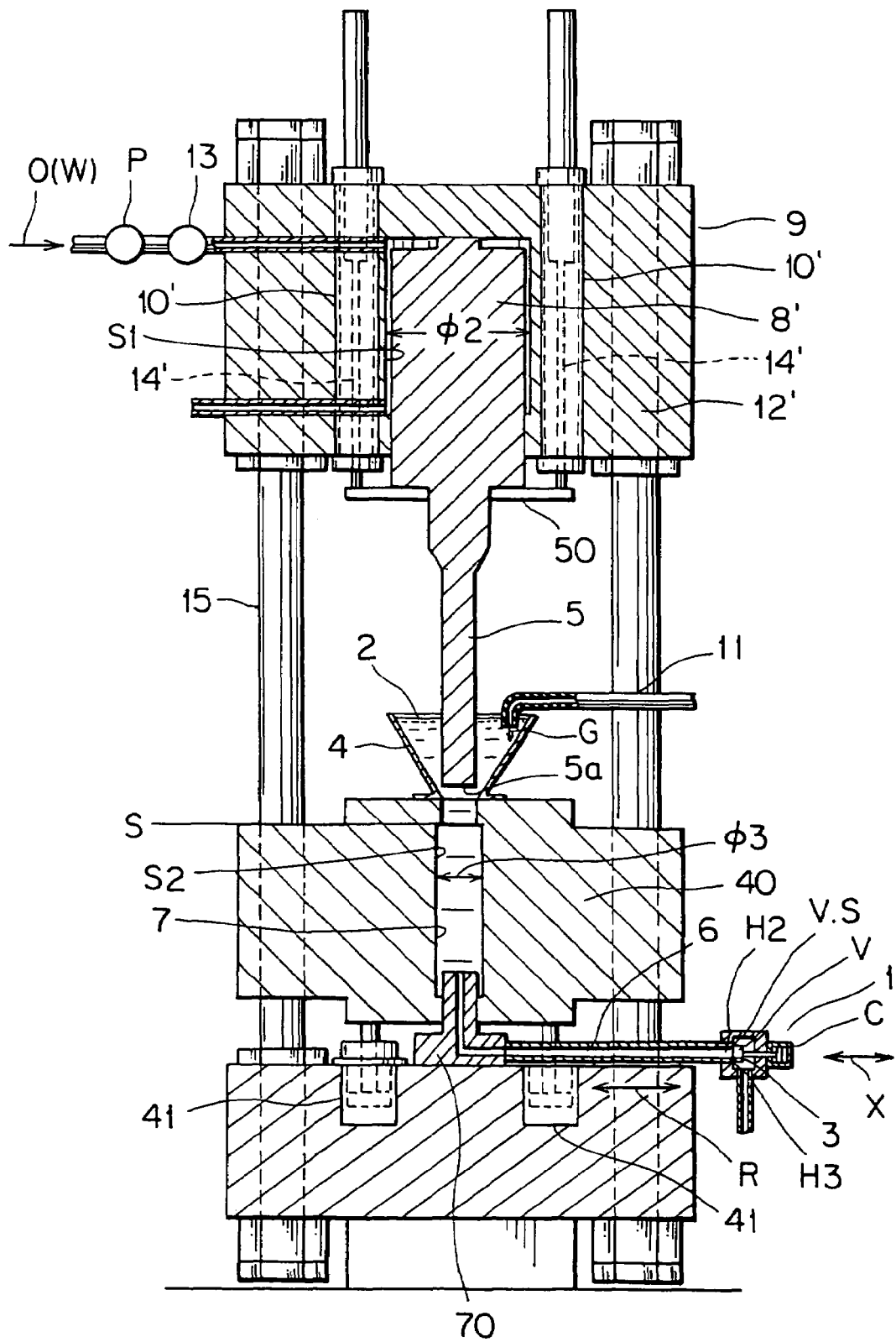
FIG. 29 is a sectional view of a thirteenth embodiment of a homogenizing apparatus of the present invention.
Figure 30:
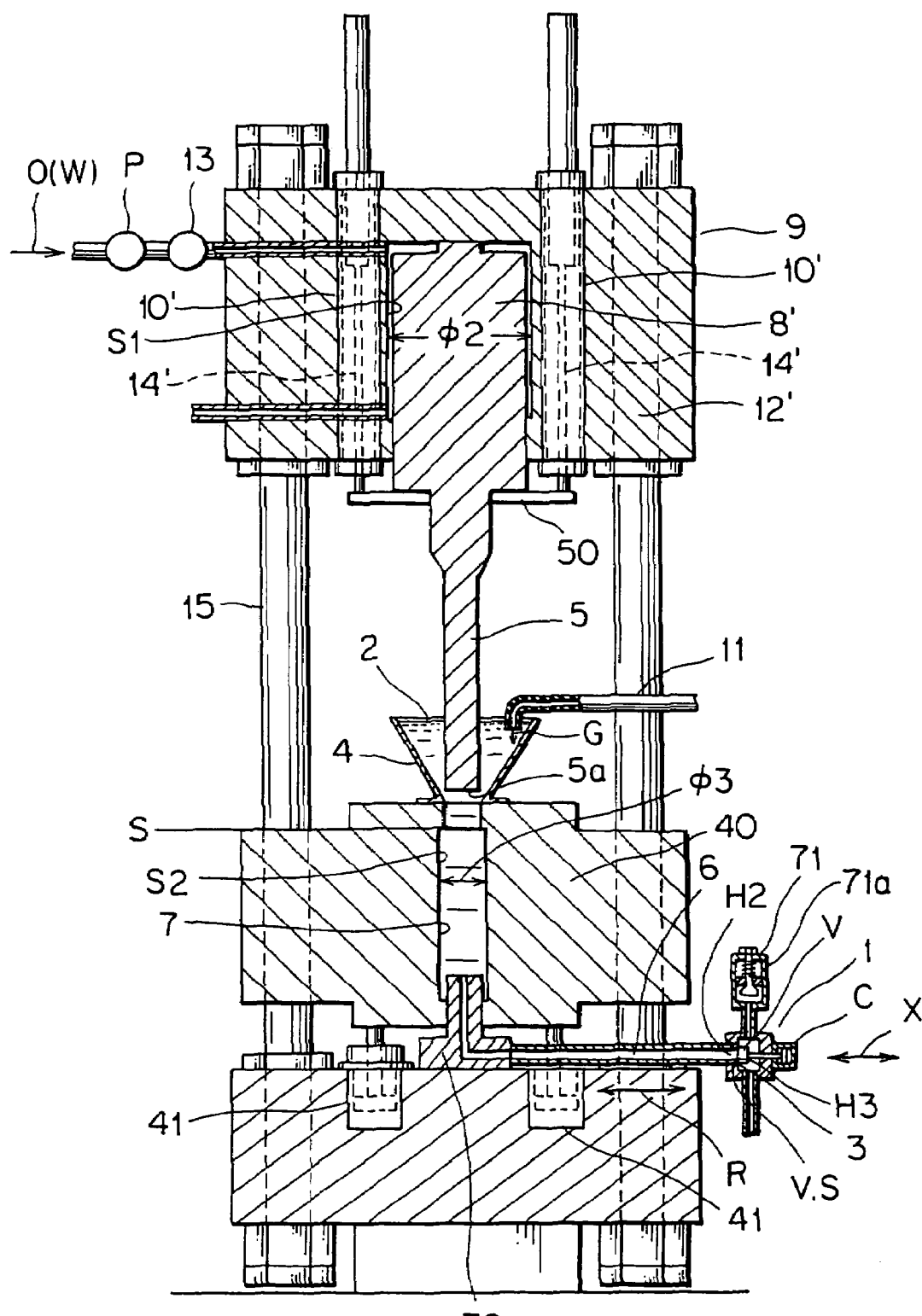
FIG. 30 is a sectional view of a fourteenth embodiment of a homogenizing apparatus of the present invention.
Figure 31:
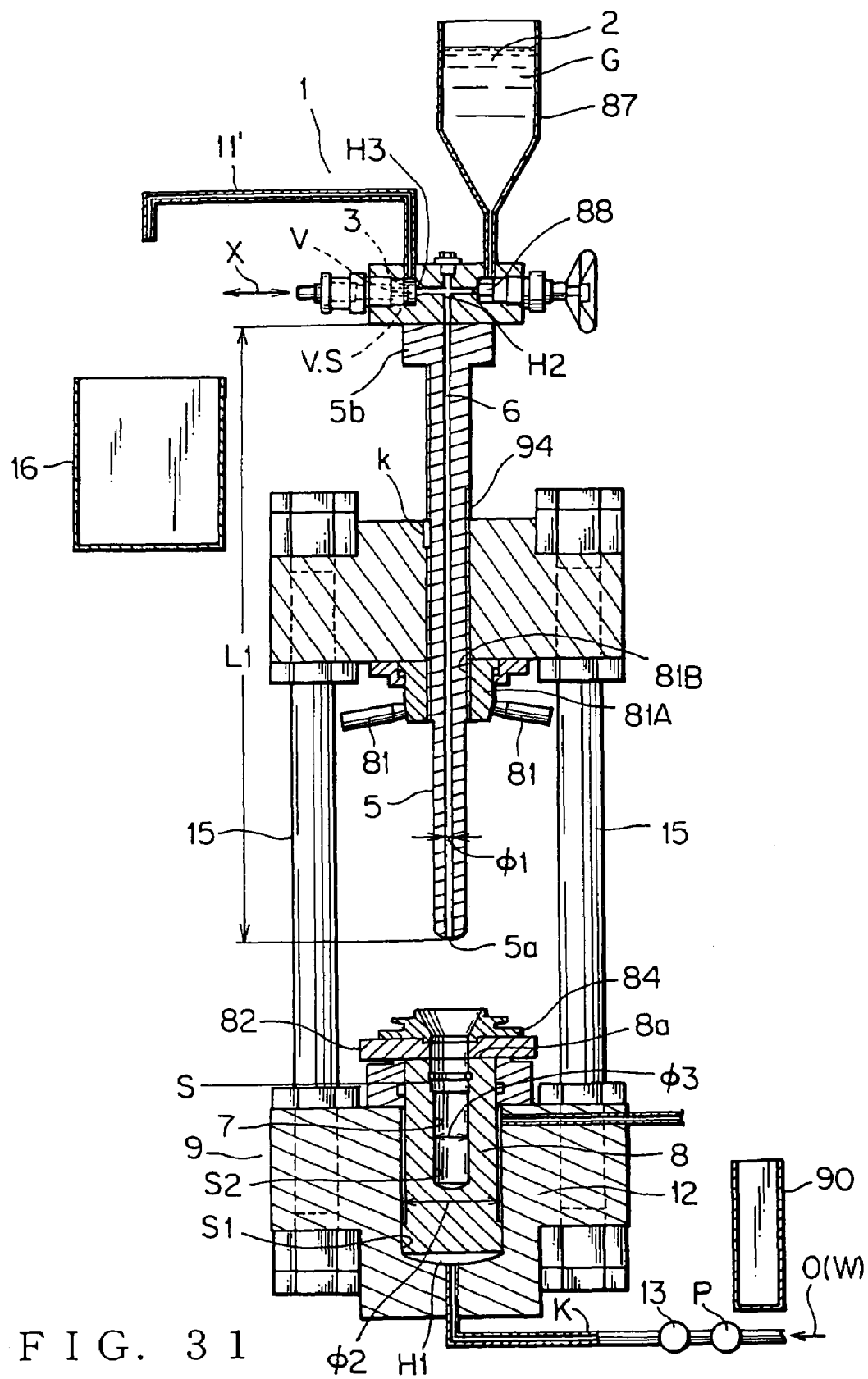
FIG. 31 is a sectional view of a fifteenth embodiment of a homogenizing apparatus of the present invention.
Figure 32:
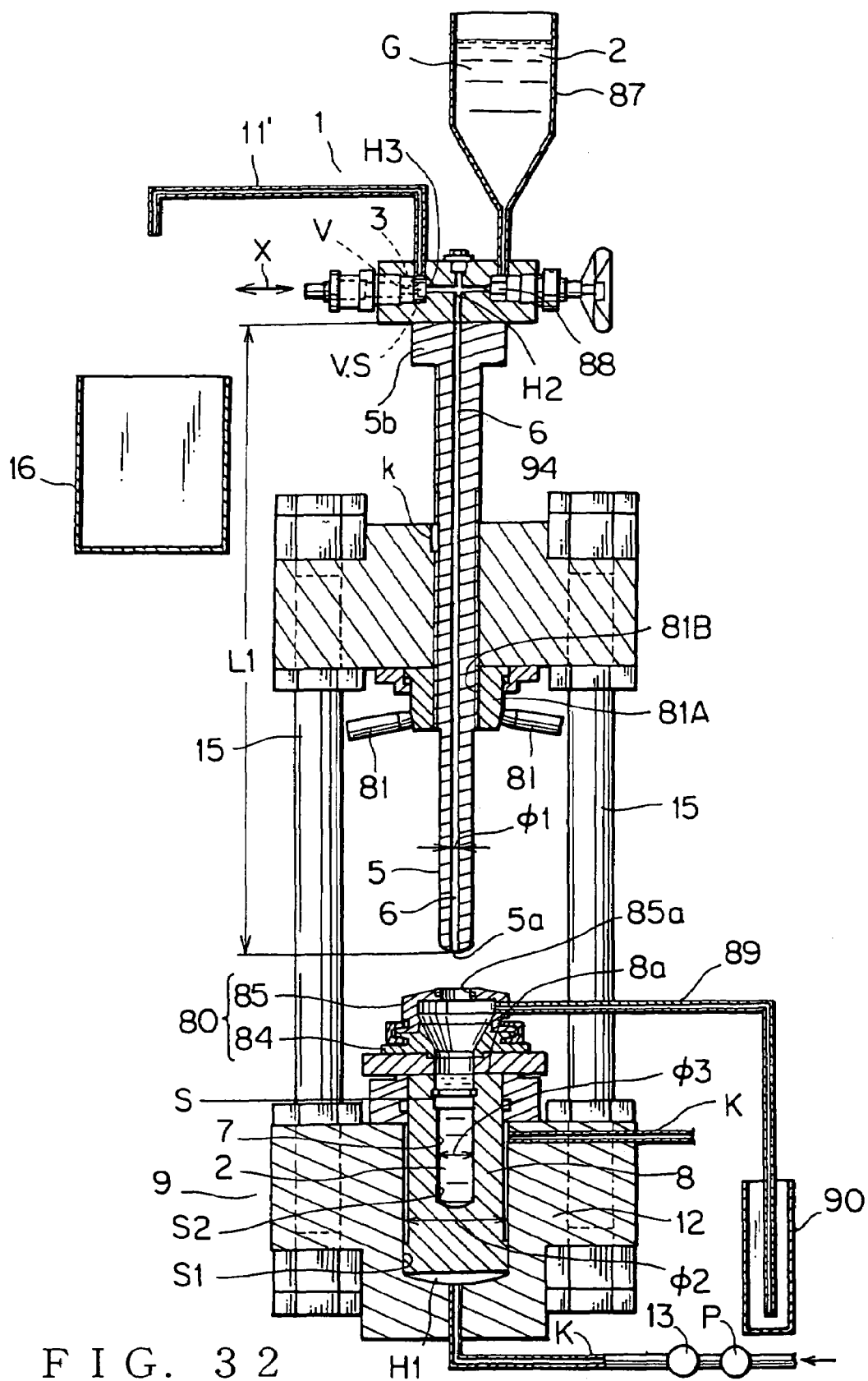
FIG. 32 is a sectional view showing that a suspension is filled into a processing recess over a watertight position as a preliminary step of the fifteenth embodiment.
Figure 33:
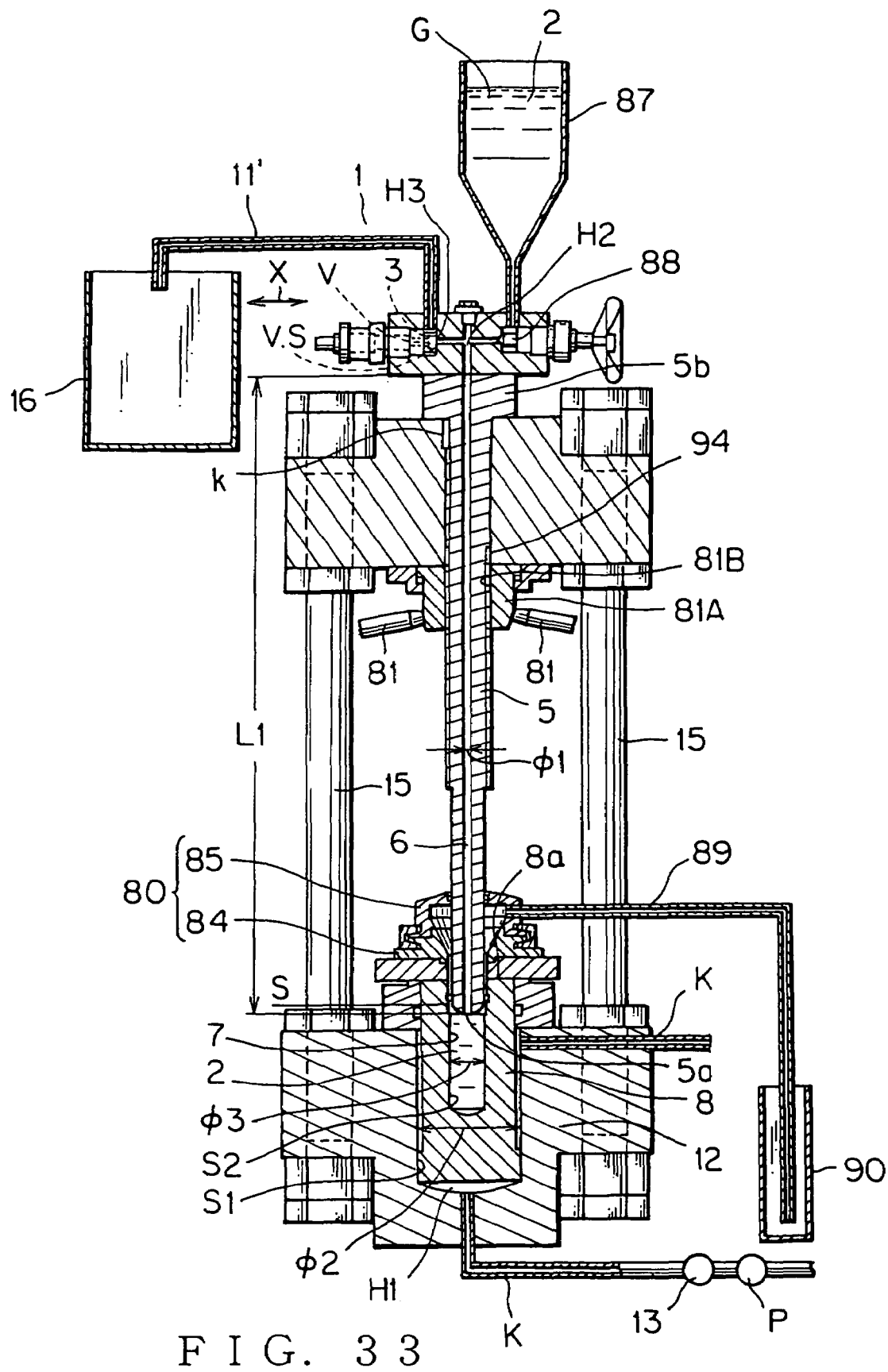
FIG. 33 is a sectional view showing that the suspension is filled in the processing recess over the watertight position and led into a raw material receiving passage of the fifteenth embodiment.

FIGS. 29 and 30 show a thirteenth and fourteenth embodiments, respectively.

Each of the thirteenth and fourteenth embodiments includes a processing piston 5, or a booster piton 8' of a pressure intensifier 9, movable with respect to a frame 15 and a receiver, or a movable cylinder 40 facing to the processing piston 5. The movable cylinder 40 has a processing recess 7 for inserting a front end (one end 5*a*) of the processing piston 5. A raw material receiving passage 6 disposed in a radial direction of the processing recess 7 is connected to a lower end of the processing recess 7 through a bush 70 with T or L (not shown) section. The eleventh embodiment does not have the bush 70. In the thirteenth and fourteenth embodiments, the manufacturing of the raw material receiving passage 6 becomes easy and the assembly and replacement of the parts of the raw material receiving passage 6 to the movable cylinder 40 become easy. Hence, the maintenance and inspection can be made assuredly. The other formation and function are the same as the eleventh embodiment.

As shown in FIG. 30, the fourteenth embodiment has an air inlet valve 71 disposed at the other end of the raw material receiving passage 6. A valve 71*a* is disposed inside the air inlet valve 7 and closed with a spring force. A fine division of a raw material G is achieved by the process described above. After the fine division, when the processing piston 5 is returned to an initial position, the air inlet valve 71 leads an air into the processing recess 7 so as to make the movement of the processing piston 5 easy.

FIGS. 31 to 44 show a fifteenth embodiment.

A high pressure homogenizing apparatus of the fifteenth embodiment passes a suspension 2 containing a raw material G such as fine solid materials, fibrous celluloses, and cell membranes through a small orifice 3 disposed in a high pressure homogenizing device 1 to disperse and emulsify the raw material G or crush, that is, subdivide the cell membranes under high pressure. The high pressure homogenizing apparatus has a raw material receiving passage 6, a processing piston 5, a receiver opposed to the processing piston 5, and a processing recess 7 to receive a front end (one end) 5*a* of the processing piston 5 by means of a pressure intensifier 9. When the pressure intensifier 9 is driven, the receiver and/or the processing piston 5 moves relatively and the suspension 2 flows into the raw material receiving passage 6 with a desired amount to be processed by a compression in the processing recess 7. The solid materials, fibrous celluloses, and cells in the suspension 2 are finely divided at the orifice 3 of the high pressure homogenizing device 1. The process is the same as those of the first to third embodiments.

In the first to third embodiments, the cylinder 10 to move the booster piston 8 is disposed at the upper portion of the frame 15. In the fifteenth embodiment, in place of that, a hydraulic or water pressure circuit K is disposed inside a booster cylinder 12 of the pressure intensifier 9 similarly to the fourth embodiment shown in FIG. 19. A booster piston 8 is moved toward the processing piston 5 with the pressure and the front end (the one end 5*a*) of the processing piston 5 is inserted into the processing recess 7 through a hopper 4. When the processing piston 5 passes through a watertight position S in the processing recess 7 and pressurizes the processing recess 7, the suspension 2 containing the raw material G is led into the raw material receiving passage 6 and pressurized to a high pressure H2. The booster piston 8 is returned to an initial position by changing the hydraulic or water pressure of the circuit K.

However, in the fifteenth embodiment, the suspension 2 containing the raw material G, such as fine solid materials, fibrous celluloses, or cells, is filled into the processing recess 7 over the watertight position S before fine division as a preliminary step.

First of all, a cover 80 (refer to FIG. 31) is removed from the receiver. The cover 80 is usually placed above the receiver to close the processing recess 7 and has a hole for inserting the processing piston 5 slidably and is detachable to the receiver.

The suspension 2 containing the raw material G is filled into the processing recess 7 over the watertight position S. The suspension 2 can be filled into the processing recess 7 manually or automatically.

The cover 80 is returned to close the processing recess 7. A handle 81 disposed around the processing piston 5 is rotated. The handle 81 is threadably mounted on the processing piston 5 by a screw disposed inside a boss 81*a* of the handle 81 and a screw 94 disposed in the circumference along the axial direction of the processing piston 5. The processing piston 5 is manually moved into the processing recess 7 through the cover 80. The processing piston 5 is prohibited from rotating by a key k. The processing piston 5 is moved to pass through the watertight position S of the processing recess 7 so that the suspension 2 is filled in the raw material receiving passage 6 as an initial position.

As shown in FIGS. 38 to 44, the cover 80 includes a fixing plate 82 disposed above the receiver having the processing recess 7, an annular cover main body 84 fixed to an upper surface of the fixing plate 82 with bolts 83 and having a first locking edge 84*a* around the cover main body 84, a through-hole 85*a* for inserting the processing piston 5, an upper cover 85 having a second locking edge 85*b* to be contacted with the first locking edge 84*a* of the cover main body 84, and collars 86 separated in two parts to hold the first and second locking edges 84*a* and 85*b* and having fitting processing recesses 86*a*. The upper cover 85 is attached removably to the cover main body 84 with the collars 86, which are fastened by bolts 86A.

The cover 80 is utilized for preventing the raw material G from scattering to a surrounding area during fine dividing process. The high pressure homogenizing apparatus can be easily cleaned and the maintenance and control such as replacement of parts can also be easily performed.

The apparatus has a hopper 87 to supply the raw material G and a valve 88, which is disposed between the hopper 87 and the raw material receiving passage 6. The valve 88 can be operated manually or automatically (not shown).

One end of an overflow pipe 89 is attached to one side of the upper cover 85 and the other end of the overflow pipe 89 is led into a reservoir 90 to keep the overflowed raw material G. The overflow pipe 89 may have a valve (not shown) to keep the inside of the processing recess 7 watertight.

The following steps are performed in order for finely dividing the raw material G in the fifteenth embodiment. The suspension 2 containing the raw material G is supplied to the processing recess 7 over the watertight position S (refer to FIGS. 31 to 33).

Figure 34:
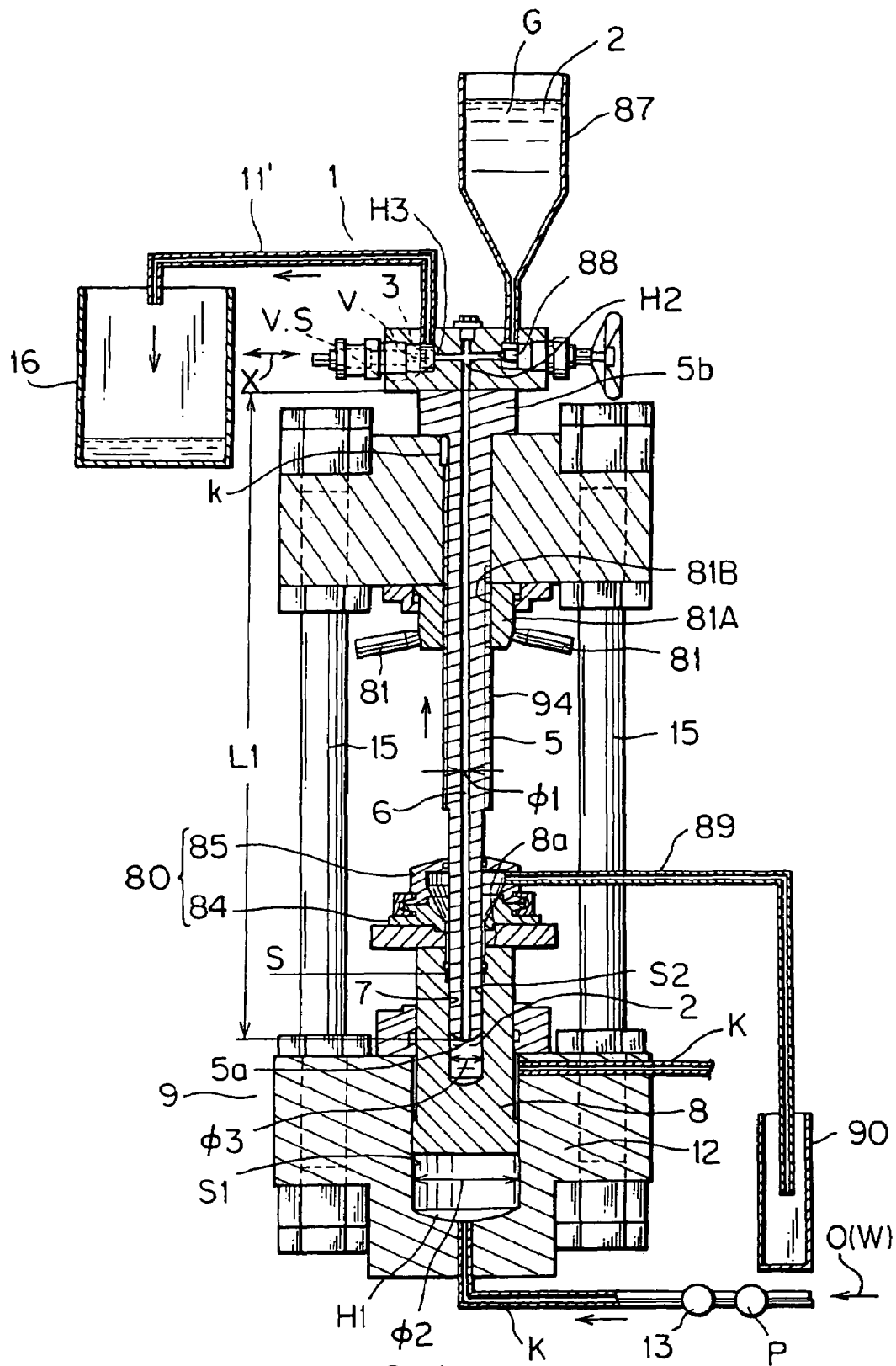
FIG. 34 is a sectional view showing that the suspension is filled in the processing recess over the watertight position and pressurized in the raw material receiving passage of the fifteenth embodiment.
Figure 35:
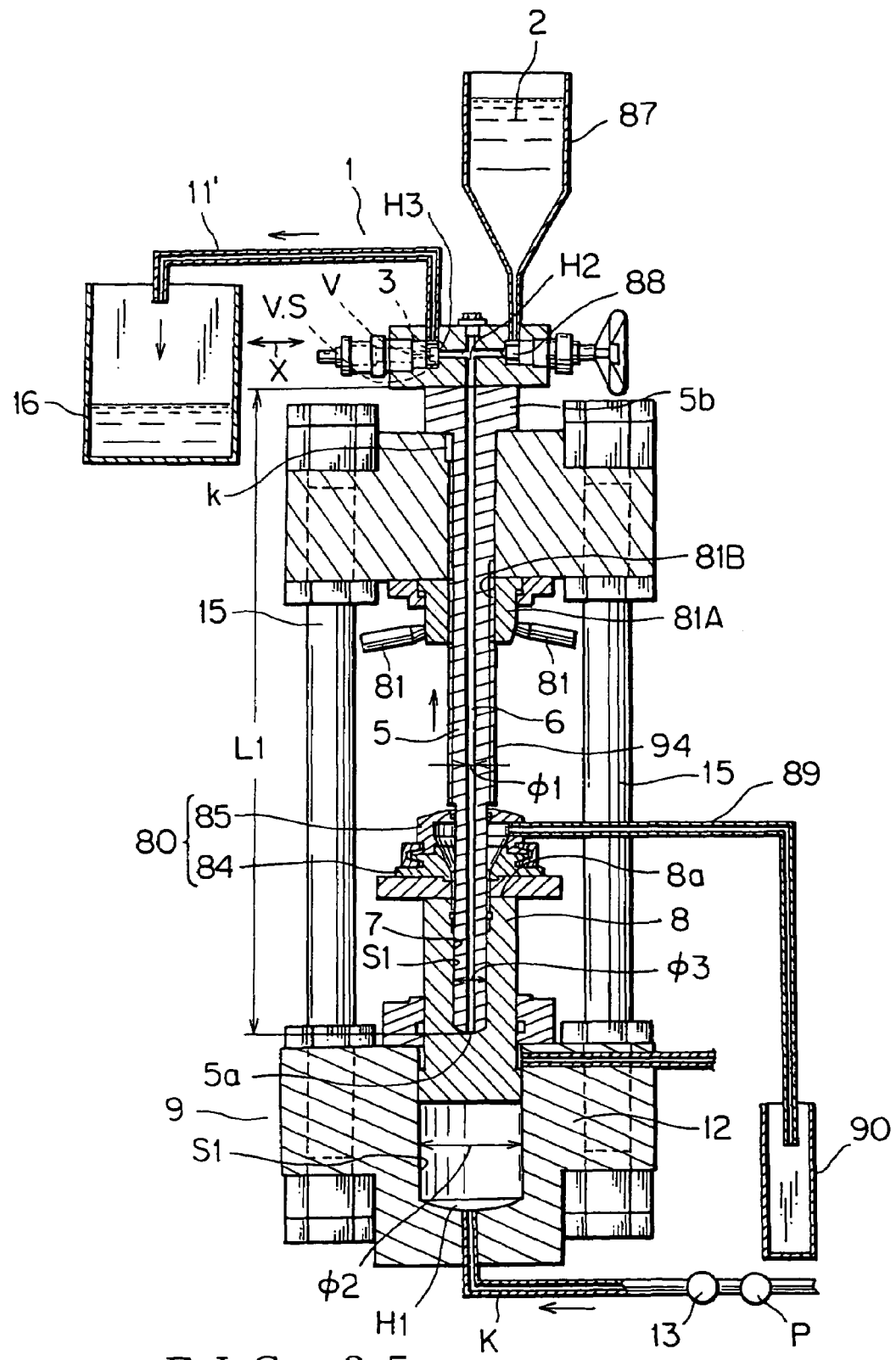
FIG. 35 is a sectional view showing that the suspension is filled in the processing recess over the watertight position, pressurized in the raw material receiving passage, and subdivided.
Figure 36:
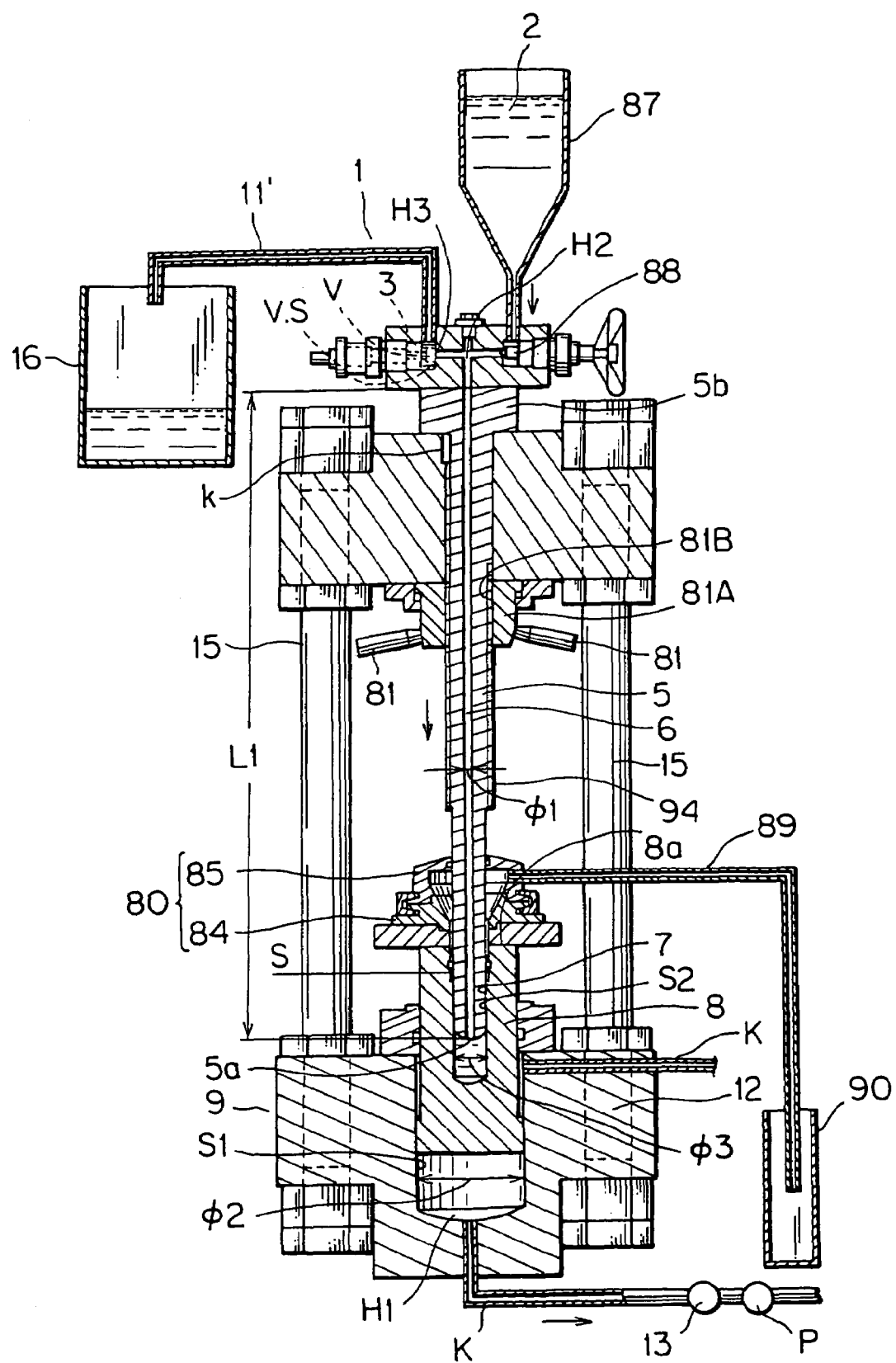
FIG. 36 is a sectional view showing that the suspension is led into the processing recess of the processing piston after a fine division of a raw material of the fifteenth embodiment.
Figure 37:
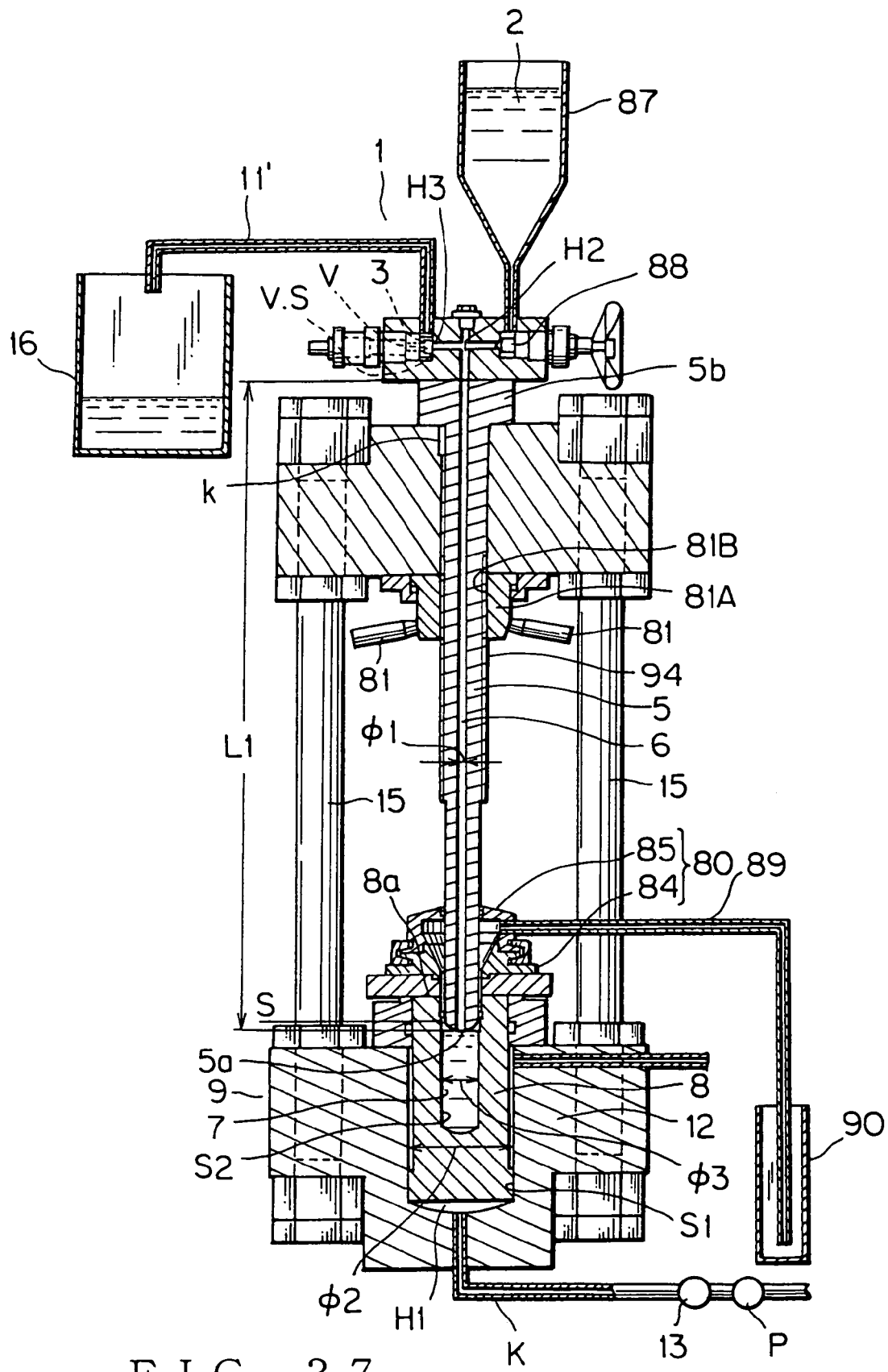
FIG. 37 is a sectional view showing that the supply of the suspension into the processing recess of the processing piston is finished after the fine division of the raw material of the fifteenth embodiment.
Figure 38:
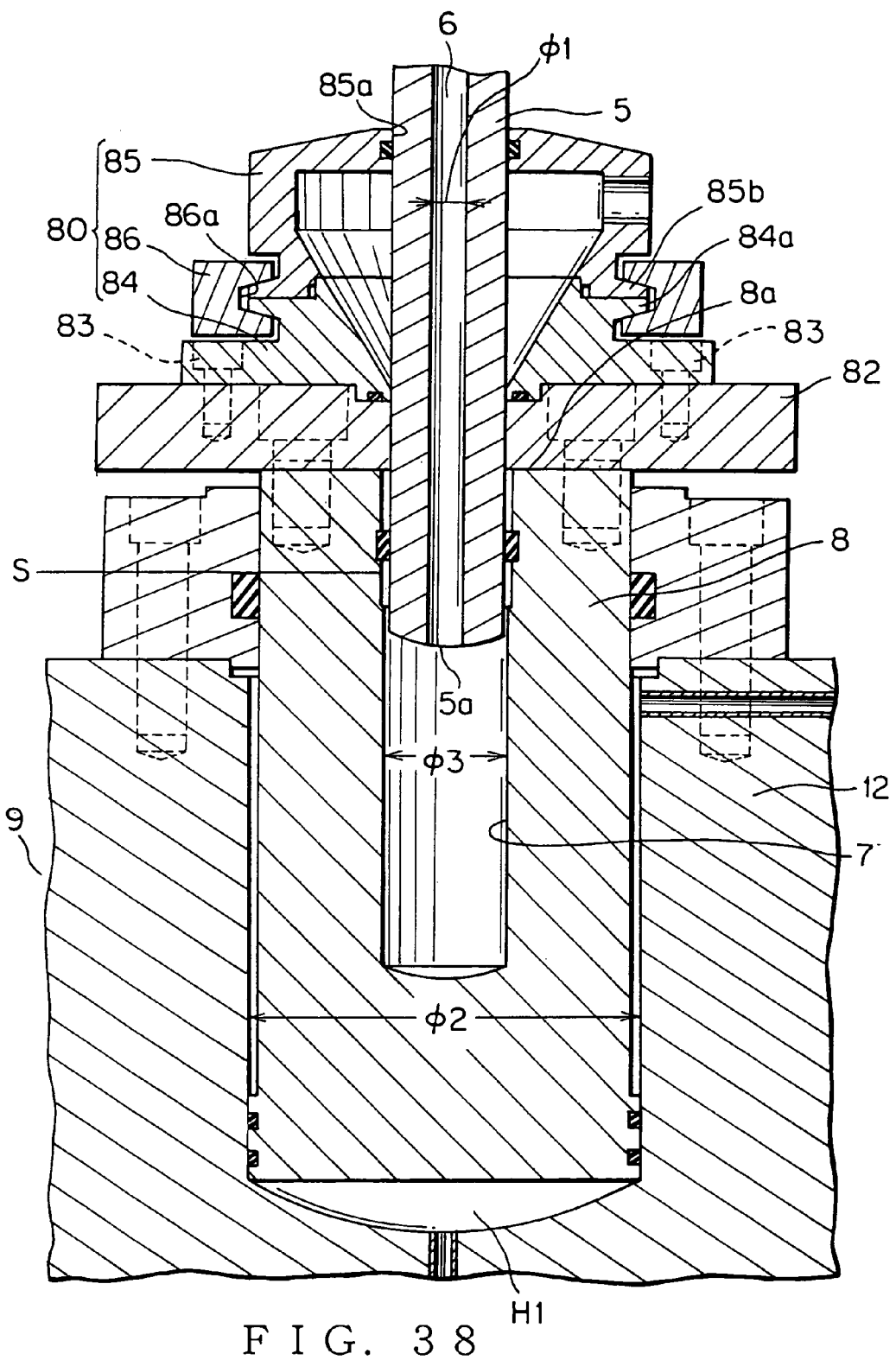
FIG. 38 is an expanded sectional view of the fifteenth embodiment.
Figure 41:
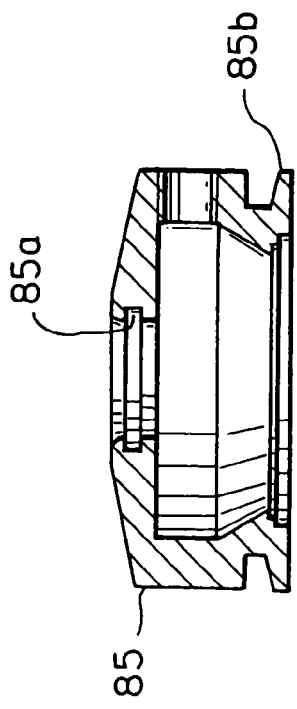
FIG. 41 is an expanded sectional view of an upper cover of the cover of the fifteenth embodiment.
Figure 42:
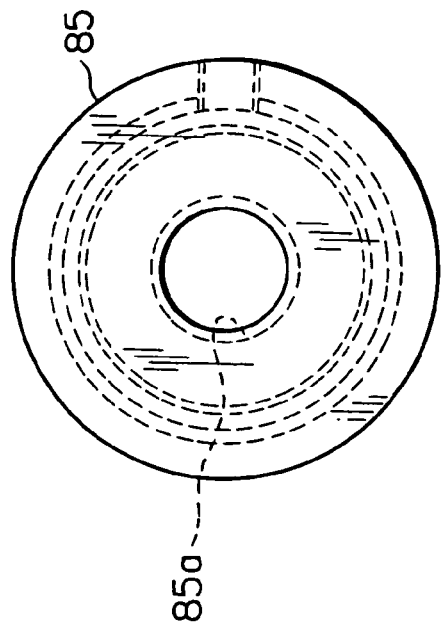
FIG. 42 is an expanded plan view of the upper cover of the fifteenth embodiment.
Figure 39:
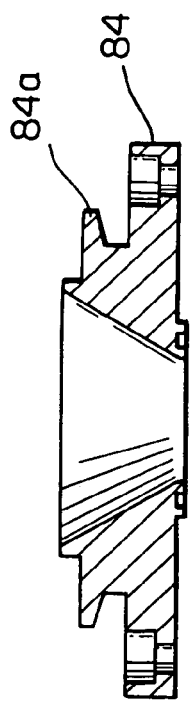
FIG. 39 is an expanded sectional view of a cover main body of a cover of the fifteenth embodiment.
Figure 40:
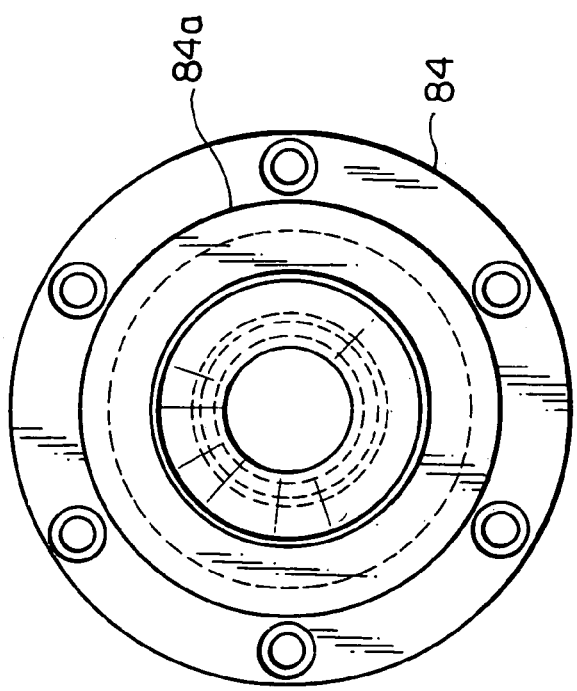
FIG. 40 is an expanded plan view of the cover main body of the fifteenth embodiment.
Figure 43:
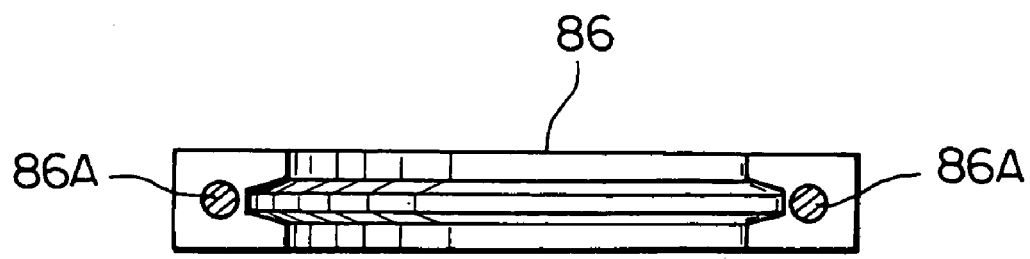
FIG. 43 is an expanded sectional view of collars of the fifteenth embodiment.
Figure 44:
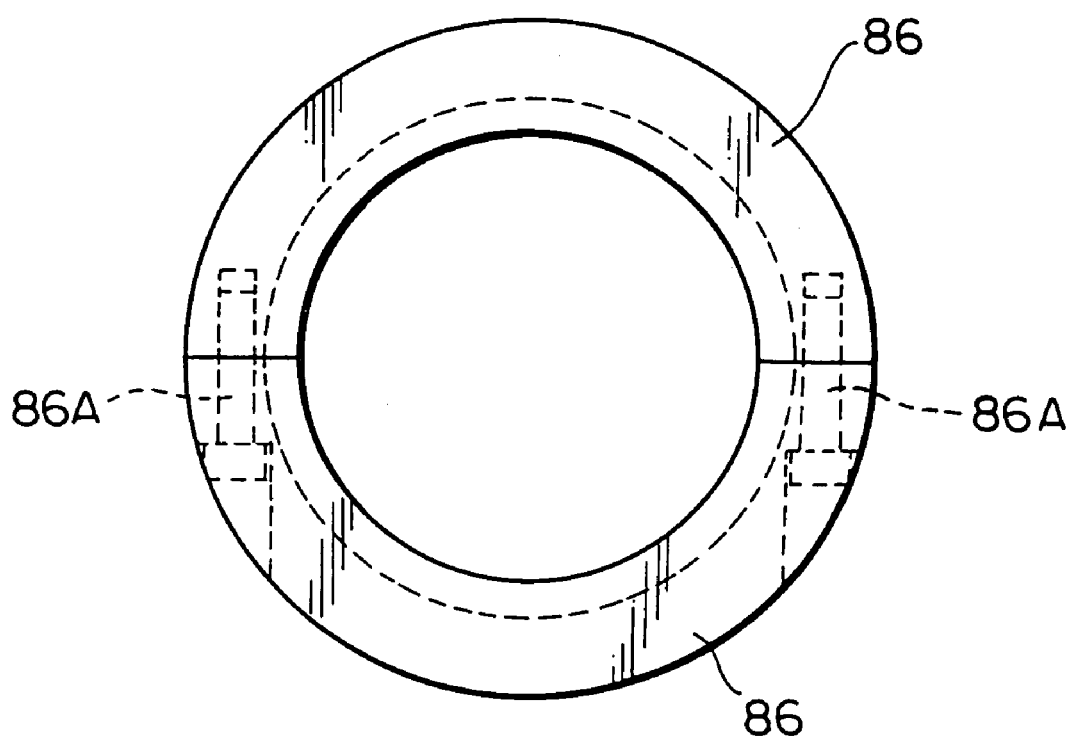
FIG. 44 is an expanded plan view of the collars of the fifteenth embodiment.

The pressure intensifier 9 is driven so that the processing piston 5 is inserted into the processing recess 7 and the front end 5*a* thereof is passed through the watertight position S and the processing recess 7 is pressurized (refer to FIG. 34). At this time, the valve 88 at the hopper 87 stops to supply the suspension 2 to the raw material receiving passage 6.

The volume compression inside the processing recess 7 caused by the insertion of the processing piston 5 results in leading the suspension 2 to the raw material receiving passage 6 with a desired amount.

The suspension 2 is further pressurized in the raw material receiving passage 6 and is passed through the orifice 3 at high speed so that the solid material, fibrous celluloses, or cells are finely divided into the dispersion, emulsification, or crushing of cell membranes (refer to FIG. 35), respectively.

When the booster piston 8 is moved downwardly to the initial position after the fine division of the raw material G, the increase of the volume inside the processing recess 7 leads the suspension 2 into the processing recess 7 and fills it over the watertight position S. The valve 88 is opened to supply the suspension 2 from the hopper 87. This function makes the high pressure homogenizing device 1 possible of an automatic operation for the fine division of the raw material G. The automatic supply of the suspension 2 into the processing recess 7 is suitable for finely dividing fluent materials containing the dispersion or emulsification of the solid material, fibrous cellulose, or cells.

The cover 80 is mounted detachably on the upper surface of the booster piston 8 so that the cleaning inside of the processing recess 7 and the replacement of the parts are easily made, and the maintenance and control are also easily made. The other formation and function are the same as the other embodiments. The booster piston 8 is moved up and down by the circuits K of oil or water pressures but can be moved by any other means. In the above embodiment, a pressing force of a homogenizing valve V to a valve seat V.S is adjusted automatically with the oil pressure cylinder. In this embodiment, the adjustment of the pressing force of the homogenizing valve V can be automatic or manual.

Figure 46:
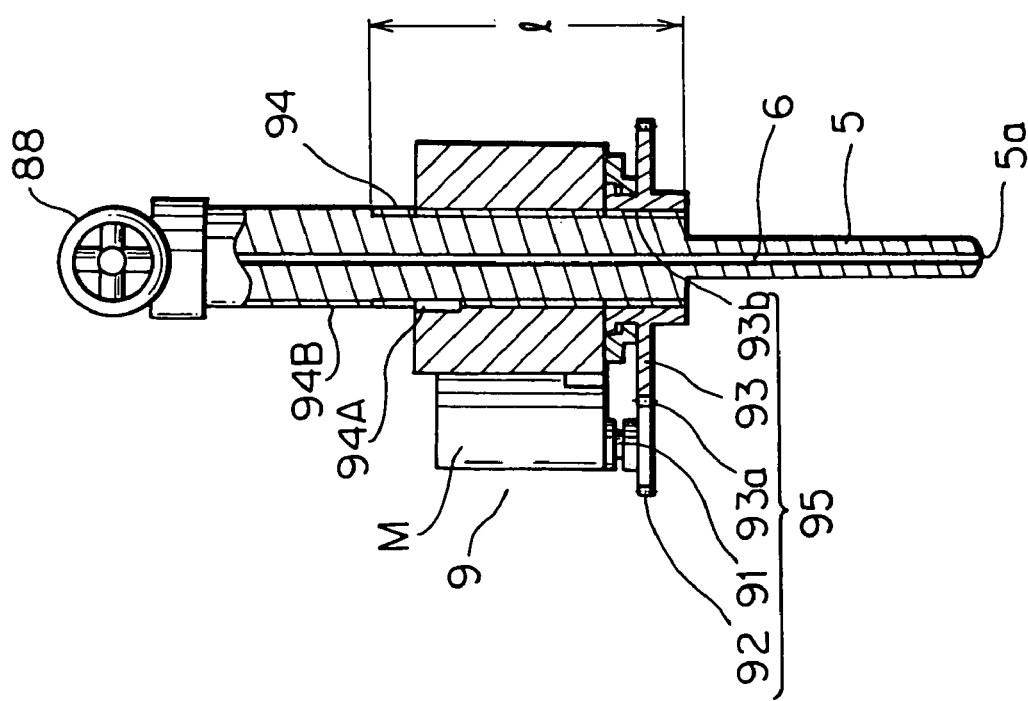
FIG. 46 is a sectional view when viewed from a side of the sixteenth embodiment.

FIGS. 45 and 46 are a sixteenth embodiment of the present invention. The sixteenth embodiment includes a cylinder 8" having a processing recess 7 at an upper face thereof and fixed to a lower portion of a frame 15, and a processing piston 5 of a pressure intensifier 9 disposed at an upper position of the frame 15. This arrangement is contrary to the fifteenth embodiment shown in FIGS. 31 to 44. The formation and function are the same as the seventh embodiment (FIG. 22) and the tenth embodiment (FIG. 25).

In the sixteenth embodiment, the pressure intensifier 9 to move and return the processing piston 5 into and from the processing recess 7 includes a motor M, a gear group 95 having a drive gear 92 connected with a motor shaft 91, a gear tooth 93a disposed at an outer circumference of an annular driven gear 93 and engaging with the drive gear 92, and a gear tooth 93b disposed at an inner circumference of the driven gear 93 and engaging with a screw 94 disposed at an outer wall of the processing piston 5, where the driven gear 93 is rotatable around the processing piston 5, a key groove 94A disposed at the outer wall of the processing piston 5 and intersecting with the screw 94 in the axial direction, and a key 94B to be inserted into the key groove 94A.

As similarly to the fifteenth embodiment, a cover 80 is removed from an upper cover 85 and a suspension 2 is filled in the processing recess 7 over a watertight position S as a preliminary step.

The upper cover 85 is returned to close the upper face of the processing recess 7. After that, the drive gear 92 is driven by the motor M so that the driven gear 93 is rotated. The gear tooth 93b disposed at the inner circumference of the driven gear 93 engages with the screw 94. Accordingly, the processing piston 5 locked by the key 94B in the key groove 94A to be rotated is moved downwardly and inserted into the processing recess 7. When a front end 5a passes through the watertight position S, the suspension 2 is pressurized further.

When the processing piston 5 is further moved downwardly, the volume compression inside the processing recess 7 presses and flow the suspension 2 into the raw material receiving passage 6 with the desired amount. The processing piston 5 is further moved downwardly to pressurize the suspension 2 to high pressure so that the suspension 2 is passed through an orifice 3 at high speed to finely divide a raw material G of the solid material, fibrous cellulose, or cells.

After the fine division, the processing piston 5 is returned to an initial position by means of the gear group 95 driven by the motor M. When the processing piston 5 is returned to the initial position, the increase volume inside the processing recess 7 leads the suspension 2 into the processing recess 7 from a hopper 8 and the suspension 2 is filled in the processing recess 7 over the watertight position S.

After every fine division, the suspension 2 is supplied to the processing recess 7 from the hopper 87 with a valve 88 opened by virtue of the increase of the volume inside the processing recess 7. The formation and function are the same as the fifteenth embodiment.

Figure 48:
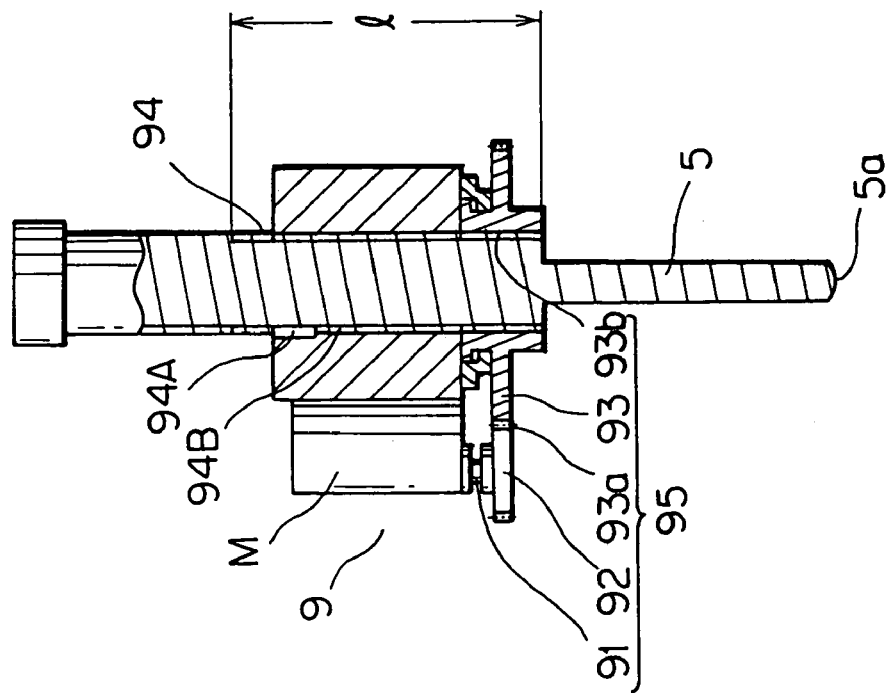
FIG. 48 is a sectional view when viewed from a side of the seventeenth embodiment.

FIGS. 47 and 48 show a seventeenth embodiment of the present invention.

The seventeenth embodiment includes a cylinder 8" having a processing recess 7 disposed at an upper face 8" a thereof and for inserting a front end 5a of a processing piston 5 through a watertight position S, and a raw material receiving passage 6 disposed inside the cylinder 8", and a hopper 87 disposed in a radial direction R of the cylinder 8" and for supplying a suspension 2 to the processing recess 7. The processing recess 7 is communicated with a high pressure homogenizing device 1 having a homogenizing valve V to finely divide a raw material G so that the suspension 2 is supplied to the processing recess 7 and the processing piston 5 is moved downwardly to pressurize and subdivide the raw material G.

In the seventeenth embodiment, after removing an upper cover 85, the suspension 2 containing the raw material G is filled manually into the processing recess 7 over the watertight position S.

The upper cover 85 is returned to close the upper face of the processing recess 7. After that, a drive gear 92 is driven by a motor M so that a driven gear 93 disposed around the processing piston 5 is rotated with an engagement of the drive gear 92 with a gear tooth 93a. The processing piston 5 having a screw 94 at an outer circumference thereof engaging with the driven gear 93 is moved downwardly into the processing recess 7. When the front end 5a passes through the watertight position S, the suspension 2 is pressurized further.

When the processing piston 5 is further moved downwardly, the volume compression inside the processing recess 7 presses and flow the suspension 2 into the raw material receiving passage 6 with the desired amount. The processing piston 5 is further moved downwardly to pressurize the suspension 2 to high pressure so that the suspension 2 is passed through an orifice 3 at high speed to finely divide the raw material G of the solid material, fibrous cellulose, or cells.

After the fine division, the processing piston 5 is returned to an initial position by means of a gear group 95 driven by the motor M. When the processing piston 5 is returned to the initial position, the increase volume inside the processing recess 7 leads the suspension 2 into the processing recess 7 from a hopper 8 and the suspension 2 is filled in the processing recess 7 over the watertight position S.

After every fine division, the suspension 2 is supplied to the processing recess 7 from the hopper 87 with a valve 88 opened by virtue of the increase of the volume inside the processing recess 7. The other formations and functions are the same as the tenth embodiment of FIG. 25, the eleventh embodiment of FIG. 26, the twelfth embodiment of FIGS. 27 and 28, and the sixteenth embodiment of FIGS. 44 and 45.

FIGS. 49 to 55 show an eighteenth embodiment of the present invention.

In the sixteenth embodiment shown in FIGS. 45 and 46, the suspension 2 is filled into manually the processing recess 7 over the watertight position S after removing the cover 80. After covering the processing recess 7 with the cover 80, the processing piston 5 is moved downwardly into the processing recess 7 through the cover 80 and passed over the watertight position S manually to set up the initial position.

Figure 49:
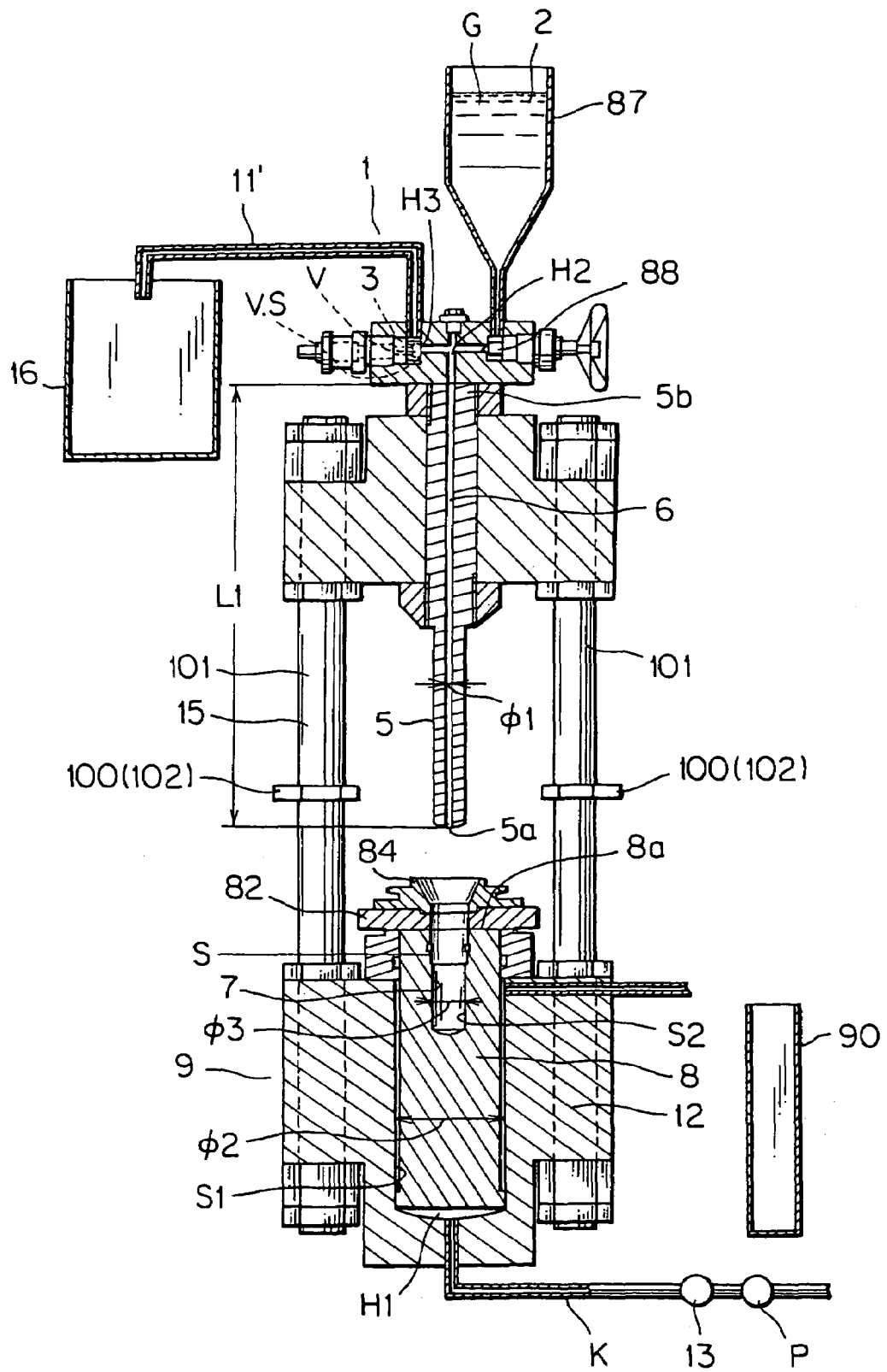
FIG. 49 is a sectional view of an eighteenth embodiment of a homogenizing apparatus of the present invention.
Figure 50:
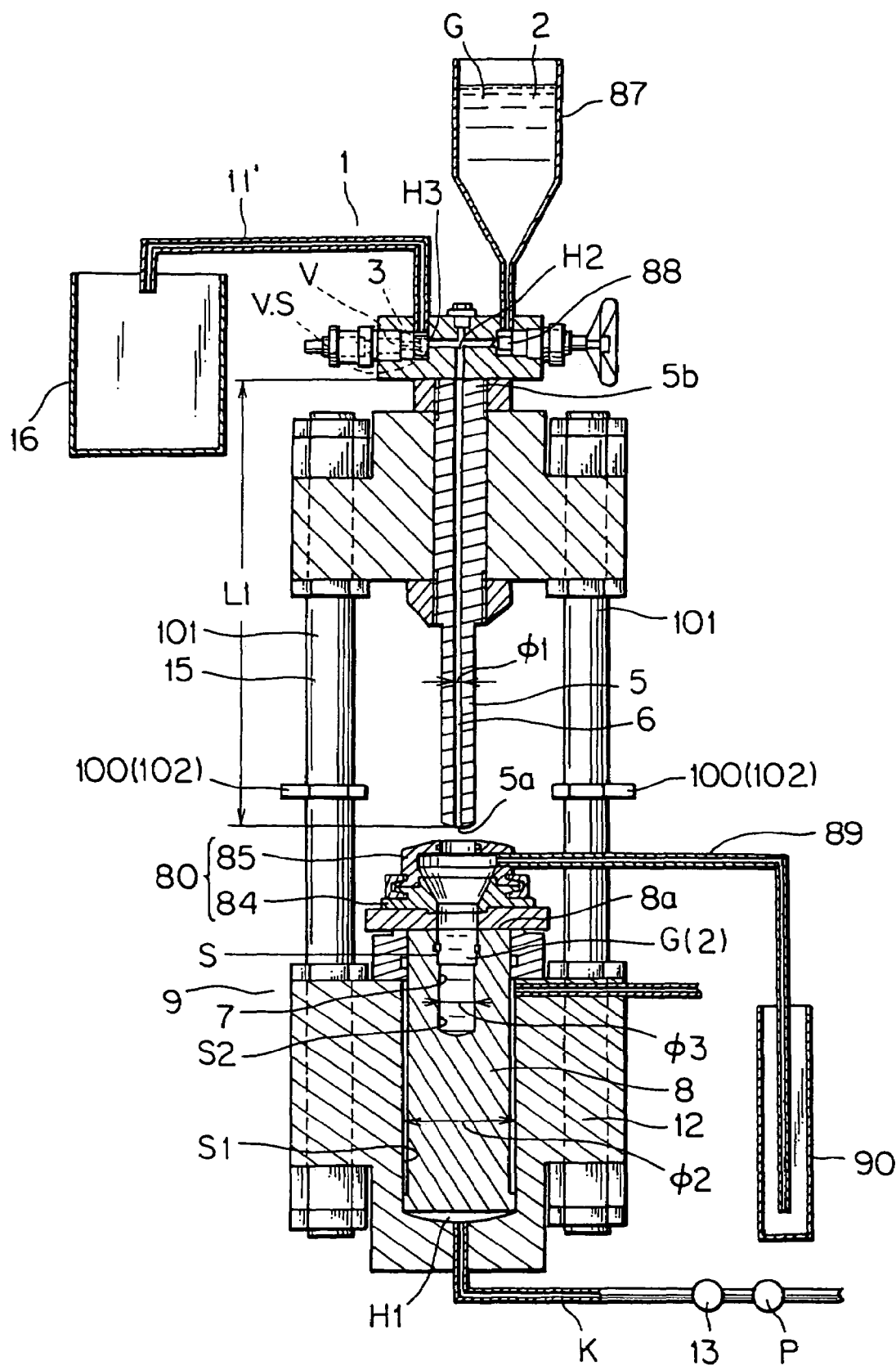
FIG. 50 is a sectional view showing that a suspension is filled into a processing recess over a watertight position as a preliminary step of the eighteenth embodiment.

In the eighteenth embodiment, a cover 80 is covered to a processing recess 7 after a suspension 2 is filled into the processing recess 7 over a watertight position S (refer to FIGS. 49 and 50).

Figure 51:
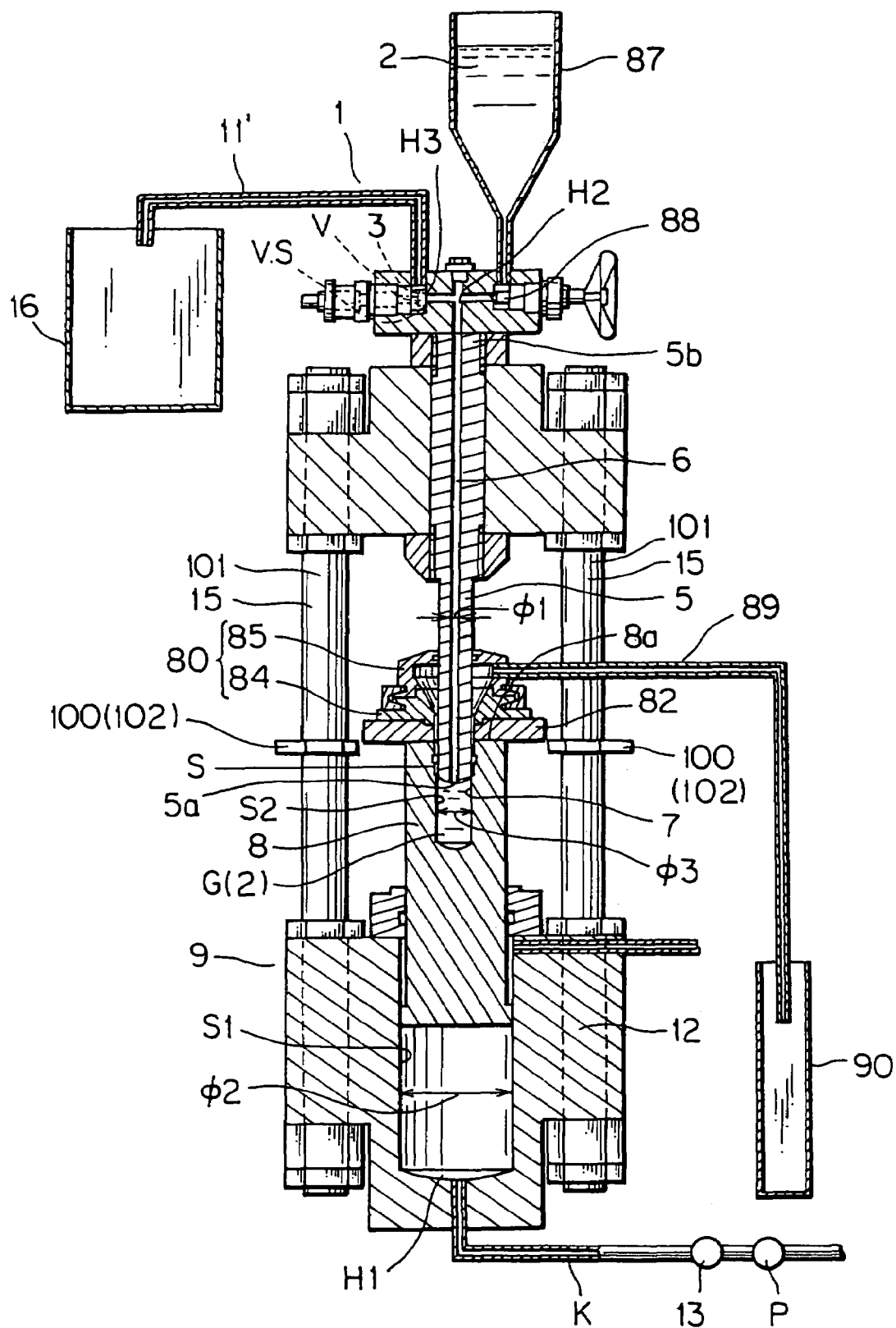
FIG. 51 is a sectional view showing that the suspension is filled over the watertight position in the processing recess and led into a raw material receiving passage of the eighteenth embodiment.
Figure 52:
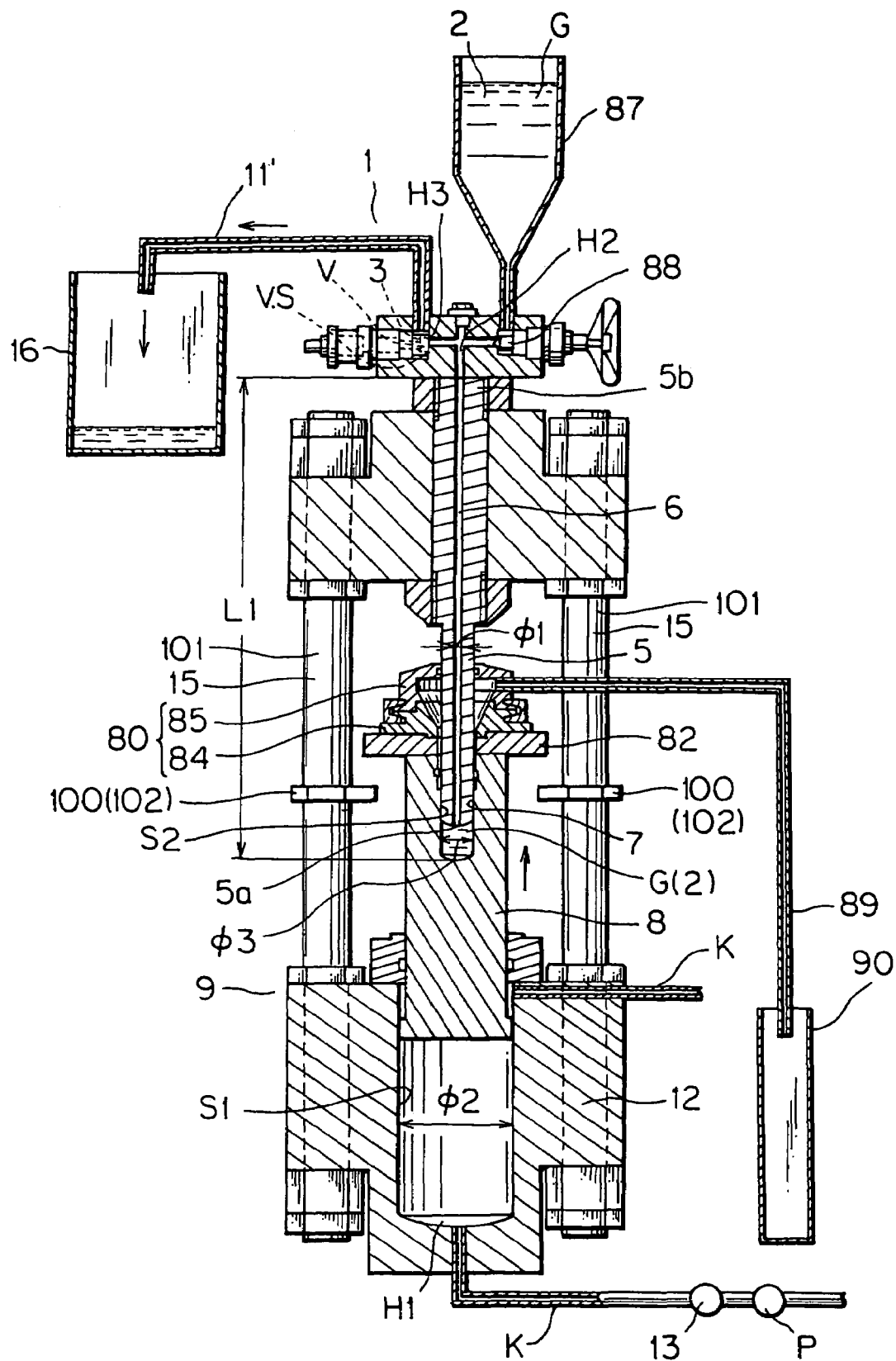
FIG. 52 is a sectional view showing that the suspension is filled over the watertight position and pressurized further in the raw material receiving passage of the eighteenth embodiment.

When a processing piston 5 is further moved downwardly, the volume compression inside the processing recess 7 pressurizes and flows the suspension 2 into a raw material receiving passage 6 with the desired amount (refer to FIGS. 51 and 52).

Figure 53:
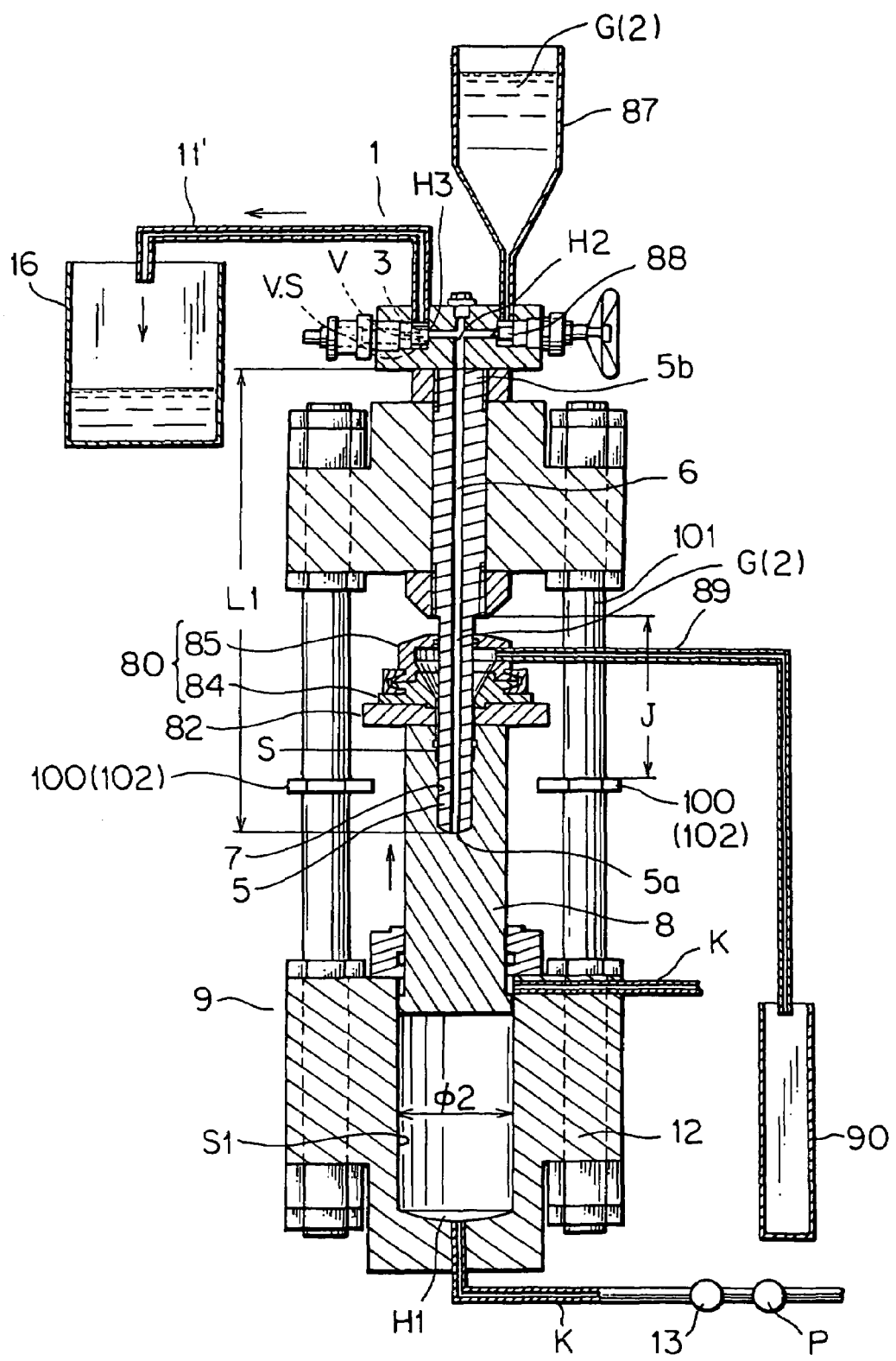
FIG. 53 is a sectional view of the eighteenth embodiment showing that the suspension is further pressurized in the processing recess and a raw material in the suspension is finely divided.
Figure 54:
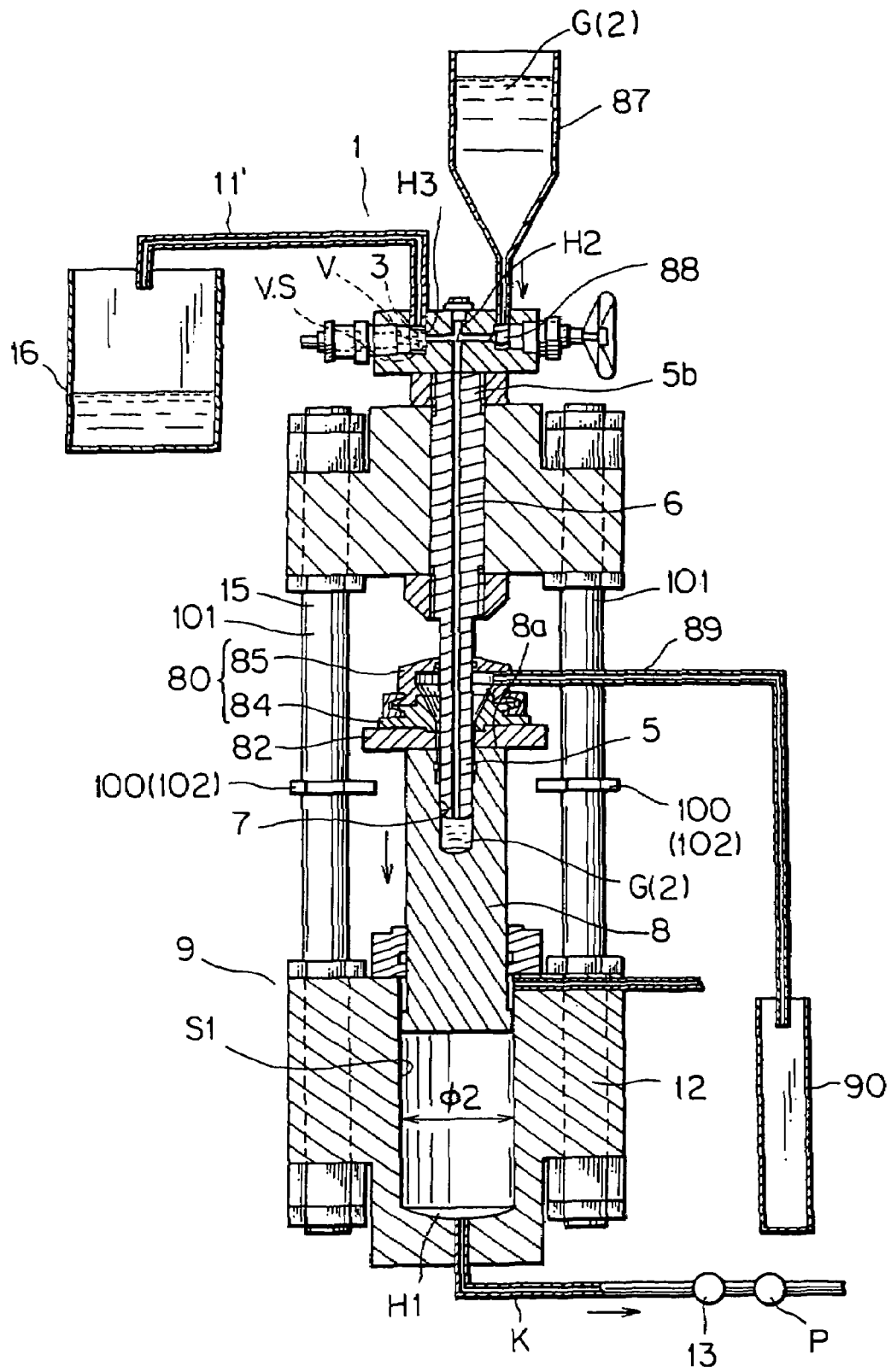
FIG. 54 is a sectional view showing that a processing piston is returned to an initial position and the suspension is led into the processing recess after the fine division of the raw material of the eighteenth embodiment.
Figure 55:
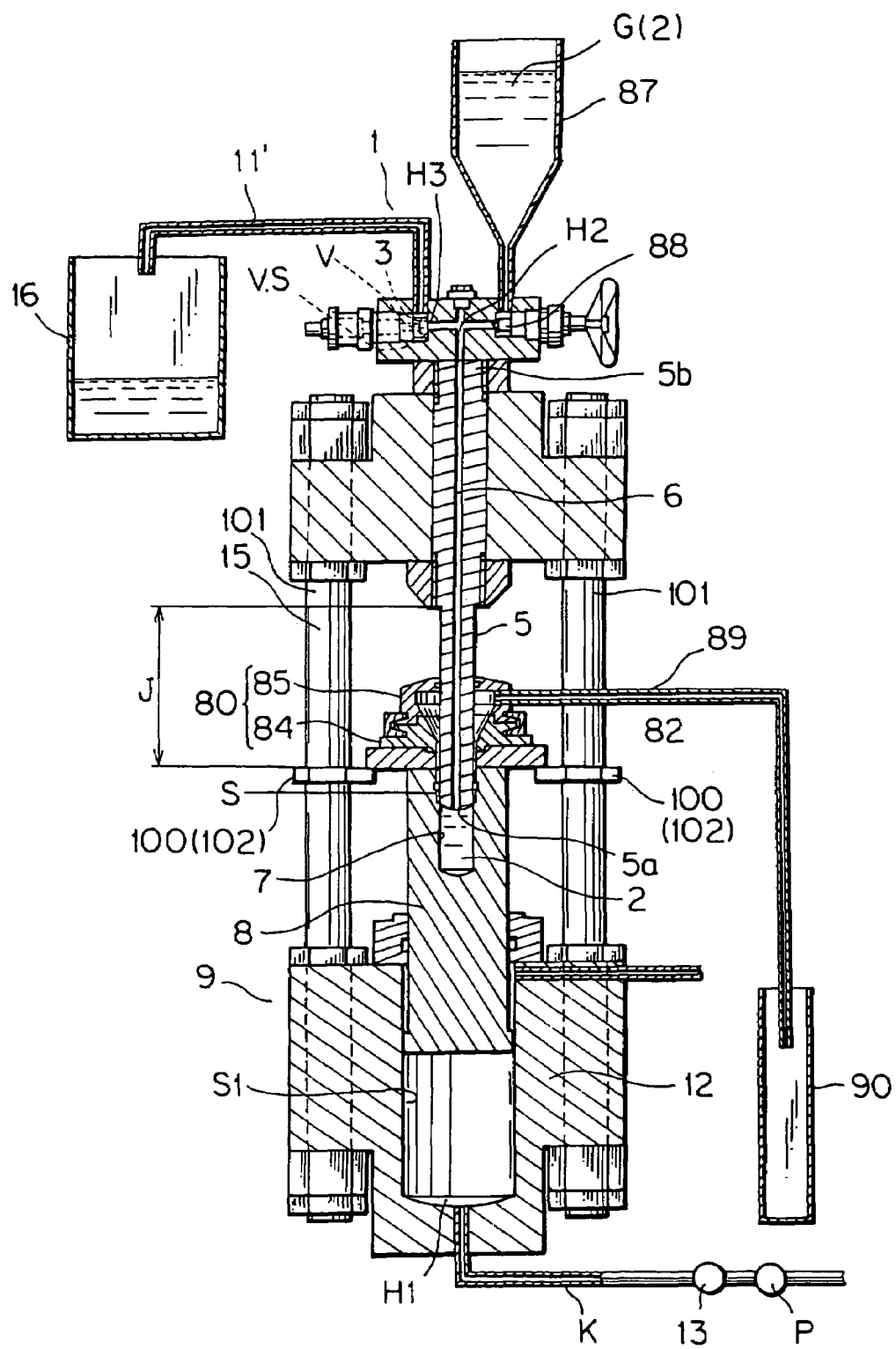
FIG. 55 is a sectional view showing that the supply of the suspension into the raw material receiving passage is finished after the fine division of the raw material.

The suspension 2 is passed through an orifice 3 at high speed to finely divide a raw material G of the solid material, fibrous cellulose, or cells (refer to FIG. 53). After the fine division, a booster piston 8 is moved downwardly to the initial position. When returning to the initial position, the increase volume inside the processing recess 7 leads the suspension 2 into the processing recess 7 and the suspension 2 is filled in the processing recess 7 over the watertight position S (refer to FIGS. 54 and 55).

After every fine division, the suspension 2 is supplied to the processing recess 7 from a hopper 87 by virtue of the increase of the volume inside the processing recess 7.

A stroke J of the processing piston 5 to move relative to the booster piston 8 at an automatic operation is adjusted with stroke controllers 100. As shown in FIGS. 49 to 55, each stroke controller 100 has a stopper 102 of a plate shape. The stopper 102 is attached eccentrically to a post 101 and can be rotated horizontally. At the automatic operation, when the booster piston 8 is moved up and down, the stoppers 102 are rotated to oppose to each other. The stoppers 102 lock a fixing plate 82 attached with the cover 80 detachably every time the booster piston 8 moves downwardly at the automatic operation so that the stoppers 102 can adjust the moving stroke J of the booster processing piston 5 of a pressure intensifier 9. The other formations and functions are the same as that of the fifteenth embodiment. The stroke controller 100 in the eighteenth embodiment controls mechanically the moving stroke J with the stoppers 102. The control of the moving stroke J is not limited to the mechanical type but can be adjusted by controlling a circuit K based on signals from electric, magnetic, and optical sensors.

What is claimed is:

1. A high pressure homogenizing apparatus, comprising:
   a high pressure homogenizing device;
   an orifice having a small diameter disposed at the high pressure homogenizing device for allowing a suspension containing a raw material including fine solid materials, fibrous celluloses, or cells to pass at a high speed under a high pressure;
   a raw material receiving passage connected to the high pressure homogenizing device;
   a processing piston to process the raw material;
   a pressure intensifier opposed to the processing piston; and
   a processing recess disposed in the pressure intensifier for accepting a front end of the processing piston;
   wherein one end of the raw material receiving passage is directly connected to the orifice and another end thereof is directed to face the processing recess;
   whereby said pressure intensifier or the processing piston is moved relative to each other and a volume inside the processing recess is compressed so that a desired amount of suspension containing the raw material is transferred, under high pressure, into the raw material receiving passage to be finely divided at the orifice of the high pressure homogenizing device.

2. The homogenizing apparatus as claimed in claim 1, wherein said processing recess is disposed inside a booster piston as a receiver, which moves relative to the processing piston fixed to a frame, of the pressure intensifier.

3. The homogenizing apparatus as claimed in claim 1, wherein said processing recess is disposed inside a movable cylinder as a receiver, which moves relative to the processing piston fixed to the frame, of the pressure intensifier.

4. The homogenizing apparatus as claimed in claim 1, wherein said processing recess is disposed inside a fixed cylinder as a receiver moving relative to the processing piston connected with a booster piston of the pressure intensifier movably disposed to the frame.

5. The homogenizing apparatus as claimed in claim 1, wherein said processing recess is disposed inside a movable cylinder as a receiver moving relative to the processing piston connected with a booster piston of the pressure intensifier movably disposed to the frame.

6. The homogenizing apparatus as claimed in one of claims 2-5, wherein said suspension containing the raw material is pressurized and led into the raw material receiving passage when the processing piston passes through a watertight position and the processing recess becomes watertight.

7. The homogenizing apparatus as claimed in claim 6, further comprising a hopper for supplying the suspension and disposed at an opening of the processing recess, the processing piston being inserted into the processing recess through the hopper at a watertight state.

8. The homogenizing apparatus as claimed in claim 3 or 5, wherein said booster piston, the processing piston, or the movable cylinder is returned to an initial position by a cylinder driven with the pressure intensifier after the suspension is led into the raw material receiving passage at a high pressure.

9. The homogenizing apparatus as claimed in claim 8, wherein said high pressure of the high pressure homogenizing device to finely divide the raw material is detected from a low pressure of oil or water led into a booster cylinder of the pressure intensifier, and a booster piston and the cylinder are automatically controlled and operated based on a plurality of detected signals.

10. The homogenizing apparatus as claimed in one of claims 2-5, wherein when said pressure intensifier is returned to an initial position after finely dividing the raw material, a relative movement of the receiver or the processing piston increases the volume inside the processing recess so that the suspension is led into the processing recess and filled over a watertight position in the processing recess.

11. The homogenizing apparatus as claimed in one of claims 2-5, wherein a relative moving stroke of the receiver or the processing piston at an automatic operation is adjusted with a stroke controller.

12. The homogenizing apparatus as claimed in one of claims 2-5, further comprising a detachable cover disposed at an upper face of the receiver to cover the processing recess and slidably passed through by the processing piston.

13. The homogenizing apparatus as claimed in claim 12, wherein said cover includes a fixing plate attached to an upper portion of the receiver having the processing recess, an annular cover main body attached to an upper face of the fixing plate and having a first locking edge at an outer circumference thereof, an upper cover having a through-hole for inserting the processing piston and a second locking edge to be faced with the first locking edge, and a plurality of collars separated in two parts to hold the first and second locking edges, the upper cover being detachable to the cover main body with the plurality of collars.

14. The homogenizing apparatus as claimed in claim 1, wherein said raw material receiving passage is disposed inside the processing piston in a longitudinal direction thereof.

15. The homogenizing apparatus as claimed in claim 1, wherein said raw material receiving passage is communicated between the processing recess and the high pressure homogenizing device and disposed in a radial direction of the processing recess.

16. The homogenizing apparatus as claimed in claim 1, wherein said raw material receiving passage is connected at one end to a bushing having a T or L-shaped section disposed at a lower position of the processing recess.

17. The homogenizing apparatus as claimed in claim 1, wherein said processing recess has a sliding valve therein at a lower position of the processing recess and the sliding valve opens and closes the raw material receiving passage with a spring responding to an internal pressure change.

18. The homogenizing apparatus as claimed in claim 1, wherein said suspension containing the raw material is pressurized and led into the raw material receiving passage when the processing piston passes through a watertight position and the suspension is filled in the processing recess and the raw material receiving passage at a watertight state.

19. The homogenizing apparatus as claimed in claim 1, wherein said pressure intensifier has a booster cylinder for oil or water to flow into and the booster piston disposed slidably inside the booster cylinder and having the processing recess at one end in a secondary path for inserting the front end of the processing piston.

20. The homogenizing apparatus as claimed in claim 1, wherein said pressure intensifier includes a booster cylinder for oil or water to flow into, a booster piston as the processing piston disposed slidably in the booster cylinder, and the cylinder having the processing recess at the one end for inserting the front end of the processing piston.

21. The homogenizing apparatus as claimed in claim 1, wherein said processing piston is moved manually to the initial position, at which initial position the suspension is filled over a watertight position, by a handle disposed around the processing piston.

22. The homogenizing apparatus as claimed in claim 1, wherein said processing piston is moved with a motor, a gear group having a drive gear attached to a shaft of the motor and a driven gear engaging with the drive gear and a screw disposed at an outer wall of the processing piston, a key groove disposed at the outer wall of the processing piston intersecting with the screw in an axial direction, and a key being locked into the key groove.

23. The homogenizing apparatus as claimed in claim 1, wherein said high pressure homogenizing device has a homogenizing valve moving along an axial direction thereof driven with oil pressure or air cylinder for pressing variably a valve seat at the orifice for adjusting an internal pressure to finely divide the raw material.

24. The homogenizing apparatus as claimed in claim 1, wherein said high pressure to finely divide the raw material including the solid material, fibrous cellulose, or cells contained in the suspension in the high pressure homogenizing device is determined by converting a low pressure of oil or water detected at a primary path inside the booster cylinder of the pressure intensifier.

25. The homogenizing apparatus as claimed in claim 1, wherein a plurality of high pressure homogenizing devices is connected to another end of a secondary path of the raw material receiving passage.

26. A high pressure homogenizing apparatus, comprising:
a high pressure homogenizing device;
an orifice having a small diameter disposed at the high pressure homogenizing device for allowing a suspension containing a raw material including fine solid materials, fibrous celluloses, or cells to pass at a high speed under a high pressure;
a raw material receiving passage connected to the high pressure homogenizing device;
a processing piston to process the raw material;
a pressure intensifier opposed to the processing piston; and
a processing recess disposed in the pressure intensifier for accepting a front end of the processing piston;
whereby said pressure intensifier or the processing piston is moved relative to each other and a volume inside the processing recess is compressed so that a desired amount of suspension containing the raw material is transferred, under high pressure, into the raw material receiving passage to be finely divided at the orifice of the high pressure homogenizing device;
wherein said raw material receiving passage is disposed inside the processing piston in a longitudinal direction thereof.

27. A high pressure homogenizing apparatus, comprising:
a high pressure homogenizing device;
an orifice having a small diameter disposed at the high pressure homogenizing device for allowing a suspension containing a raw material including fine solid materials, fibrous celluloses, or cells to pass at a high speed under a high pressure;
a raw material receiving passage connected to the high pressure homogenizing device;
a processing piston to process the raw material;
a pressure intensifier opposed to the processing piston; and
a processing recess disposed in the pressure intensifier for accepting a front end of the processing piston;
a detachable cover disposed at an upper face of the receiver to cover the processing recess and slidably passed through by the processing piston;
whereby said pressure intensifier or the processing piston is moved relative to each other and a volume inside the processing recess is compressed so that a desired amount of suspension containing the raw material is transferred, under high pressure, into the raw material receiving passage to be finely divided at the orifice of the high pressure homogenizing device;
wherein said raw material receiving passage is disposed inside the processing piston in a longitudinal direction thereof.

\* \* \* \* \*